(12) United States Patent
Wang et al.

(10) Patent No.: US 9,345,424 B2
(45) Date of Patent: May 24, 2016

(54) CLINICAL FORCE SENSING GLOVE

(75) Inventors: Wei-Chih Wang, Sammamish, WA (US); David J. Nuckley, Minneapolis, MN (US); Per G. Reinhall, Seattle, WA (US); David Linders, Seattle, WA (US)

(73) Assignee: University of Washington, Seattle, WA (US)

( * ) Notice: Subject to any disclaimer, the term of this patent is extended or adjusted under 35 U.S.C. 154(b) by 1454 days.

(21) Appl. No.: 13/058,523

(22) PCT Filed: Apr. 3, 2009

(86) PCT No.: PCT/US2009/039562
§ 371 (c)(1),
(2), (4) Date: Jun. 13, 2011

(87) PCT Pub. No.: WO2009/146142
PCT Pub. Date: Dec. 3, 2009

(65) Prior Publication Data
US 2011/0302694 A1 Dec. 15, 2011

Related U.S. Application Data

(60) Provisional application No. 61/042,214, filed on Apr. 3, 2008.

(51) Int. Cl.
*A61B 5/103* (2006.01)
*A61B 5/00* (2006.01)
*A61B 5/02* (2006.01)

(52) U.S. Cl.
CPC ................ *A61B 5/103* (2013.01); *A61B 5/6806* (2013.01); *A61B 5/02* (2013.01); *A61B 5/4528* (2013.01); *A61B 5/7207* (2013.01); *A61B 5/7257* (2013.01); *A61B 2562/0247* (2013.01); *A61B 2562/0266* (2013.01); *A61B 2562/043* (2013.01)

(58) Field of Classification Search
CPC ..................... A61B 2019/464; A61B 2019/465
USPC ................... 600/587, 595; 73/379.02, 379.03; 385/13
See application file for complete search history.

(56) References Cited

U.S. PATENT DOCUMENTS

| | | | | |
|---|---|---|---|---|
| 4,342,907 A | * | 8/1982 | Macedo et al. | 250/227.14 |
| 5,004,911 A | * | 4/1991 | Dankwort et al. | 250/227.21 |
| 5,020,379 A | * | 6/1991 | Berthold et al. | 73/800 |

(Continued)

OTHER PUBLICATIONS

McGorry, R.W. "A system for the measurement of grip forces and applied moments during hand tool use," Elsevier, Applied Ergonomics 32, 2001, pp. 271-279.

(Continued)

*Primary Examiner* — Adam J Eiseman
(74) *Attorney, Agent, or Firm* — Blakely Sokoloff Taylor & Zafman LLP

(57) ABSTRACT

A clinical sensing glove system to quantify force, shear, hardness, etc., measured in manual therapies is disclosed. A sensor is disposed in a clinical glove. The sensor undergoes micro-bending, macro-bending, evanescent coupling, a change in resonance, a change in polarization, a change in phase modulation, in response to pressure/force applied. The amount of micro-bending, macro-bending, evanescent coupling, change in resonance, change in polarization, and/or change in phase modulation is proportional to the intensity of the pressure/force. A clinician can quantitatively determine the amount of pressure, force, shear, hardness, rotation, etc., applied.

13 Claims, 44 Drawing Sheets

(56) References Cited

U.S. PATENT DOCUMENTS

| | | | | |
|---|---|---|---|---|
| 5,656,785 | A * | 8/1997 | Trainor et al. | 73/862.46 |
| 6,033,370 | A * | 3/2000 | Reinbold et al. | 600/595 |
| 6,325,768 | B1 | 12/2001 | Williams et al. | |
| 6,589,171 | B2 | 7/2003 | Keirsbilck | |
| 6,681,638 | B2 * | 1/2004 | Kazerooni et al. | 73/760 |
| 7,426,872 | B2 * | 9/2008 | Dittmar et al. | 73/818 |
| 7,562,572 | B2 * | 7/2009 | You et al. | 73/379.03 |
| 7,780,541 | B2 * | 8/2010 | Bauer | 473/205 |
| 7,845,225 | B2 * | 12/2010 | Ridenour et al. | 73/379.02 |
| 2005/0232532 | A1 * | 10/2005 | Wang et al. | 385/13 |
| 2007/0167844 | A1 | 7/2007 | Asada et al. | |
| 2007/0183734 | A1 | 8/2007 | Fukushi et al. | |
| 2007/0219469 | A1 * | 9/2007 | Vardy | 600/587 |
| 2008/0076995 | A1 | 3/2008 | Hoarau | |
| 2013/0158365 | A1 * | 6/2013 | Chey et al. | 600/301 |
| 2013/0197399 | A1 * | 8/2013 | Montgomery | 600/595 |

OTHER PUBLICATIONS

Levin, U. et al., "Variability of forces applied by experienced physiotherapists during provocation of the sacroiliac joint," Elsevier, Clinical Biomechanics 16, 2001, pp. 300-306.
Moeller, J.F. et al., "Projecting National Medical Expenditure Survey Data: A Framework for MEPS Projections," MEPS Methodology Report 13, AHRQ Pub. No. 02-0009 (DHHS) Feb. 2002, 30 pages.
Chiradejnant, A. et al., "Forces Applied During Manual Therapy to Patients With Low Back Pain," Journal of Manipulative & Physiological Therapeutics, vol. 25, No. 6, 2002, pp. 362-369.
Odom, T.W. et al., "Improved Pattern Transfer in Soft Lithography Using Composite Stamps," Langmuir, vol. 18, No. 13, 2002, pp. 5314-5320.
Rogers, C.M. et al., "Biomechanical Measure Validation for Spinal Manipulation in Clinical Settings," Journal of Manipulative & Physiological Therapeutics, vol. 26, No. 9, 2003, pp. 539-548.
Triano, JJ.et al., "Quantitative Feedback Versus Standard Training for Cervical and Thoracic Manipulation," Journal of Manipulative & Physiological Therapeutics, vol. 26, No. 3, 2003, pp. 131-138.
Sumriddetchkajorn, S. "Optical touch switch based on total internal reflection," Optical Engineering, vol. 42, No. 3, Mar. 2003, pp. 787-791.
McQuade, K.J. et al., "Anterior glenohumeral force/translation behavior with and without rotator cuff contraction during clinical stability testing," Elsevier, Clinical Biomechanics vol. 19, 2004, pp. 10-15.
Forand, D. et al., "The Forces Applied by Female and Male Chiropractors During Thoracic Spinal Manipulation," Journal of Manipulative & Physiological Therapeutics. vol. 27, No. 1, Jan. 2004, pp. 49-56.
Nikonovas. A. et al., "The application of force-sensing resistor sensors for measuring forces developed by the human hand," Proceedings of the Institution of Mechanical Engineers, Part H: Journal of Engineering in Medicine, vol. 218, 2004, pp. 121-126.
Tholey, G. et al., "Force Feedback Plays a Significant Role in Minimally Invasive Surgery," Results and Analysis, Annals of Surgery, vol. 241, No1. 1, Jan. 2005, pp. 102-109.
Wang, W.C. et al., "A shear and plantar pressure sensor based on fiber-optic bend loss," JRRD, Journal of Rehabilitation Research & Development, vol. 42, No. 3, 2005, pp. 315-325.
Levin, U. et al., "Variability Within and Between Evaluations of Sacroiliac Pain With the Use of Distraction Testing," Journal of Manipulative & Physiological Therapeutics, vol. 28, No. 9, 2005, pp. 688-695.
Colloca, C.J. et al., "Comparison of Mechanical Force of Manually Assisted Chiropractic Adjusting Instruments," Journal of Manipulative & Physiological Therapeutics, vol. 28, No. 6, 2005, pp. 414-422.
Fukuda, Y. et al., "MEMS and Fiber Optics Sensor-Based Wearable Interface for Medical Applications," In Proceedings of IEEE International Conference on System, Man and Cybernetics, 2, 2005, pp. 814-817.
Simone, L. et al., "Design considerations for a wearable monitor to measure finger posture," Journal of Neuroengineering and Rehabilitation, BioMed Central, 2005; 2:5, 10 pages.
Sumriddetchkajorn, S. et al., "Optical Touch Sensor Technology," Lasers and Electro-Optics Society, 2005. LEOS 2005. The 18th Annual Meeting of the IEEE, Oct. 2005, 2 pages.
Pylatiuk, C. et al., "Distribution of grip force in three different functional prehension patterns," Journal of Medical Engineering & Technology, vol. 30, No. 3, 2006, pp. 176-182.
Sumriddetchkajorn, S. et al., "Ultra-high-contrast low-leakage-light optical touch device structures using light scattering and total internal reflection concepts," Elsevier, Sensors and Actuators A 126, 2006, pages 68-72.
Latex Glove Manufacturing Process, Medical Exam Glove, 2006, http://www.medicalexamglove.com/latex_gloves/manufacturing_process.html.
Sumriddetchkajorn, S. et al., "Surface plasmon resonance-based highly sensitive optical touch sensor with a hybrid noise rejection scheme," Applied Optics, vol. 45, No. 1, Jan. 2006, pp. 172-177.
Waddington, G.S. et al., "Initial development of a device for controlling manually applied forces," Elsevier, Science Direct, Manual Therapy 12, 2007, pp. 133-138.
Owens, E.F. Jr. et al., "The Reliability of a Posterior-to-Anterior Spinal Stiffness Measuring System in a Population of Patients With Low Back Pain," Journal of Manipulative & Physiological Therapeutics, vol. 30, No. 2, Feb. 2007, pp. 116-123.
Owens, E.F. Jr. et al., "Comparison of Posteroanterior Spinal Stiffness Measures to Clinical and Demographic Findings at Baseline in Patients Enrolled in a Clinical Study of Spinal Manipulation for Low Back Pain," Journal of Manipulative & Physiological Therapeutics, vol. 30, No. 7, Sep. 2007, pp. 493-500.
King, R.C. et al., "An HMM Framework for Optimal Sensor Selection with Applications to BSN Sensor Glove Design," Proceedings of the 4th workshop on Embedded networked sensors 2007, Cork, Ireland Jun. 25-26, 2007, pp. 58-62.
Reiley, C.E. et al., "Effects of visual force feedback on robot-assisted surgical task performance," Evolving Technology, The Journal of Thoracic & Cardiovascular Surgery, vol. 135, No. 1, Jan. 2008, pp. 196-202.
Chen, A. et al., "Microring Resonators Made in Poled and Unpoled Chromophore-Containing Polymers for Optical Communication and Sensors," IEEE Journal of Selected Topics in Quantum Electronics, vol. 14, No. 5, 2008, pp. 1281-1288.
Huang, C. et al., "Flexible polymeric rib waveguide with self-align couplers system," Journal of Vacuum Science and Technology B, vol. 26, No. 1, 2008, pp. L13-L18.
Dean, M. et al.; "Semiconductor and Conventional Strain Gages;" New York, Academic Press (1962); pp. 109-125, 247, and 301-345.
Wolf, H.F., "Handbook of Fiber Optics Theory and Applications," Chapter 2, Optical Waveguides, Granada (1979) pp. 43-152.
Ferraresi, C. et al., "A Low Cost Pneumo-Electronic Tactile Sensor," Proceedings of International Conference on Recent Advances in Mechatronics, ICRAM '95, Istanbul, Turkey, Aug. 1995, pp. 1098-1103.
Herzog, W., "Clinical Biomechanics of Spinal Manipulation," Chapter 4, The Mechanics of Spinal Manipulation, Philadelphia: Churchill Livingstone (2000) pp. 92-190.
PCT/US2009/039562, International Search Report and Written Opinion of the International Searching Authority, mail date Nov. 24, 2009, 11 pages.
Mason, W.P. et al., "Use of Piezoresistive Materials in the Measurement of Displacement, Force, and Torque," The Journal of the Acoustical Society of America, vol. 29, No. 10, Oct. 1957, pp. 1096-1101.
Samaun et al., "An IC Piezoresistive Pressure Sensor for Biomedical Instrumentation," IEEE Transaction on Biomedical Engineering, vol. BME -20, No. 2, Mar. 1973, pp. 101-109.
Varnham, M.P. et al., "Polarimetric Strain Gauges Using High Birefringence Fibre," Electronics Letters, vol. 19, No. 17, Aug. 1983, pp. 699-700.
Dario, P. et al., "Ferroelectric Polymer Tactile Sensors for Prostheses," Ferroelectrics, vol. 60, 1984, pp. 199-214.
Wood, J. et al., "Comparison of forces used in selected adjustments of the low back by experienced chiropractors and chiropractic students

(56) References Cited

OTHER PUBLICATIONS with no clinical experience: a preliminary study," PCC Research Forum, Autumn, 1984, Palmer College of Chiropractic, pp. 16-23.
Ogorek, M., "Tactile Sensors," Manufacturing Engineering, Feb. 1985, pp. 69-77.
Chu, P.L. et al., "Phase Sensitivity of Polarization-Maintaining Optical Fiber Used as Temperature Sensor," Journal of Lightwave Technology, vol. LT-4, No. 1, 1986, pp. 44-49.
Begej, S., "Planar and Finger-Shaped Optical Tactile Sensors for Robotic Applications," IEEE Journal of Robotics and Automation, vol. 4, No. 5, Oct. 1988, pp. 472-484.
Winger, J.G. et al., "Experimental Investigation of a Tactile Sensor Based on Bending Losses in Fiber Optics", 1988 Proceedings, 1988 IEEE International Conference on Robotics and Automation, 1988, pp. 754-759.
Jenstrom, D.T. et al., "A Fiber Optic Microbend Tactile Sensor Array," Sensors and Actuators, 20, 1989, pp. 239-248.
5DT Data Glove 5 MRI/ 5DT Data Glove 14 MRI, Fifth Dimension Technologies, downloaded on Oct. 19, 2011, http://www.5dt.com/products/pdataglovemri.html.
Lee, M. et al., "Effect of Feedback on Learning a Vertebral Joint Mobilization Skill," Physical Therapy vol. 70, No. 2, Feb. 1990, pp. 97-102.
Hessell, B.W. et al., "Experimental Measurement of the Force Exerted During Spinal Manipulation Using the Thompson Technique," Journal of Manipulative & Physiological Therapeutics, vol. 13, No. 8, Oct. 1990, pp. 448-453.
Wise, S. et al., "Evaluation of a fiber optic glove for semi-automated goniometric measurements," Journal of Rehabilitation Research and Development, vol. 27, No. 4, 1990, pp. 411-424.
Emge, S.R. et al., "Two-dimensional contour imaging with a fiber optic microbend tactile sensor array," Sensors and Actuators B, 3, 1991, pp. 31-42.
Conway, P.J.W. et al., "Forces required to cause cavitation during spinal manipulation of the thoracic spine," Clinical Biomechanics, vol. 8, No. 4, 1993, pp. 210-214.
Herzog, W. et al., "Forces Exerted During Spinal Manipulative Therapy," Spine, vol. 18, No. 9, 1993, pp. 1206-1212.
Wilder, D.G. et al., "Epidemiological and aetiological aspects of low back pain in vibration environments—an update," Elsevier, Review Paper, Clinical Biomechanics, vol. 11, No. 2, 1996, pp. 61-73.
Petty, N. J. et al., "Can the Force Platform be Used to Measure the Forces Applied During a PA Mobilisation of the Lumbar Spine?" The Journal of Manual & Manipulative Therapy, vol. 4, No. 2, 1996, pp. 70-76.
Inaba, M. et al., "A Full-Body Tactile Sensor Suit Using Electrically Conductive Fabric and Strings," Intelligent Robots and Systems '96, IROS 96, Proceedings of the 1996 IEEE/RSJ International Conference on Intelligent Robots and Systems, Osaka, Japan, vol. 2, Nov. 1996, pp. 450-457.
Hu, W. et al., "Force-sensitive resistor of carbon-filled liquid silicone rubber," Journal of Applied Physics, vol. 79, No. 2, Jan. 1996, pp. 866-870.

Day, R.A. "PVDF and Array Transducers," Transducer 96 Workshop, vol. 1, No. 9 Sep. 1996, 8 pages.
Kolesar, E.S. et al., "Tactile Integrated Circuit Sensor Realized with a Piezoelectric Polymer," 1996 Proceedings, Eighth Annual IEEE International Conference on Innovative Systems in Silicon, Austin, Texas, USA, Oct. 1996, pp. 372-381.
Ohta, R., "Recent Achievements on MOEM Systems at MMC," Conference on Miniaturized Systems with Micro-Optics and Micromechanics, SPIE vol. 2687, 1996, pp. 2-7.
Harms, M.C. et al., "Variability of forces applied by experienced therapists during spinal mobilization," Elsevier, Clinical Biomechanics, vol. 12, No. 6, 1997, pp. 393-399.
Triano, J. et al., "Loads Transmitted During Lumbosacral Spinal Manipulative Therapy," Spine, Biomechanics, vol. 22 (17) Sep. 1997, 15 pages.
Burdea, G. et al., "Computerized Hand Diagnostic/Rehabilitation System Using a Force Feedback Glove," Studies in Health Technology & Informatics, Medicine Meets Virtual Reality, IOS Press, 1997, pp. 141-150.
Shinoda, H. et al., "Tactile Sensing Based on Acoustic Resonance Tensor Cell," IEEE, Transducers 97, 1997 International Conference on Solid-State Sensors and Actuators, Chicago, Illinois, USA, Jun. 1997, pp. 129-132 (1B3.08P).
Fiorillo, A.S., "A Piezoresistive Tactile Sensor," IEEE Transaction on Instrumentation and Measurement, vol. 46, No. 1, Feb. 1997, pp. 15-17.
Kim, E. et al., "Solvent-Assisted Microcontact Molding: A Convenient Method for Fabricating Three-Dimensional Structures on Surface of Polymers," Advanced Materials, vol. 9, No. 8, 1997, pp. 651-654.
Hintermeister, R.A. et al., "Quantification of Elastic Resistance Knee Rehabilitation Exercises," Journal of Orthopaedic & Sports Physical Therapy, vol. 28, No. 1, Jul. 1998, pp. 40-50.
Levin, U. et al., "Reproducibility of manual pressure force on provocation of the sacroiliac joint," Physiotherapy Research International, 3(1) 1998, 14 pages.
Paschen, U. et al., "A novel tactile sensor system for heavy-load applications based on an integrated capacitive pressure sensor," Elsevier, Sensors and Actuators A, 68, 1998, pp. 294-298.
Dargahi, J. et al., "Surface texture measurement by combining signals from two sensing elements of a piezoelectric tactile sensor," SPIE vol. 3376, 1998, pp. 122-128.
Li, P. et al., "An arbitrarily distributed tactile piezoelectric sensor array," Elsevier, Sensors and Actuators A 65, 1998, pp. 141-146.
Beebe, D.J. et al., "A Silicon-Based Tactile Sensor for Finger-Mounted Applications," IEEE Transactions on Biomedical Engineering, vol. 45, No. 2, Feb. 1998, pp. 151-159.
Wang, L. et al., "Shear Sensitive Silicon Piezoresistive Tactile Sensor Prototype," Part of the SPIE Conference on Micromachined Devices and Components IV, Santa Clara, CA, USA, Sep. 1998, SPIE, vol. 3514, pp. 359-367.
Andersson, G.B.J. "Epidemiological features of chronic low-back pain," Lancet 1999, 354, pp. 581-585.

* cited by examiner

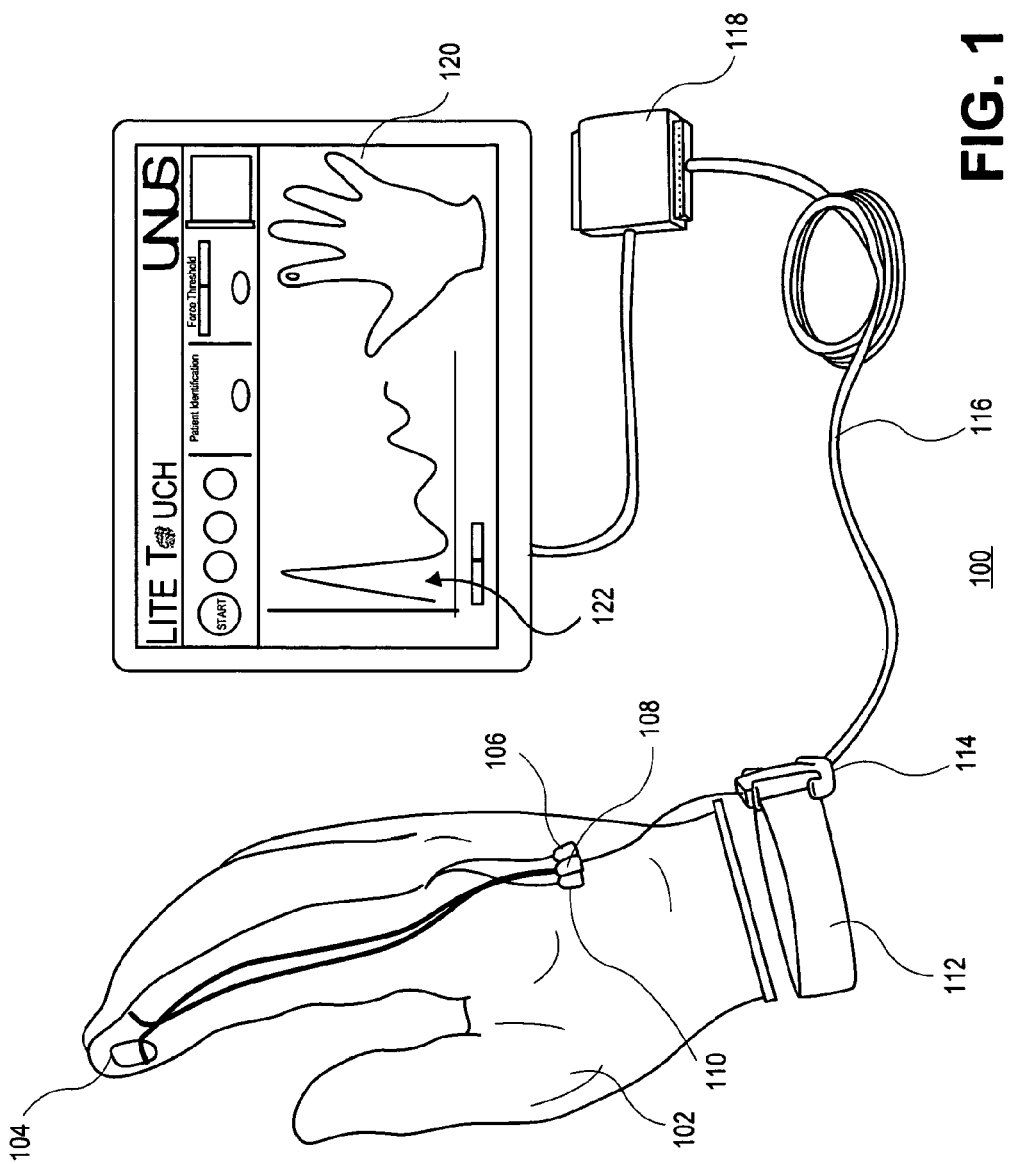

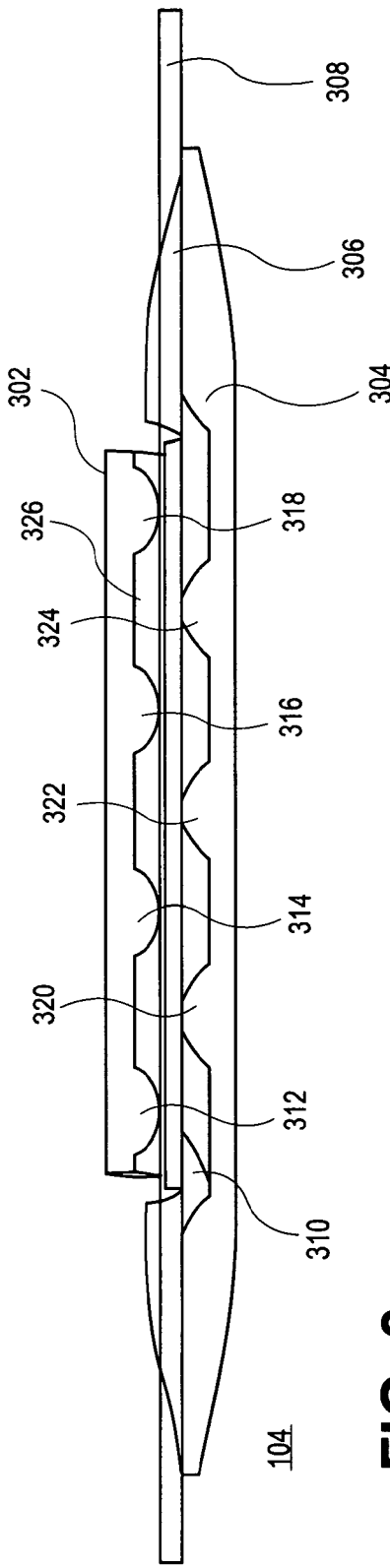
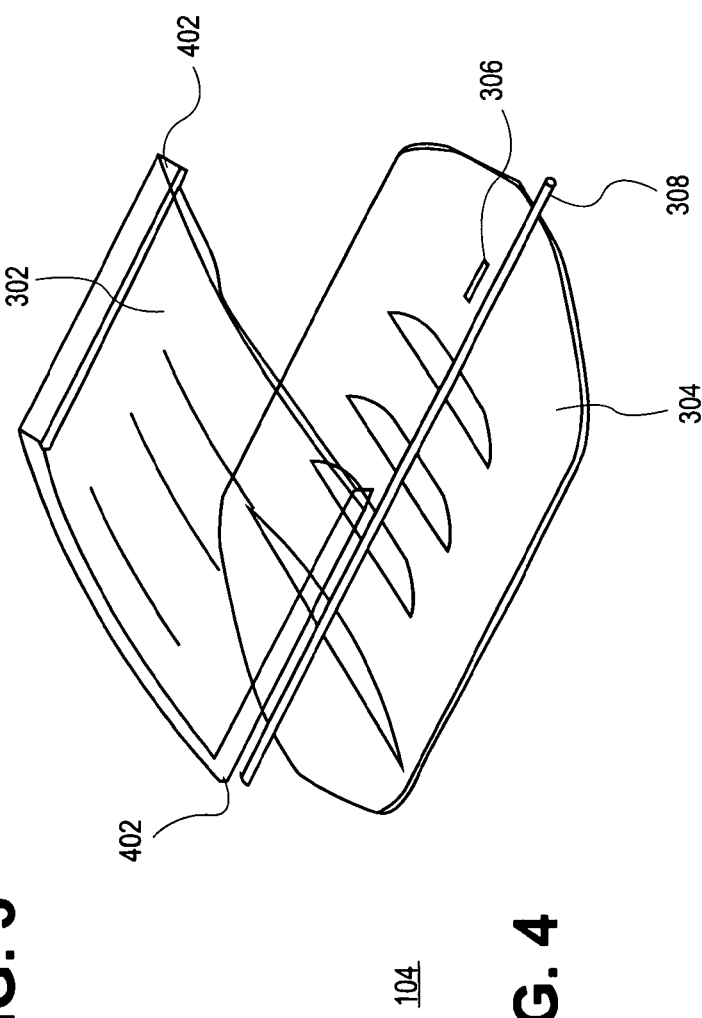
FIG. 3
FIG. 4

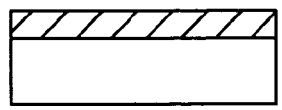
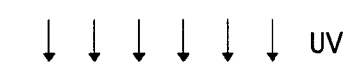
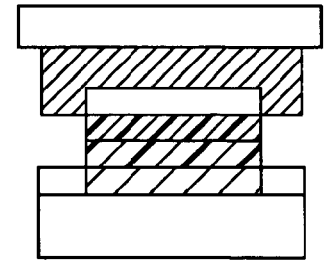
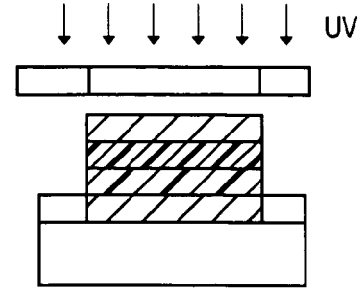

CLINICAL FORCE SENSING GLOVE

CROSS-REFERENCE TO RELATED APPLICATIONS

This application claims the benefit of U.S. Provisional Application No. 61/042,214, filed Apr. 3, 2008.

BACKGROUND

1. Field

Embodiments of the present invention relate tools for quantitatively measuring parameters such as force, shear, hardness, pressure, etc., generated during manual diagnosis, treatment, and evaluation of patients.

2. Discussion of Related Art

Frequently, patient diagnosis and treatment involves a clinician placing his or her hands upon the patient. Manual healthcare providers are increasingly adopting leading edge technologies to improve these diagnoses and treatments. However, in physical therapy, chiropractics, and general medicine, the classical standard of manual care and diagnosis remains the qualitative biologic sensors within the clinician's hands.

Manual diagnosis and therapy encompasses numerous disciplines but is most prevalently practiced by physical therapists, chiropractors, orthopedists, and doctors of osteopathy. Together, these sectors of physical medicine may treat over 70% of the U.S. population for ongoing care, and representing an industry value of greater than $130 billion. Specifically, the growing aging population is increasing demand for chiropractic care, and the U.S. annually spends more than $42 billion in treating lower back pain alone. These expenses and high incidence of treatment highlight physical medicine's importance in the health of our nation.

Manual diagnosis and therapy classically involves the physical application of loads to the body to produce joint displacements, altered local stress, and/or relief of pain and discomfort. This physical application of loads to the body is not currently widely measured in clinical practice. Waddington et al. in "Initial development of a device for controlling manually applied forces," Manual Therapy 2007: 12(2):133-8, noted that " . . . substantial variability has been shown when therapists attempt to replicate an applied force." This variability can significantly alter the effectiveness of the clinician to achieve their desired clinical outcome.

Specific examples in manual diagnosis and therapy that would benefit from objective measures of the applied loads include: provocative tests to evaluate painful joints, evaluation of patient improvement, and delivery of safe forces to the patient. From visit to visit, a record of the forces applied to a specific patient would improve patient care and the ability of the clinician to evaluate patient progress. In the assessment of thoracic spine manipulations, intra-clinician variability was measured to be as high as 42% for chiropractors attempting to reproduce a particular outcome. Pain-provocation tests on patients have likewise been found to vary considerably between tests and clinicians. Levin et al. reported that "The findings indicate the advantage of registering pressure force as a complement for standardized methods for pain-provoking tests and when learning provocation tests, since individual variability was considerable."

Manual palpation methods for diagnosis and treatment have long suffered from objectivity, inter-examiner variability, and intra-examiner variability. Until recently, very few scientific studies have quantified manipulation procedures to associate biomechanical manipulation with relief of symptoms. The following review describes both the state of the art in measurement techniques and the results and benefits of manipulation force measurement.

Quantifying manual force application has been accomplished theoretically, through inverse dynamics, and via direct measurement. Measurement of the forces clinicians apply to their patients has been accomplished using instrumented tools, gloves, and tables. Together, these measurement systems have improved the knowledge base for physical medicine and individual patient care.

At some point in their lives, most people may receive physical treatment for musculoskeletal ailments, such as muscle strains, ligament sprains, joint replacements, and arthritis. More than seventy percent of the U.S. population may seek clinical care that is physical or biomechanical in nature. The clinical care sought may include physical therapy, orthopedic surgery, or chiropractic care, for example. Treatments in these specialties rely on the forces that the clinician applies with their hands. Unfortunately, hospitals and clinics currently lack a tool for the measurement of these forces, leaving diagnosis and treatment subjective.

In this age of evidence based clinical care, objective measurements of the forces clinicians apply to their patients may lead to wide-spread improvements in care. Current clinical biomechanical assessments and treatments contain variability between clinicians and visits which has been shown to influence outcomes. Previous research has identified the need for a tool to measure forces at the hands in clinical diagnosis and treatment. Unfortunately, no universally applicable off-the-shelf measurement system exists.

As evidence based medicine advances and improves the healthcare industry, it is imperative that manual diagnosis and therapy remain on the leading edge due to their importance to patient health. Quantification of the physical forces that clinicians apply to their patients represents a significant step towards defining and motivating evidence-based outcomes in physical medicine. Although many different traditional sensors have been used to assist the clinician in understanding the forces they are applying to their patients, few of these devices measure the direct forces between the clinician and patient, and none are widely available to clinicians.

BRIEF DESCRIPTION OF THE DRAWINGS

In the drawings, like reference numbers generally indicate identical, functionally similar, and/or structurally equivalent elements. The drawing in which an element first appears is indicated by the leftmost digit(s) in the reference number, in which:

FIG. 1 is a schematic diagram of a clinical sensing system for a micro bend-loss sensor according to an embodiment of the present invention;

FIG. 3 is a computer-aided design (CAD) rendering of a side view of a flexible micro bend-loss sensor according to an embodiment of the present invention;

FIG. 4 is a CAD rendering of a disassembled view of the flexible sensor depicted in FIG. 3 according to an embodiment of the present invention;

FIG. 15($b$) illustrates hard PDMS (hPDMS) spin coated on a master over the grating pattern of FIG. 15($a$), and PDMS spin coated on the hPDMS for a grating-based sensor according to an embodiment of the present invention;

FIG. 15($c$) illustrates polymer (hPDMS and PDMS) separated from a mold/master for a grating-based sensor according to an embodiment of the present invention;

FIG. 16($b$) illustrates a solvent-assist micro-contact molding (SAMIM) process used to transfer a grating pattern onto an epoxy-based SU-8 film for a grating-based sensor according to an embodiment of the present invention, in which the hPDMS stamp is placed on top of a pre-baked SU82002 film without any pressure applied;

FIG. 16($c$) illustrates a solvent-assist micro-contact molding (SAMIM) process used to transfer a grating pattern onto an epoxy-based SU-8 film for a grating-based sensor according to an embodiment of the present invention, in which the grating pattern was transferred to SU8 film after the stamp was released;

FIG. 16($d$) illustrates a solvent-assist micro-contact molding (SAMIM) process used to transfer a grating pattern onto an epoxy-based SU-8 film for a grating-based sensor according to an embodiment of the present invention, in which the waveguide trench is patterned using photolithography;

FIG. 16($e$) illustrates a solvent-assist micro-contact molding (SAMIM) process used to transfer a grating pattern onto an epoxy-based SU-8 film for a grating-based sensor according to an embodiment of the present invention, in which the hPDMS and PDMS are spin coated;

FIG. 16($f$) illustrates a solvent-assist micro-contact molding (SAMIM) process used to transfer a grating pattern onto an epoxy-based SU-8 film for a grating-based sensor according to an embodiment of the present invention, in which the polymer is released from the mold once it is cured;

FIG. 23($a$) illustrates a process for fabricating an electro-optic Fourier transform spectrometer interrogating system for a disposable clinical glove in which metal is disposed on a bottom electrode according to an embodiment of the present invention;

FIG. 23($b$) illustrates a process for fabricating an electro-optic Fourier transform spectrometer interrogating system for a disposable clinical glove in which a bottom electrode may be patterned using a mask and ultraviolet (UV) radiation according to an embodiment of the present invention;

FIG. 23($c$) illustrates a process for fabricating an electro-optic Fourier transform spectrometer interrogating system for a disposable clinical glove in which a cladding layer is disposed on the remaining metal according to an embodiment of the present invention;

FIG. 23($d$) illustrates a process for fabricating an electro-optic Fourier transform spectrometer interrogating system for a disposable clinical glove in which an electro-optic polymer is disposed on the cladding layer according to an embodiment of the present invention;

FIG. 23($e$) illustrates a process for fabricating electro-optic Fourier transform spectrometer interrogating system for a disposable clinical glove in which another metal layer may be disposed on the imprinted electro-optic polymer to form a top electrode according to an embodiment of the present invention;

DETAILED DESCRIPTION OF THE ILLUSTRATED EMBODIMENTS

Figure 2A:
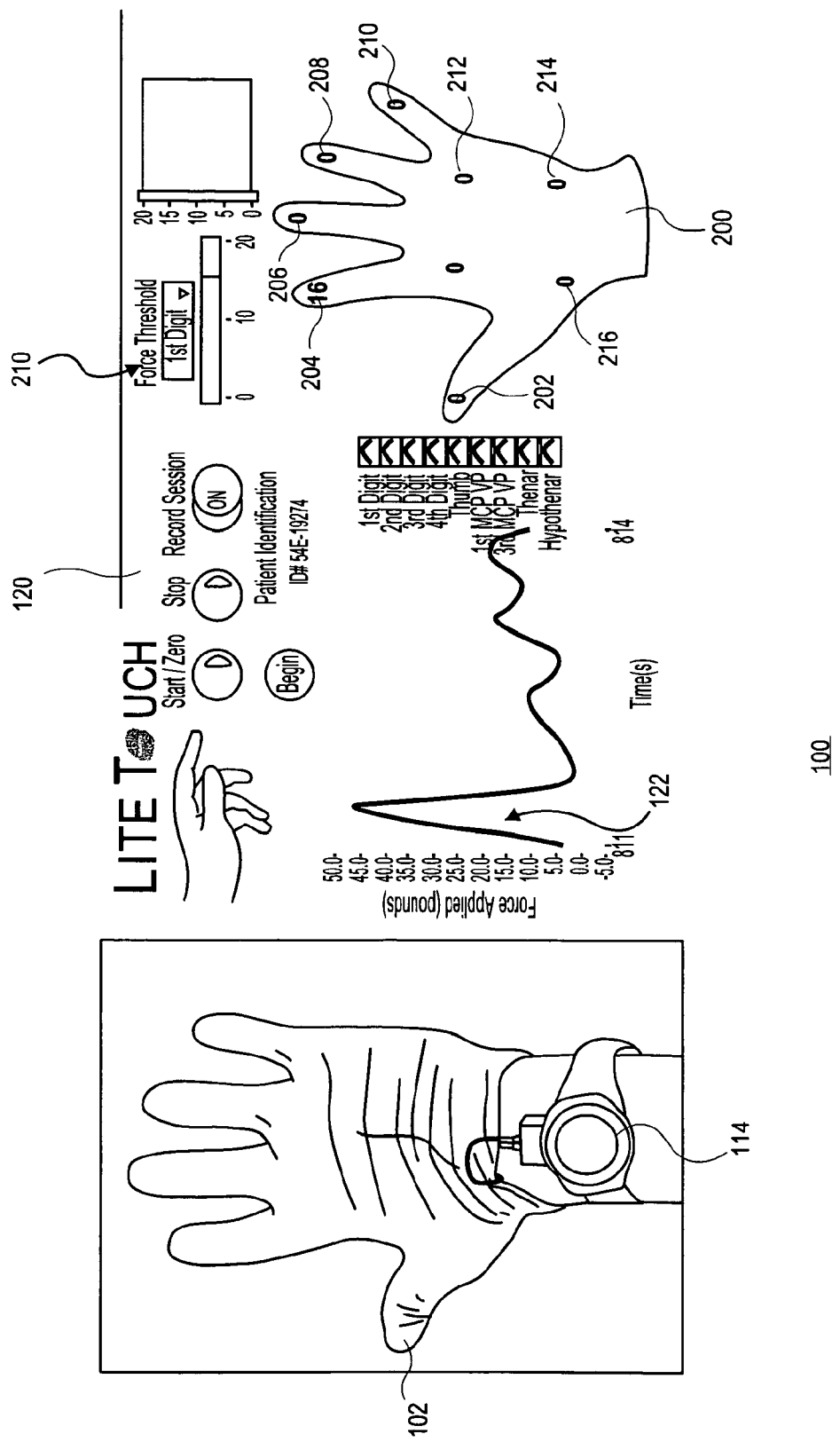
FIG. 2(a) is a view of the clinical sensing glove depicted in FIG. 1 along with a more detailed view of the display depicted in FIG. 1 according to an embodiment of the present invention.

Embodiments of the present invention are directed to a disposable clinical sensing glove intended to provide objective feedback in a clinical setting. The clinical sensing glove includes sensors in the thumb, fingers, and the palm of the glove. Several optical techniques and fabrications are implemented, including a microbend loss technique, a macrobend loss technique, an evanescent coupling technique, a polarimetric sensing technique, a phase modulation technique, a grating-based sensing technique, and a ring resonator sensing technique.

For some embodiments, the sensors may be in an optical fiber configuration and/or a micro-fabricated waveguide version. A light source is coupled to input an optical signal to the optical fiber and/or micro-fabricated waveguide. A light detector is coupled to detect light exiting the optical fiber optical fiber and/or micro-fabricated waveguide. When the fingers and/or other parts of the glove press on a sensor, a change in the characteristics of the light may be detected by the light detector. The change is proportional to the type of contact with the sensor.

Optionally, there may be a wrist cuff that houses the light source, light detector, supporting circuitry, power, etc., and the signal from the sensor may be transmitted by the wrist cuff to a display station. Additionally, for some embodiments, only the glove with the sensors is disposed of after use and the wrist cuff is re-usable.

Disposable Clinical Glove Having Micro Bend-Loss Sensor(s)

FIG. 1 is a view of a clinical force sensing system 100 according to an embodiment of the present invention. The illustrated system 100 includes a glove 102 having a flexible sensor 104 disposed in a fingertip portion of the glove 102.

The flexible sensor 104 is operationally coupled to a light detector 106, a light source 108, and a second light detector 110. The illustrated system 100 also includes a wrist cuff 112, which is operationally coupled to the two light detectors 106 and 110, as well as to the light source 108. The wrist cuff 112 includes a control panel 114, which may house the operational circuitry and one or more power supplies for the light source 108 and the light detectors 106 and 110. A cable 116 operationally couples the control panel 114 to a data acquisition module 118. The data acquisition module 118 is operationally coupled to a graphical display and control module 120. A graph 122 is a graphical representation of the force applied to the sensor 104 using the fingertip.

FIG. 2(a) is a view of the clinical force sensing system 100 along with a more detailed view of the graphical display and control module 120 according to an embodiment of the present invention. The system 100 illustrated in FIG. 2(a) shows the glove 102 operationally coupled to the control panel 114 on the wrist cuff 112. The graphical display and control module 120 also illustrates the graph 122. The system 100 illustrated in FIG. 2(a) also shows a graphical representation 200 of the glove 102 along with an indication of the amount of force that is applied by a particular portion of a disposed in the glove 102.

For example, the graphical representation 200 indicates that the thumb in the thumb portion 202 of the glove 102 is applying 0 Newtons to the flexible sensor 104 disposed in the thumb portion 202. The graphical representation 200 indicates that the $1^{st}$ finger in the $1^{st}$ finger portion 204 of the glove 102 is applying 16 Newtons to the flexible sensor 104 disposed in the $1^{st}$ finger portion 204. The graphical representation 200 indicates that the $2^{nd}$ finger in the $2^{nd}$ finger portion 206 of the glove 102 is applying 0 Newtons to the flexible sensor 104 disposed in the $2^{nd}$ finger portion 206. The graphical representation 200 indicates that the $3^{rd}$ finger in the $3^{rd}$ finger portion 208 of the glove 102 is applying 0 Newtons to the flexible sensor 104 disposed in the $3^{rd}$ finger portion 208. The graphical representation 200 indicates that the $4^{th}$ finger in the $4^{th}$ finger portion 210 of the glove 102 is applying 0 Newtons to the flexible sensor 104 disposed in the $4^{th}$ finger portion 210. The graphical representation 200 also indicates that the palm portions 212, 214, 216, and 218 of the glove 102 each is applying 0 Newtons to the flexible sensor 104 disposed in the palm portions 212, 214, 216, and 218.

Additionally, the graphical display and control module 120 include the options for a user to enable the setting of a force threshold warning (reference number 220) and to record a session for review (reference number 222).

For some embodiments, the glove 102 may be a standard disposable medical glove, such as a latex glove. The glove 102 may be similar to Nitrile disposable clinical surgical gloves. For other embodiments, the glove 102 may include a polymer material.

For some embodiments, the sensor 104 may be a low-profile fiber-optic sensor embedded in the glove 102. The low-profile fiber-optic sensor 104 has been embedded within a standard medical glove an effort to provide the medical community with a technology having the benefits of force feedback without requiring a change in technique. In using a fiber-optic sensor, a clinician's function is minimally affected, greater signal-to-noise ratio in a medical environment may be achieved, and the safety of the patient may be maintained. When embedded within a latex glove the fiber-optic sensor 104 may be thin enough and sufficiently low profile (<1 mm) to enable a clinician to feel a patient qualitatively as the quantitative measurements are acquired. The use of light as a transduction media makes the sensor 104 inert to hospital or clinical 'noise' generated by other equipment. Moreover, the sensor 104 may operate without affecting or interfering with other critical medical instrumentation.

The flexible sensors 104 in the clinical force sensing glove system 100 may report force data to the wrist cuff 112. The wrist cuff 112 then transmits the force data via a wireless link, such as Bluetooth, for example, to the display unit, where both visual and audio feedback can be given to the clinician. This clinical force sensing glove system 100 can be produced at a low cost (<$800) to facilitate the ease of use and implementation.

The fiber-optic sensor 104 intended for use in the force sensing glove system 100 is designed for biologic applications and with manual therapy design criteria. The light source 104 may be any suitable light source capable of emitting light. For some embodiments, the light source 104 emits a visible light, ultraviolet (UV), and infrared (IR) light sources. In other embodiments, the light source 106 emits single mode, multimode, single band, and broad band light.

The light detectors 106 and/or 110 may be any suitable light detectors capable of receiving light and converting it to an electrical signal proportional to the amount of light received. For some embodiments, the light detectors 106 and/or 110 respond to visible light, ultraviolet (UV), and infrared (IR) light sources. In other embodiments, the light detectors 106 and/or 110 respond to single mode, multimode, single band, and broad band light. The light detectors 106 and 110 may be matched to the light source.

Figure 2B:
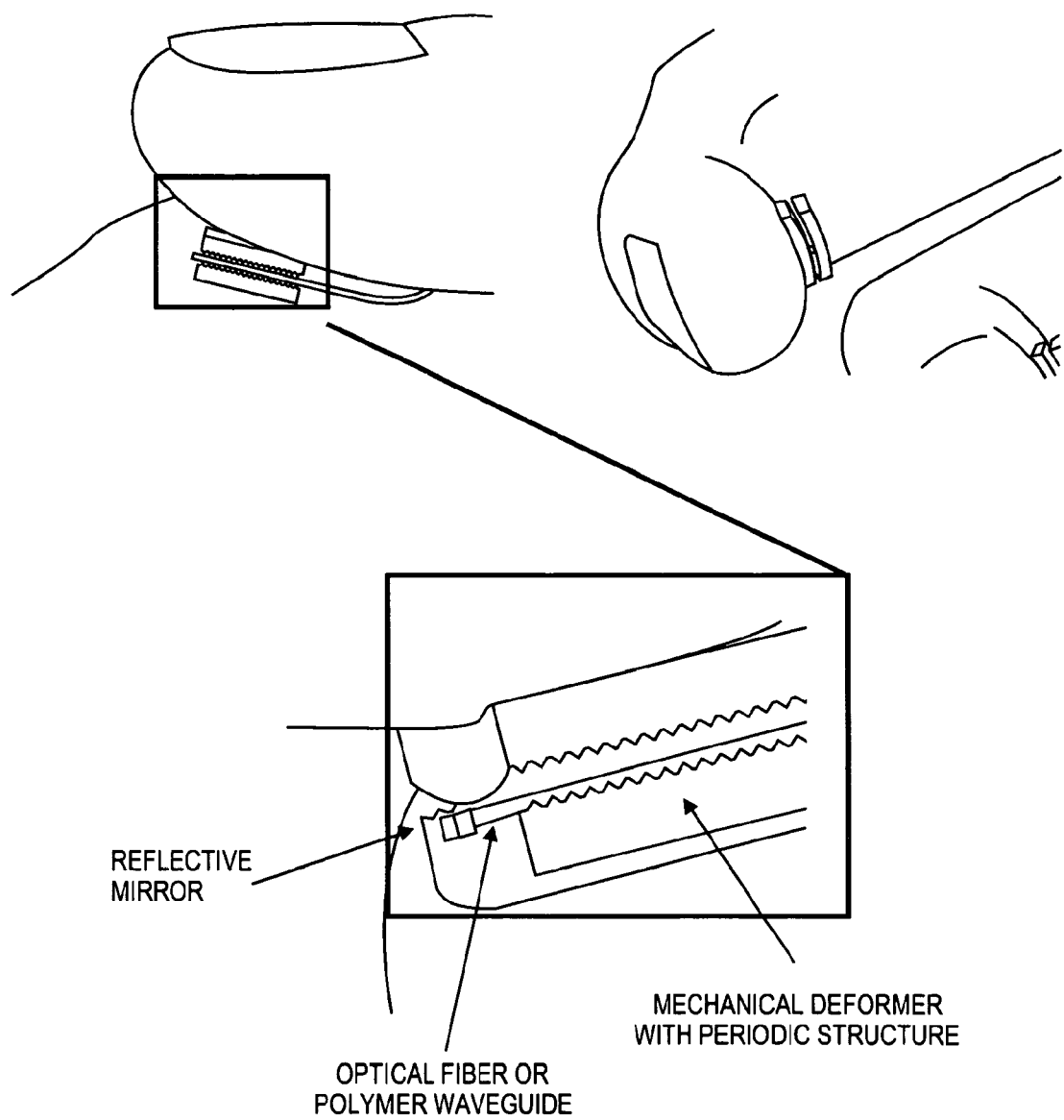
FIG. 2(b) is a view of the clinical sensing glove depicted in FIG. 1 having a mechanical deformer according to an embodiment of the present invention.

FIG. 2(b) is a view of the clinical force sensing glove depicted in FIG. 1 having a mechanical deformer according to an embodiment of the present invention, including an optical fiber or polymer waveguide having a reflective mirror at its tip.

Figure 2C:
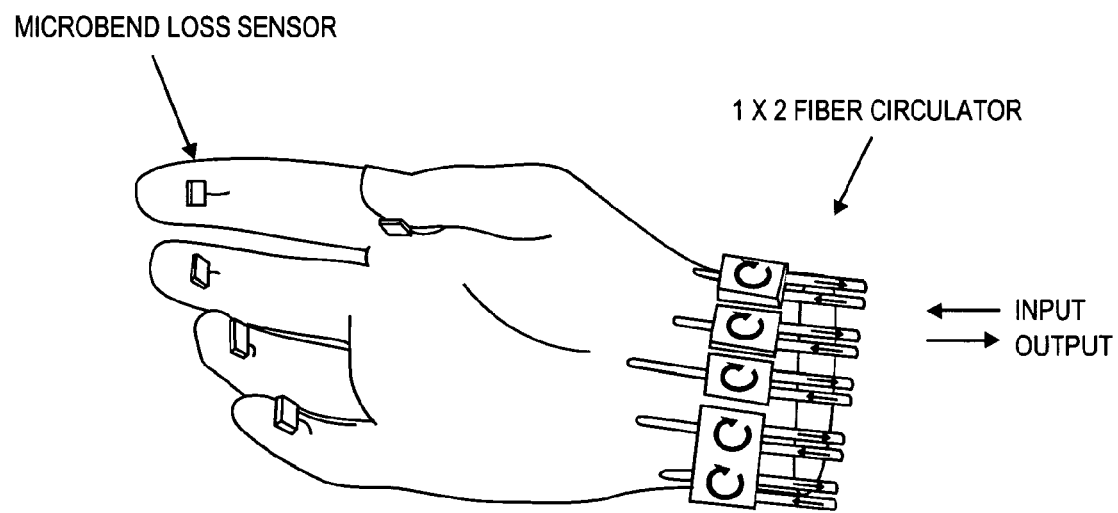
FIG. 2(c) illustrates an optical setup for the clinical sensing glove depicted in FIG. 1 according to an embodiment of the present invention.

FIG. 2(c) illustrates an optical setup for the clinical force sensing glove depicted in FIG. 1 according to an embodiment of the present invention, including micro bend-loss sensors embedded in finger tips and a 1×2 fiber circulator on a wrist portion of the glove.

FIG. 3 is a side view and FIG. 4 is a disassembled of the flexible sensor 104 which includes a flexible force applicator 302, a flexible force applicator 304 having a groove 306 disposed therein, an optical fiber 308 disposed in the groove 306, and an elastomeric polymer 310 disposed on the optical fiber 308 and between the two applicators 302 and 304. The illustrated applicator 302 includes several corrugated teeth 312, 314, 316, and 318. The illustrated applicator 304 includes several corrugated teeth 320, 322, and 324. Of course, the number of corrugated teeth may be increased or lowered without affecting the spirit and intent of embodiments of the invention.

The two applicators 302 and 304 of the flexible force sensor 104 illustrated in FIG. 3 include two thin polymer plates that sandwich the optical fiber 308. The two plates are flexible and custom designed to induce bending in the optical fiber 308 via the series of corrugated teeth 312, 314, 316, 318 320, 322, and 324 inside the plates. The two applicators are initially held together using lips 402 on the edges of the applicator 302. The edges of the applicator 304 fit inside the lips 402 until the applicator 302 and 304 are permanently held in place using the elastomeric polymer 310.

When a force is applied, the applicators 302 and 304 move closer together. The corrugated teeth 312, 314, 316, 318 320, 322, and 324 inside the plates engage the optical fiber 308 and produce micro-bends within the optical fiber 308. Micro-bends in the optical fiber 308 cause light to escape from the optical fiber 308 and thus reduce the light transmitting inside the optical fiber 308. The periodic micro-bends caused by the teeth 312, 314, 316, 318 320, 322, and 324 enhance the bend loss by coupling particular core modes propagating close to the edge of the optical fiber 308 into radiations modes due to the same repeated bends. This fiber optic technique is called micro-bend loss.

Figure 5:
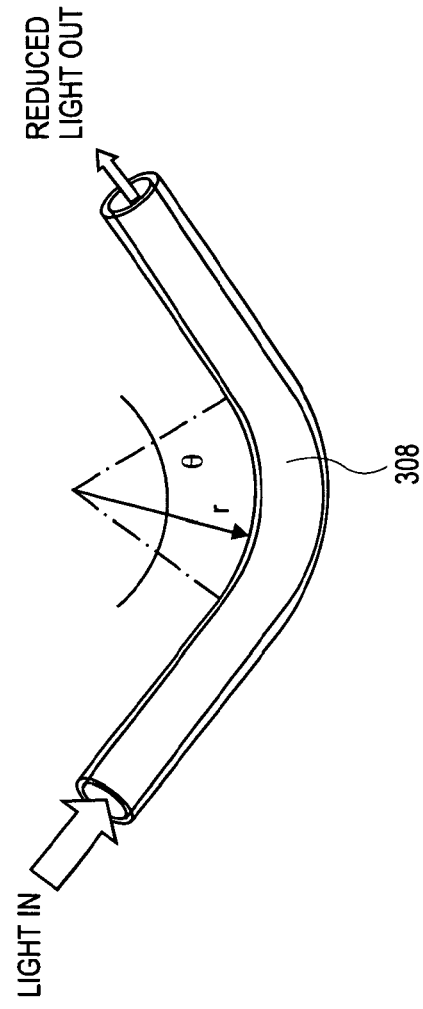
FIG. 5 is a diagram of the bend loss effect in an optical fiber for a micro bend-loss sensor according to an embodiment of the present invention.

FIG. 5 is a diagram of the bend loss effect in the optical fiber 308 according to an embodiment of the present invention. In the illustrated embodiment, the optical fiber 308 is bent about an angle ($\theta$) with a radius (r). The attenuation of light through the optical fiber 308 increases exponentially with the angle ($\theta$) and with a smaller bending radius. The attenuation of light is proportional to the amount of bending the optical fiber 308 experiences; therefore the intensity at the light detector 106 can be used to measure the force across the sensor 104. As a small amount of force is applied to the sensor 104, the teeth 312, 314, 316, 318 320, 322, and 324 minimally engage the optical fiber 308, creating a small light attenuation. A larger force creates greater bending of the optical fiber 308 by the teeth 312, 314, 316, 318 320, 322, and 324 and thus results in a larger light attenuation. In this way, the force applied can be directly related to the light lost—creating a sensor which is electronically inert and highly sensitive to manual forces applied by the hands. A general simplified formula is $L_{total} = A e^{BB-Cr}$, where $L_{total}$ is the total light loss in dB and A, B, and C are constants.

The light loss is due to the optical power coupled between the propagating modes to radiation modes. Some of the radiated light can be confined to the fiber clad and subsequently guided down a fiber as cladding modes. When microbends have a spatial periodicity on the order of the inverse wave number reference between neighboring fiber modes, strong mode coupling occurs. To achieve this strong mode coupling by mechanical means, we can create a mechanical deformer with spatial period of bending $\Lambda$. A displacement (x) of the mechanical deformer changes the amplitude of the fiber microbends which results in an intensity modulation. For pressure sensor, the transmission coefficient for light propagating through the bend fiber changed by the amount of applied pressure is equal to:

$$\Delta T = \frac{\Delta T}{\Delta x} A_p \left( k_f + \frac{E_s A_s}{l_s} \right)^{-1} \Delta P \cong \frac{\Delta T}{\Delta x} A_p k_f^{-1} \Delta P,$$

where $A_p$ is area under the load, $k_f$ is the bent fiber force constant and $A_a$, $E_s$, $l_s$ are cross sectional area, Young's modulus and length of the mechanical deformer. The approximation assumes that the deformer's $A_s E_s / l_s$ is much smaller than the fiber's $k_f$.

For the optical portion of the modulation index $\Delta T/\Delta x$, the loss occurs when the wave number of the spatial distortion is equal to the difference in the wave numbers between the modes. The periodic microbending induced along the fiber axis couples power between modes with longitudinal propagation constant equal to $$\beta_m - \beta_n = \frac{2\pi}{\Lambda},$$

where each mode has propagation constant $\beta_m = n_1 k \cos(\theta_m)$, with $\theta_m$ representing the angle which the mode's equivalent rat makes with the fiber axis, $n_1$ core refractive index, and k is free space propagation constant, $\Lambda$ is the mechanical distortion wavelength. Based on Wentzel-Kramers-Brillouin (WKB) approximation, the distance in $\beta$ space between adjacent guide modes in a fiber is given by $$\delta\beta = \beta_{m+1} - \beta_m = \left(\frac{\alpha}{\alpha+2}\right)^{1/2} \frac{2\sqrt{\Delta}}{r} \left(\frac{m}{M}\right)^{\frac{\alpha-2}{\alpha+2}},$$

where m is the order of modal group and M is total number of modes, $\alpha$ is a constant ($\alpha=2$ for parabolic index fiber, $\alpha=\infty$ for step index fiber), r is the core radius and $\Delta$ is the fractional difference in refractive index between core and cladding $$\Delta = \frac{n_1^2 - n_2^2}{2n_1^2} \cong \frac{n_1 - n_2}{n_1}$$

for $\Delta \ll 1$, where $n_1$ and $n_2$ are refractive indices for core and cladding.

In the case of parabolic index fiber, the equation $$\delta\beta = \beta_{m+1} - \beta_m = \left(\frac{\alpha}{\alpha+2}\right)^{1/2} \frac{2\sqrt{\Delta}}{r} \left(\frac{m}{M}\right)^{\frac{\alpha-2}{\alpha+2}}$$

becomes $$\delta\beta = \frac{\sqrt{2\Delta}}{r}.$$

It shows that $\delta\beta$ is independent of order of mode since all modes are equally spaced in k space (to within WKB approximation). This means that an efficient coupling between modes can be achieved with just one single spatial period. Since numerical aperture is defined as $NA = n_o \sin\theta_o = (n_1^2 - n_2^2)^{0.5} \approx n_1 (2\Delta)^{0.5}$, the spatial period based on the above NA and $\Delta$ is $$\Lambda = \pi r \sqrt{\frac{2}{\Delta}} = \frac{2\pi r n_1}{NA}.$$

In the case of step index, modes are not equally spaced and $$\delta\beta = \frac{2\sqrt{\Delta}}{r} \left(\frac{m}{M}\right).$$

The separation of modes in k space for a step index fiber is therefore dependent on the order of the mode, m. Based on equations $$\beta_m - \beta_n = \frac{2\pi}{\Lambda}$$

and $$\delta\beta = \frac{2\sqrt{\Delta}}{r} \left(\frac{m}{M}\right),$$

we see the larger the m, the smaller Λ while lower order modes require larger period. The spatial period for highest order core modes coupled to radiated modes (assume m=M) is given by $$\Lambda = \frac{\pi r}{\sqrt{\Delta}} \cong \frac{\sqrt{2}\,\pi r n_1}{NA}.$$

The mechanical parameter also affects the outcome of the sensitivity of the sensor. The applied force and the resulted displacement $\Delta x$ are related by simple $\Delta F = k_f \Delta x$. Considering the bent fiber or waveguide as a bar loaded at the center and clamped at its ends $$k_f = \frac{3\pi E_s d^4 \eta}{\Lambda^3},$$

where d is diameter of the fiber and η is the number of bent intervals.

For some embodiments, a parabolic index fiber is used so that only a single spatial period may be required to create efficient coupling between all modes. A mechanical applicator using composite silicone rubber may be used (see FIG. 2(b)). To create a reflective mode detection on the sensor a mirror (thickness >1 of the operating wavelengths) may be deposited on tip of a fiber. This causes the transmitted light to reflect back to the rotator where intensity is redirected to a photodetector (FIG. 2(c)). An LED (an incoherent light source) may be used as an input light source to minimize speckles and lead noise. Multimode fiber may be used to both increase bend-loss and to reduce the light coupling losses at both input and output ends. Each fiber's coating may also need to be carefully selected to decrease the macrobend effect. There is an effect that causes higher order modes to leak to the coating which can in turn introduce additional losses and significantly reduce the microbend effect at higher order modes; therefore it must be avoided. The sensor's length may also be optimized to maximum the microbend effect.

The mechanical applicator and waveguide may be made from PDMS, a flexible elastomer using soft lithography techniques. PDMS is a widely available, clean room compatible and a physically and chemically stable silicone rubber with a wide range of applications. Sylgard 184 silicone elastomer from Dow-Corning Corporation is among the most commonly used PDMS elastomers. The primary advantages of PDMS are that it bonds easily and has very good optical properties such as high transparency, low loss and, most importantly, a refractive index (n=1.43) that closely matches the indices of commercially available optical fibers. Some physical and chemical attributes of PDMS are, as compared to other polymers, a unique flexibility (shear modulus G between 100 kPa and 3 MPa), low durometer hardness (Shore A 40), very low loss tangent (tan δ<<0.001), high gas permeability, low temperature variation, and it is virtually inert to most chemicals and essentially non-toxic in nature. The primary use for this material is usually to provide an elastomeric stamp or mold for soft lithography. However, due to its unique optical and physical properties and low surface energy (~21.6 dyn/cm), this material allows replicas to be separated from their molds easily; therefore it is the material of choice for the proposed optical microbend sensor.

For the mechanical deformer and the rest of the packaging, molds may be constructed that include features for holding a fiber or waveguide and a mechanical applicator. The molds may be made out of SU-8 photoresist (MicroChem Corporation XP SU-8 2000 series, Newton, Mass.) on a silicon wafer where large aspect ratio micro-structures can be faithfully reproduced. The patterns may be formed on SU-8 simply by exposing it with the desired patterns using typical photolithography. Once the molds are created, the substrate containing the optical waveguide may be placed inside an aluminum container with the waveguide or fiber holder mold, where it may be filled with PDMS to form a waveguide or holder for the fiber. The same molding process may be applied to construct the mechanical deformer. Since we want to create a stiffer area on the diaphragm, a second layer of polymer material may be added onto the diaphragm using the same molding process. Later an oxygen plasma treatment may be done on all the substrates before bonding them together to form the final structure.

After the fiber sensors or waveguide sensor are completed, the sensors may be mounted onto a mannequin hand. We may provide different hand sizes for different operators. First we may immerse the hand into a liquid latex solution or desired polymer glove material to form a layer of support structure then sensors are put on top of the layer. Finally, the entire hand is immersed into the liquid latex again to seal the sensors into a latex structure.

With FIGS. 1-5 in mind, note that the light source 108 is attached to the glove 102 and powered by the wrist cuff 112. The light source 108 drives all of the glove 102 sensors 104 disposed at each thumb portion 202, finger tip portion, 204, 206, 208, and 210, and the palms portions 212, 214, 216, and 218. The light emitted from the light source 108 passes to each sensor 104 in the glove-embedded polymer optical fiber 308. At the sensor 104, the light is either passed or attenuated if force is applied to the sensor 104. The light is then harvested by the light detector 106 on the wrist cuff 112, which supplies a voltage output proportional to the light detected and translated into a value. The light source 108 at one end of the optical fiber 308 may be paired with the light detector 106 at the other end of the optical fiber 308 to have the same wavelength for optimal signal detection.

The value for the detected optical signal may be transmitted by the wrist cuff 112 to the display and control module 120, where calibration is performed, translating the force at the hand into a meaningful measurement reported to the clinician. Additionally, the display and control module 120 may include settings for glove 102 calibration, enabling the setting of the force threshold warning 220, and for the session to be recorded for review (reference number 222). These features make the clinical force sensing system 100 easy to use and adopt in practice as well as practical for many applications.

For some embodiments, factors such as changing temperature and tissue stiffness were evaluated and static and dynamic calibration was performed. In embodiments in which a single sensor 104 index finger-tip prototype of the glove 102 was implemented, the single sensor 104 provided a range from 0.03 to 80 N with a resolution of 0.01 N. The sensor was sandwiched between a load applicator and load cell wherein the forces across the sensor 104 and the light lost were recorded. This calibration was performed statically and exhibited hysteresis with a maximum error of 4N. The dynamic calibration of the sensor 104 demonstrated faithful responses up to a maximum loading rate of 100 N/sec. The static and dynamic curves were indistinguishable below this rate.

Beyond these calibrations, the sensitivity of the sensor 104 to tissue stiffness and temperature was investigated. These tests were not exhaustive but evaluated 10-degree differences in sensor 104 temperature and found the data output insensitive to temperature.

Furthermore, the sensor 104 was evaluated with soft tissues, foams, and aluminum boundary conditions. In each of these cases, the sensor 104 performed to the static calibration; however, on aluminum its range was diminished by 70%. Because the sensor 104 was designed for softer tissues, it was not unexpected that its performance would suffer on a rigid surface.

Figure 6:
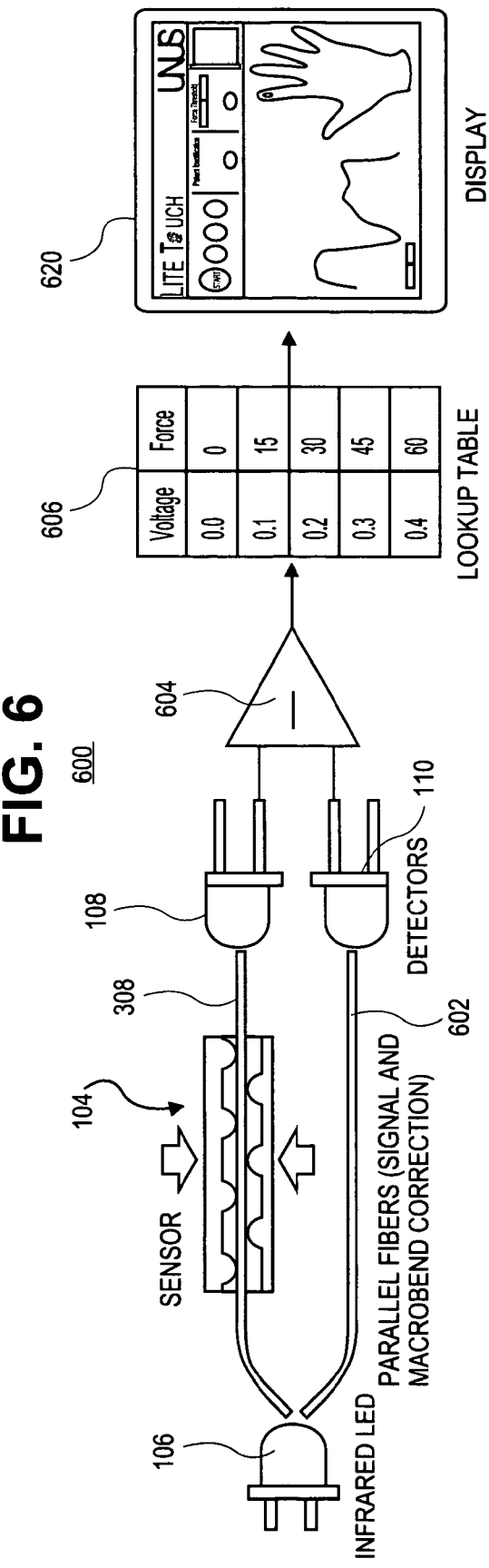
FIG. 6 is a schematic diagram illustrating a calibration setup for a clinical force sensing glove having a micro bend-loss sensor according to an embodiment of the present invention.

FIG. 6 is a schematic diagram illustrating a calibration setup 600 according to an embodiment of the present invention. In the illustrated embodiment, the calibration setup 600 includes the light source 106 operationally coupled to the optical fiber 308, which forms part of the sensor 104. The optical fiber 308 is operationally coupled at the other end to the light detector 108. The light source 106 also is operationally coupled to one end of a set of parallel optical fibers 602, one of which is for macro-bend correction and the other of which is for signal correction. The parallel optical fibers 602 are coupled with the same light source 106 and a different light detector 110 to create a control channel against which to measure intensity loss. The other end of the optical fiber 602 is operationally coupled to the light detector(s) 110. The light detectors 108 and 110 are operationally coupled to an amplifier 604, which is operationally coupled to a lookup table 606. The lookup table 606 is operationally coupled to a control and display module 620. Optical fibers 602 do not pass through the sensor 104 and thus light intensity in the optical fibers 602 is not attenuated by force applied across the sensor 104. The control channel also serves to correct for other perturbations the optical fibers may experience such as bending with the finger when on the glove platform or vibrations or external light sources.

To calibrate the force sensor 104, a pre-calibrated load cell may be used as a reference. The force sensor 104 may be pressed against the load cell up to its maximum rated load and the force is recorded with the light intensity lost between the two parallel fibers 308 and 602. This creates a force vs. intensity relationship that can be used to measure force from the intensity output of the sensor 104. The calibration curve is monotonic up to its maximum range.

For some embodiments, many features may be implemented in software. For example, a calibration algorithm may be provided. Using the calibration algorithm, the lookup table 606 is generated from the calibration load cell. The incoming voltage signal from the light detectors 108 and 110 is interpolated in the lookup table 606 to calculate the force. Dynamic software may smooth the signal with a moving average filter. The noise level of the signal may be continuously monitored and the width of the moving average filter altered to maximize the responsiveness of the sensor 104 while minimizing the noise level. When excessive noise is in the detected signal, the width of the moving average filter is increased; when the noise level is low, the width of the moving average filter is decreased.

Some embodiments may have an automatic pause feature. In clinical applications, to prevent unnecessary data collection, acquisition may be suspended when the signal is quiescent for a specified period of time. A button on the wrist cuff 112 or in another user interface may restart the data collection.

Some embodiments may have an auto-zero feature. When the received signal is quiescent for a specified duration, the software may automatically re-zero the input to adjust for drift.

Other embodiments may have a feature for inputting comments. For example, in the clinical application, comments can be added to the data set associated with any feature of the data.

A peak detection feature may be available in alternative embodiments. For instance, software also may include a peak finding algorithm to detect maximum loads applied during tests or sessions, or to determine loading rates such as in pulse rate.

Some embodiments may enable recording of a session. Records may be kept either online in a secure network drive or on a local hard drive filed by patient number. Alternatively, audio recordings may be taken to supplement force data.

The control and display module 620 (shown in more detail in FIG. 2 as control and display module 120) includes a graphical display. A chart 122 may be displayed with a time scale that shows the time history of the force that is applied across the sensor 104. For systems with multiple sensors 104, a numerical readout may be provided along with different colors for each channel. A color box may display relative force and the threshold alarm. A threshold 210 can be set that may display a warning color when the threshold force has been surpassed.

The control and display module 620 also may include an audible alarm. The threshold 210 can be set that may sound an audible alarm when the threshold force has been surpassed. The audible alarm may be frequency controlled so that as force continues to increase the pitch of the alarm also increases.

The control and display module 620 may be customized. For example, the display mode can be customized for any treatment type or practice dependent on a user's needs and preferences.

Figure 7:
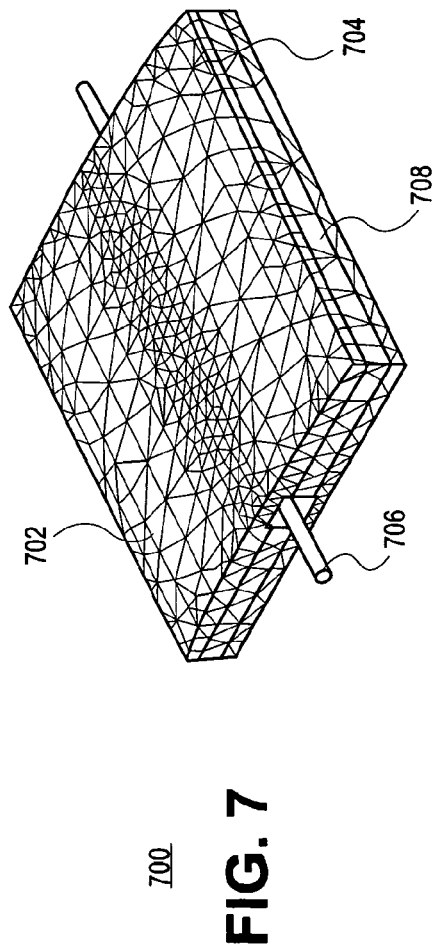
FIG. 7 illustrates a model of a micro bend-loss sensor according to an embodiment of the present invention.

To test the concept a system implemented in accordance with the clinical force sensing glove system 100, a fiber-optic sensor was first modeled in ANSYS engineering simulation software to determine necessary tooth spacing and height for adequate fiber bending. FIG. 7 illustrates a model 700 according to an embodiment of the present invention. The model 700 includes a mesh of a finite element sensor for analysis of displacement under linear loading. Two outside polymer applicators 702 and 704 were given the material properties of ABS plastic and the inside elastic material 708 was modeled as polydimethylsiloxane (PDMS). An optical fiber 706 was modeled as poly(methyl methacrylate) (PMMA). The sensor was 7 mm long, 7 mm wide, and 1.2 mm thick and the optical fiber 706 had a diameter of 250 μm. The teeth were spaced 1.8 mm apart and were 0.25 mm tall. 100 N was applied to the top surface and the displacement of the teeth was measured as a function of load. This displacement data was used to calculate the angle and radius about which the optical fiber 706 was bent, which could then be used to estimate an expected attenuation curve.

The sensor was then modeled in SolidWorks computer-aided design (CAD) software with the optimized tooth spacing and heights from the finite element analysis. Seven alternating teeth were included in the sensor, four on the top applicator 702 and three on the bottom applicator 704. The exterior surfaces were contoured to minimize sharp edges that might be felt by the clinician. The bottom applicator also included a groove for the optical fiber 706 to be placed into during fabrication for stability and protection. The top applicator 702 has a lip on each side to help secure it, aligned correctly on the bottom applicator 704 during fabrication.

The teeth are separated by 1.8 mm, are 0.25 mm high, and have a radius of curvature of 0.40 mm. Each applicator 702 and 704 was kept above 0.1 mm thick for structural integrity. A cavity was included between the applicators for the layer 708 of elastomeric polymer (PDMS) that would provide linear displacement when loaded.

Figure 8:
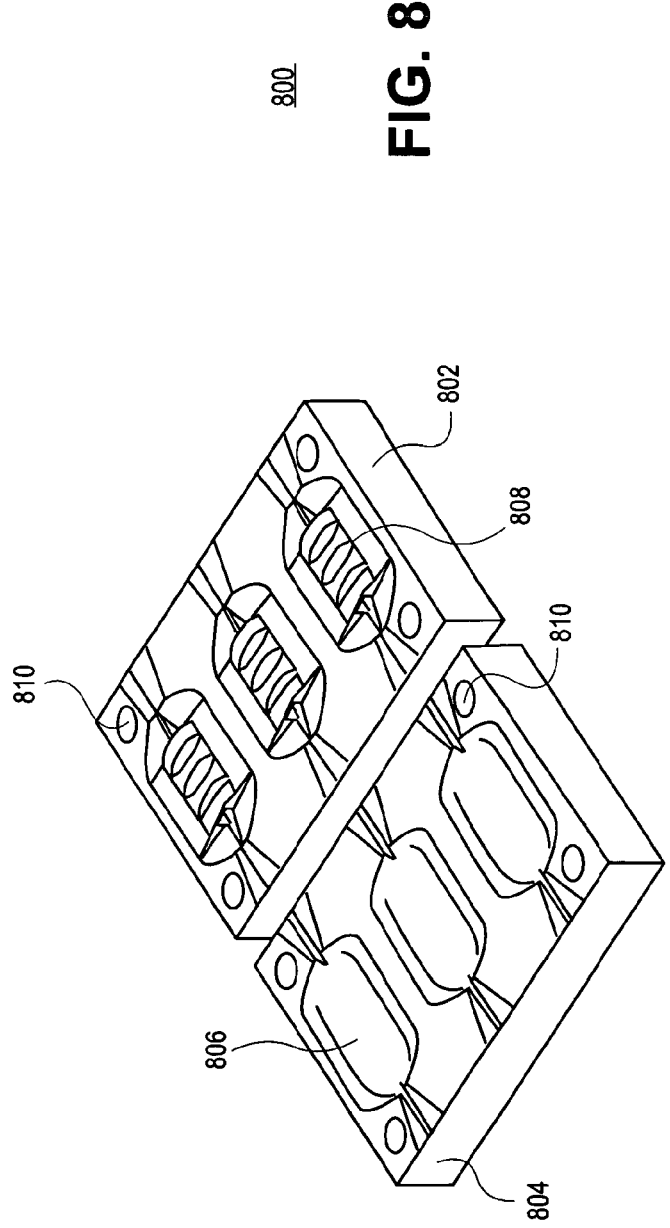
FIG. 8 illustrates a top mold and a bottom mold for making a micro bend-loss sensor according to an embodiment of the present invention.

The sensor was then converted into molds for the top and bottom applicators 702 and 704. FIG. 8 illustrates top mold 802 and bottom mold 804 according to an embodiment of the present invention. Each mold 802 and 804 includes cavities 806 or 808 for three sensors to be cast simultaneously. The molds 802 and 804 include through holes 810 for bolts to hold the two molds 802 and 804 together. The molds 802 and 804 were printed on a rapid prototype machine by RedEye Rapid Prototyping, located in Eden Prairie, Minn., and sanded for smoothness. After spraying with mold release, a 2-part liquid polyurethane plastic was spread into the cavities 806 and 808 from both plates in the molding block. The two plates were pressed together and secured with bolts. The liquid plastic was allowed to cure for one hour before de-molding.

Referring back to FIG. 4, after the applicators/plates have been formed the optical fiber 308, in one embodiment having a length of approximately 0.5 m length, was cleaved and centered on the bottom applicator 304, lying in the groove 306. Liquid PDMS was degassed for 30 minutes and poured over the optical fiber 308 into the cavity in the bottom applicator 304 and the top applicator 302 was centered and laid over the PDMS. Of course, although PDMS was chosen in this case, other elastomers may be suitable. The composition of the elastomeric layer affects the sensitivity and range of the sensor 104. A stiffer elastomer increases the range while a softer elastomer increases the sensitivity. The assembled sensor 104 was taped to a flat surface to keep all components together and cured overnight. After full cure, the tape was removed and the sensor 104 was ready for embedding in the glove 102.

Smooth-Cast 300 from Smooth-On, Inc., located in Easton, Pa., was used for the applicators. Smooth-Cast 300 is a two-part polyurethane that cures virtually bubble free at atmospheric pressure in 1 hour. It has a Shore D hardness of 70. The PDMS elastomer layer used was Sylgard 184 from Dow Corning, located in Midland, Mich. Smooth-Cast 300 has excellent durability over time, which is suitable for consistent force measurements in the sensor 104 over long clinical sessions.

The optical fiber used is a 250 µm polymer fiber from Paradigm Optics, located in Vancouver, Wash. The polymer fiber was chosen because of its durability when compared to glass fiber which cracks or shatters when large loads are applied. This polymer fiber bends elastically when loaded and has a large core which is beneficial for collecting light from a light emitting diode (LED) or other suitable light detector. Its PMMA core is 240 µm and cladding is fluorinated polymer. This optical fiber also cleaves easily with a hot razor blade. Of course, other optical fibers are suitable as well, such as glass optical fibers. Polymer waveguides may also be suitable.

A signal is generated by transmitting light from a light source through the optical fiber 308 and measuring the relative intensity after it passes through the optical fiber 308 between the applicators 302 and 304. An infrared (centered at 940 nm) LED light source was used to limit ambient light noise in the signal. The 3 mm LEDs used from LiteOn Technology Corporation (LTE-4206), located in Fremont, Calif., have a radiant intensity of 2.71 mW at 20 mA. The photodetector paired with this light source was another T-1 packaged 940 nm peak phototransistor (LTR-4206E). The dome on the LED focuses the light into the front 20° and the phototransistor also has a half angle of 20°. The LED supplies light to two parallel fibers per sensor.

Referring back to FIG. 6, one optical fiber 308 passes between the applicators 302 and 304, and the other optical fiber 602 serves as a macro-bend correction signal that eliminates the noise generated when the finger or wrist is bent. To couple the optical fibers 308 and 602 to the optical components light source 106 and light detectors 108 and 110, the cleaved ends of the optical fibers 308 and 602 were inserted into a 5 mm length of 0.6 mm outside diameter wire jacket. This was secured to the light detectors 108 and 110, and light source 106 with shrink wrap tubing and epoxied together. The light source 106, and light detectors 108 and 110 were wired to a 4-channel plug (light source 106 supply, ground, and the two light detectors 108 and 110 output channels) that connected to a printed circuit board (PCB) housed in the wrist cuff 112 (see FIG. 1). Another 4-channel plug was connected to the other side of the PCB to be connected to the display module 520. The PCB includes simple circuitry to indicate power connection, glove 102 connection, drive the light source 106, and collect the light detectors 108 and 110 signals to send to the display module 520.

To embed the optical fibers 308 and 602, the light source 106, and light detectors 108 and 110, and the sensor 104 within the glove 102, an off-the-shelf clinical glove was turned inside-out and inflated and the components were secured with small strips of elastic tape from 3M, located in St. Paul, Minn. The optical fiber 308 was secured along the back of the hand and along the sides of the pointer finger, crossing over the ball of the fingertip where the sensor 104 was placed. In this way, the optical fiber 308 would not be stretched when the finger was bent. The macro-bend correction optical fiber 602 was secured to the back of the finger instead of the fingertip to avoid being crushed. The light source 106, and light detectors 108 and 110 were taped to the glove 102 on the back of the hand with the connection wires extending out past the wrist for connecting to the wrist cuff 112. The glove 102 was then turned back inside-out so the fibers 308 and 306, sensor 104, and the light source 106, and light detectors 108 and 110 were housed inside.

In an alternative embodiment, if using pre-made gloves, the sensor 104 can be embedded into the pre-made clinical gloves. The sensor 104 with fibers 308 and 602 are secured onto a strip of latex, nitrile, or polystyrene (dependent on the glove type), and the strip is adhered onto the glove 102 with an elastic adhesive sealant. The sensor 104 is placed over the fingertip or on the palm in a location that is clinically useful. The optical fibers 308 and 602 are placed along the sides of the fingers to prevent pulling when the finger is bent.

Alternatively still, the optical fibers 308 and 602, and sensor 104 may be embedded during a glove dipping process. For example, a glove mold may be dipped into liquid latex, nitrile, or polystyrene and allowed to dry partially. The sensor 104 and fibers 308 and 602 are secured onto the first layer. The glove is then dipped again, embedding the sensor 104 and fibers 308 and 602 between layers of glove polymer.

Figure 13:
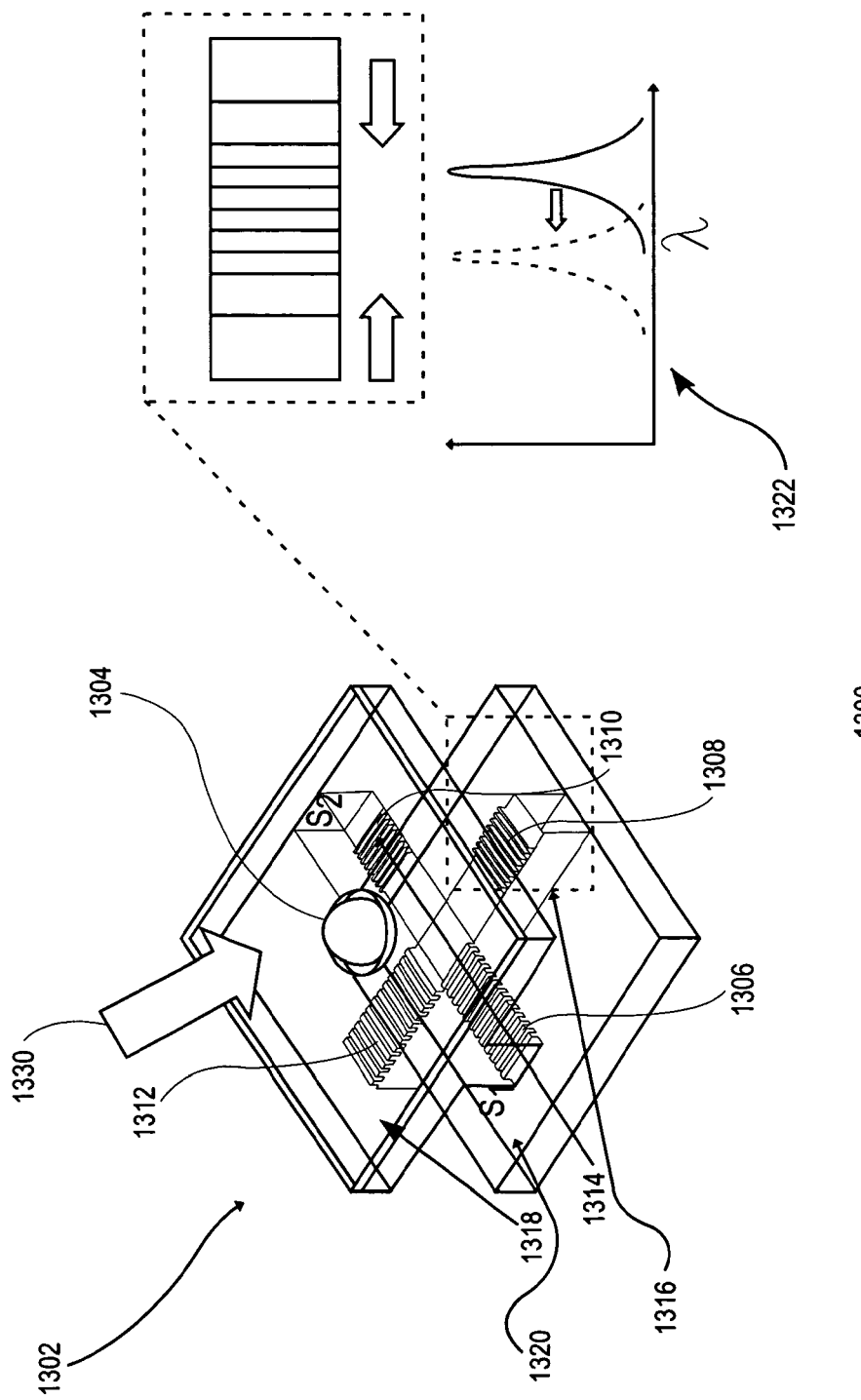
FIG. 13 illustrates a grating-based sensor for a clinical sensing according to an embodiment of the present invention.

For some embodiments, the wrist cuff 112 may be a unit shaped similarly to a watch. FIG. 13 illustrates a wrist cuff 112 according to an embodiment of the present invention. The wrist cuff 112 includes circuitry for driving the light source 106, collecting signals from the light detectors 108 and 110, amplifying the signal (amplifier 604), converting analog to digital, indicating conditions on the wrist cuff 112, transmitting the data wirelessly to the control and display unit 620, and housing a rechargeable battery.

The electronics may include custom circuitry for driving the light source 106, circuitry for collecting the intensity output from the light detectors 108 and 110, LED lights to indicate when the wireless connection is active, when the wrist cuff is powered, when the glove 102 is connected, and when the battery is charging.

In this embodiment, the signal from the light detectors 108 and/or 110 is amplified and filtered, the signal is then converted from analog to digital, and transmitted from a wireless transmitter to the control and display module 620 or to a personal computer (not shown).

For some embodiments, a rechargeable battery is used to power the wrist cuff 112 components. A recharging connector may use the same receptacle as photo-coupling plug depicted in FIG. 12.

The wireless transmitter may be a low profile wireless module is used to transmit to the control and display module 520. The wireless transmitter may receive play and pause data, and the force data to display on the wrist cuff 112. The wireless transmitter also may send signals from buttons on the wrist cuff 112 and the force data. The wireless transmitter may be coupled with the control and display module 520 or personal computer to prevent data from being visible by other devices.

The wrist cuff 112 also may include an onboard liquid crystal display (LCD) screen. In this embodiment, the force is displayed on the face of the wrist cuff 112. The wrist cuff 112 also may include a PAUSE/PLAY button to control the control and display module 520.

A custom LabVIEW interface, available from National Instruments, located in Austin Tex., was developed to display and record the force measured by the sensor 104. The sensor 104 may be calibrated before every use to compensate for variability in fabrication and variability among users' fingertips. Thus, the first process is to apply the expected maximal load to an external compression load cell, such as an FC22 available from Measurement Specialties located in Hampton, Va., also connected to the control and display module 620. This generates a calibration curve that correlates force and voltage from the light detectors 108 and 110 (the difference between the sensor 104 and macro-bend correction channels 602), which is proportional to the light attenuation. The calibration curve is verified to be monotonically increasing so that every voltage input has exactly one force output and is subsequently saved in a lookup table 606. The voltage inputs are acquired at a 20 Hz sampling rate, subtracted, and linearly interpolated in the lookup table 606 to calculate the force applied across the sensor 104. A moving average filter may be applied with variable width that is automatically adjusted with periodic noise measurements on the signal.

Several properties of the sensor 104 may be clinically relevant and were tested manually. Force threshold here is defined as the minimum force applied to the sensor 104 that can be detected in the control and display module 620 and may be used for delicate measurements such as pulse readings for cardiovascular practices. Range is the maximum force for which a monotonic calibration curve is still obtained. Threshold and range were measured with manual application of the sensor onto the calibration load cell up to its maximum force at approximately 5 N/s. Resolution is the smallest difference between two forces that can be differentiated by the sensor 104 and was calculated from the analog to digital conversion over the range of input voltages from the light detectors 108 and 110. Accuracy and stability were observed when loaded up to 24.8 N in displacement control and held for 30 seconds. Resolution and accuracy were measured on a linear vertical loading stage UTM1000P.1, available from Newport Corporation located in Irvine, Calif., controlled by a universal motion controller/driver ESP300, also available from Newport Corporation. Noise due to finger bending and hand movement was also measured.

Figure 9:
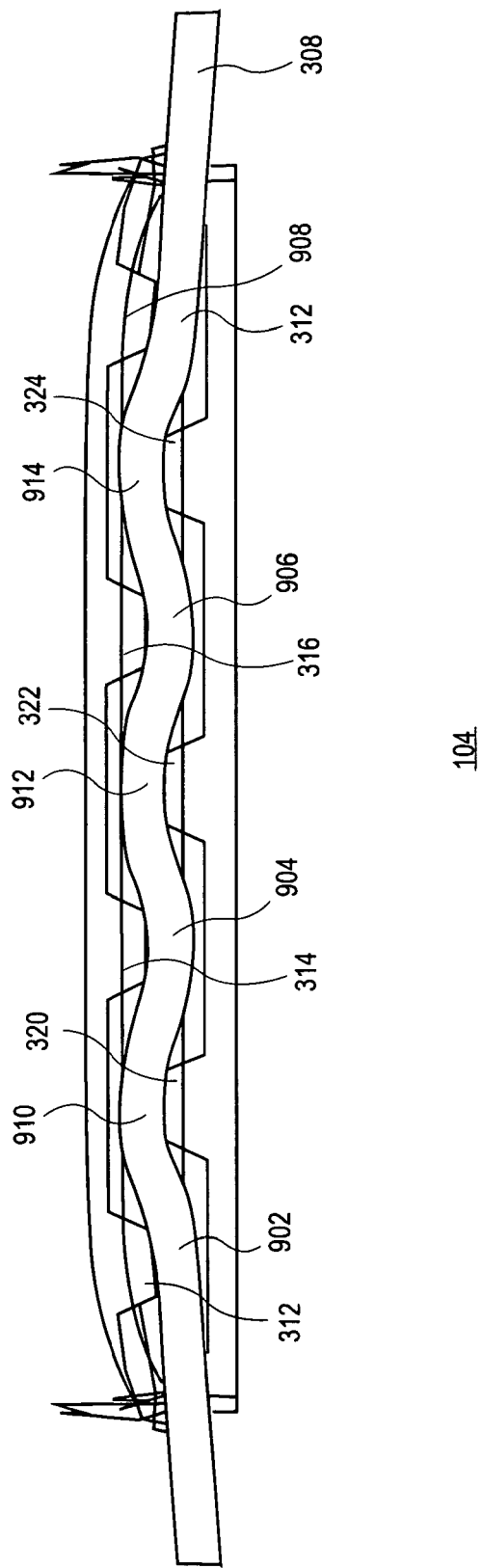
FIG. 9 is a cross-section of a loaded micro bend-loss sensor from a finite element analysis showing periodic perturbations of the optical fiber in the sensor according to an embodiment of the present invention.

The finite element analysis revealed that the deformation of the sensor 104 along the z-axis is linear with respect to the load, deforming 0.1 mm at 100 N. Under this load, the optical fiber 308 bends along a periodic path in 7 corrugations as seen in FIG. 9. The angle and radius of curvature about which the optical fiber 308 was bent were also measured. The total angle around all 7 bends 902, 904, 906, 908, 910, 912, and 914 increases linearly with deformation and the radius of curvature decreases as 1/r. When substituted into the loss formula $$\Delta T = \frac{\Delta T}{\Delta x} A_p \left( k_f + \frac{E_s A_s}{l_s} \right)^{-1} \Delta P \cong \frac{\Delta T}{\Delta x} A_p k_f^{-1} \Delta P$$

and rearranged for measuring the voltage loss due to perturbation, the loss equation can be described as $\Delta V = 10^{\alpha \times g^{\beta F = \gamma/F}} - 1$, where $\Delta V$ is the voltage difference, F is force applied, and $\alpha$, $\beta$, and $\gamma$ are constants.

The sensor 104, when assembled, may measure 1.0 mm thick with a footprint of 7 by 10 mm (FIG. 7). The top applicator 302 interlocks with the bottom applicator 304, holding the optical fiber 308 securely and aligning the teeth 312, 314, 316, 318 320, 322, and 324 correctly. The contours of the top and bottom surfaces of the sensor 104 allow the sensor 104 to fit comfortably on the fingertip and/or palm. Even when large forces are applied the sensor 104 does not cause discomfort to clinician or patient.

Figure 10:
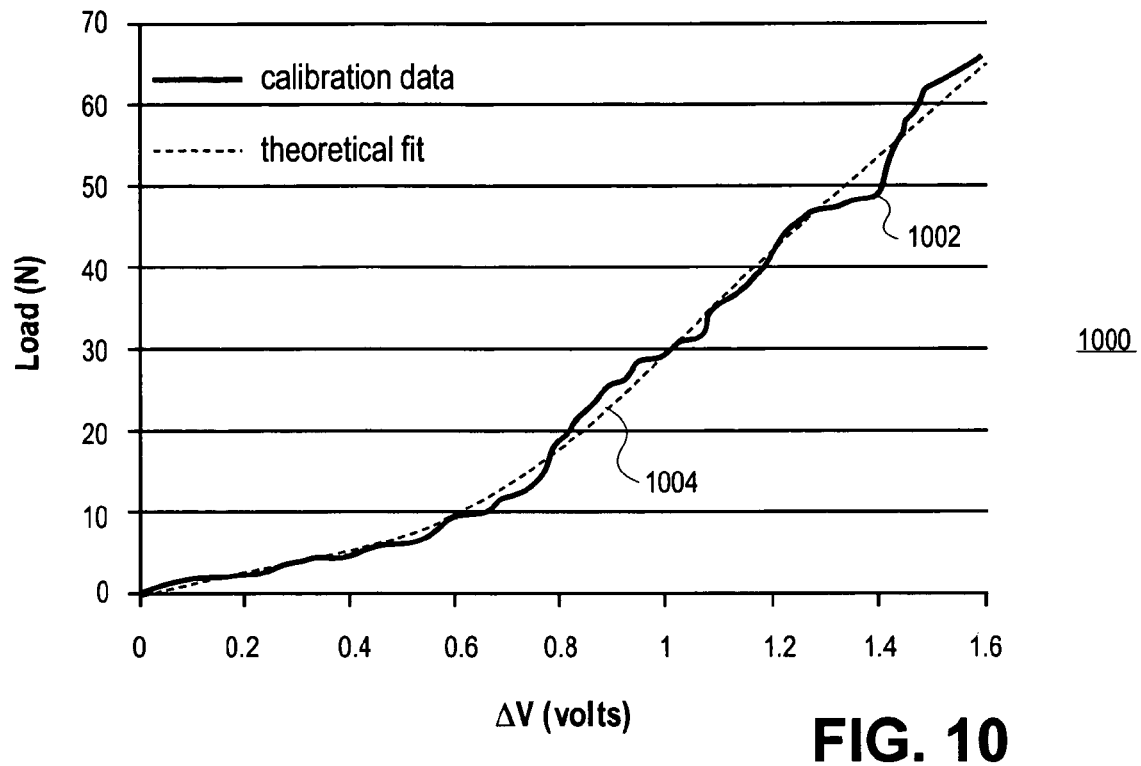
FIG. 10 is a graphical representation of a calibration curve and a theoretical model curve for a micro bend-loss sensor according to an embodiment of the present invention.

When calibrated up to 68 N (15 lbs), the sensor 104 demonstrated strong agreement with expected results based on Equation (2) from finite element analysis and typical optical fiber bending response. FIG. 10 is a graphical representation 1000 of a typical calibration curve 1002 and a theoretical model curve 1004, demonstrating good agreement. The coefficients for the theoretical fit for this specific calibration curve are $\alpha = 0.28$, $\beta = 0.0070$, and $\gamma = 3.96$. The LED and phototransistor PCB used onboard the wrist cuff 112 may use only 83.5 mW and may generate a 1.6 V signal when 68 N are applied to the sensor 104.

Three prototype gloves 102 were tested briefly before being evaluated by clinicians in a physical therapy setting. Initial results have demonstrated that loads up to 90 N can be applied to the sensor 104 while obtaining a monotonic load-loss curve, that is, a functional calibration curve is generated for measuring force through the sensor 104. Loads above 90 N on a fingertip sensor have been difficult to obtain because of a lack of finger strength. Average force threshold has been measured at 0.19 N and average sensor resolution is 0.05 N.

The whole glove system 100 proved to provide a stable force measurement over time and with tolerable noise in the signal. With no movement, the signal-to-noise ratio (SNR) of the system has averaged 56 dB. When the glove 102 was rolled from the fingertip to measure finger bending noise, the SNR decreased to 20 dB, but displaying only 2.7 N (0.6 lbs) increase in the force measured. Environmental light had little effect on the force measurement with an average SNR of 33 dB, contributing to a maximum force measurement artifact of 0.6 N (0.13 lbs).

Figure 11:
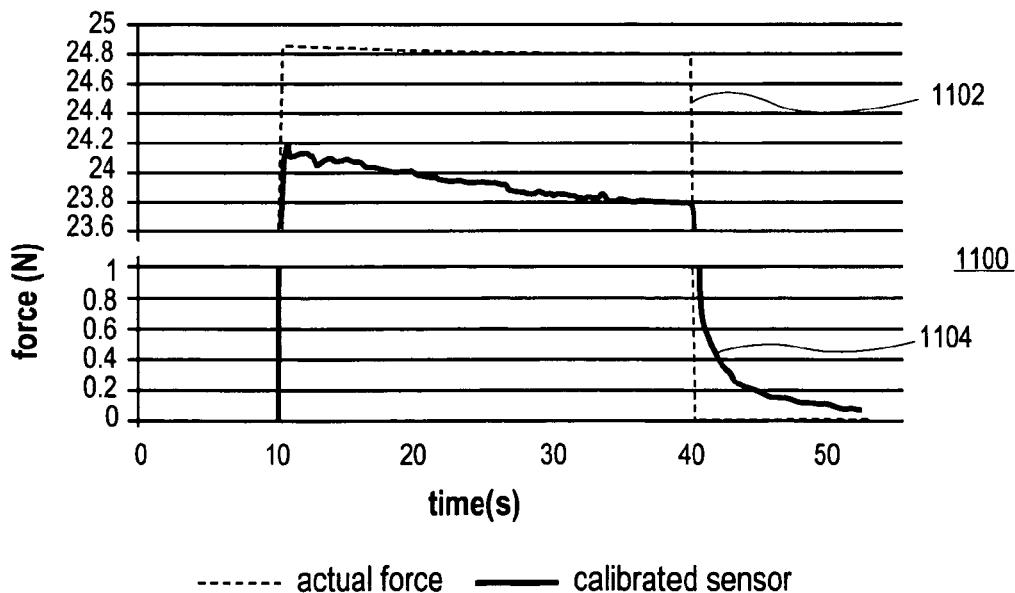
FIG. 11 is a graphical representation showing actual force measured and a calibrated sensor for a micro bend-loss sensor according to an embodiment of the present invention.

When loaded to 24.8 N at 2.4 mm/sec and held in displacement control for 30 seconds, the sensor 104 demonstrated negligible delay and low overshoot. FIG. 11 is a graphical representation 1100 showing actual force measured (graph 1102) and a calibrated sensor (1104). It initially measured 24.2 N, within the acceptable range of 1 N accuracy, and slowly drifted to just below 23.8 N over the 30 second loading duration. At the end of the test, the load cell placed under the sensor had relaxed minimally and the sensor had relaxed to measure about 1.02 N below the actual load. This is just outside the 1 N accuracy criterion. During unloading, the sensor's response was again fast and the delay was negligible until about 1 N, below which it demonstrated an exponential decay back to 0 N.

A feature that sets this sensor 104 apart from other available force sensors is its low cost. Made from inexpensive off-the-shelf materials and requiring little manual labor to assemble, the glove 102 can be made fully disposable. This may allow clinicians to remove them quickly without concern that they might be damaged in the process. Cleanliness in the clinical setting is also preserved as patients may not be handled with a reused pair of gloves 102.

For some embodiments, the light source 104 and the optical fiber 308 can be permanently coupled with sleeves that center the optical fiber 308 radially with respect to the source and optimize the distance from light source 104 to the optical fiber 308. Epoxy may be used to secure the light source 104 and the optical fiber 308. The optical fiber 308 can be permanently coupled with the light detector 106 in the same way. The light source 104 and light detector 106 may be connected to driving and collecting circuits with a connector so they can be easily removed in disposable applications.

Figure 12:
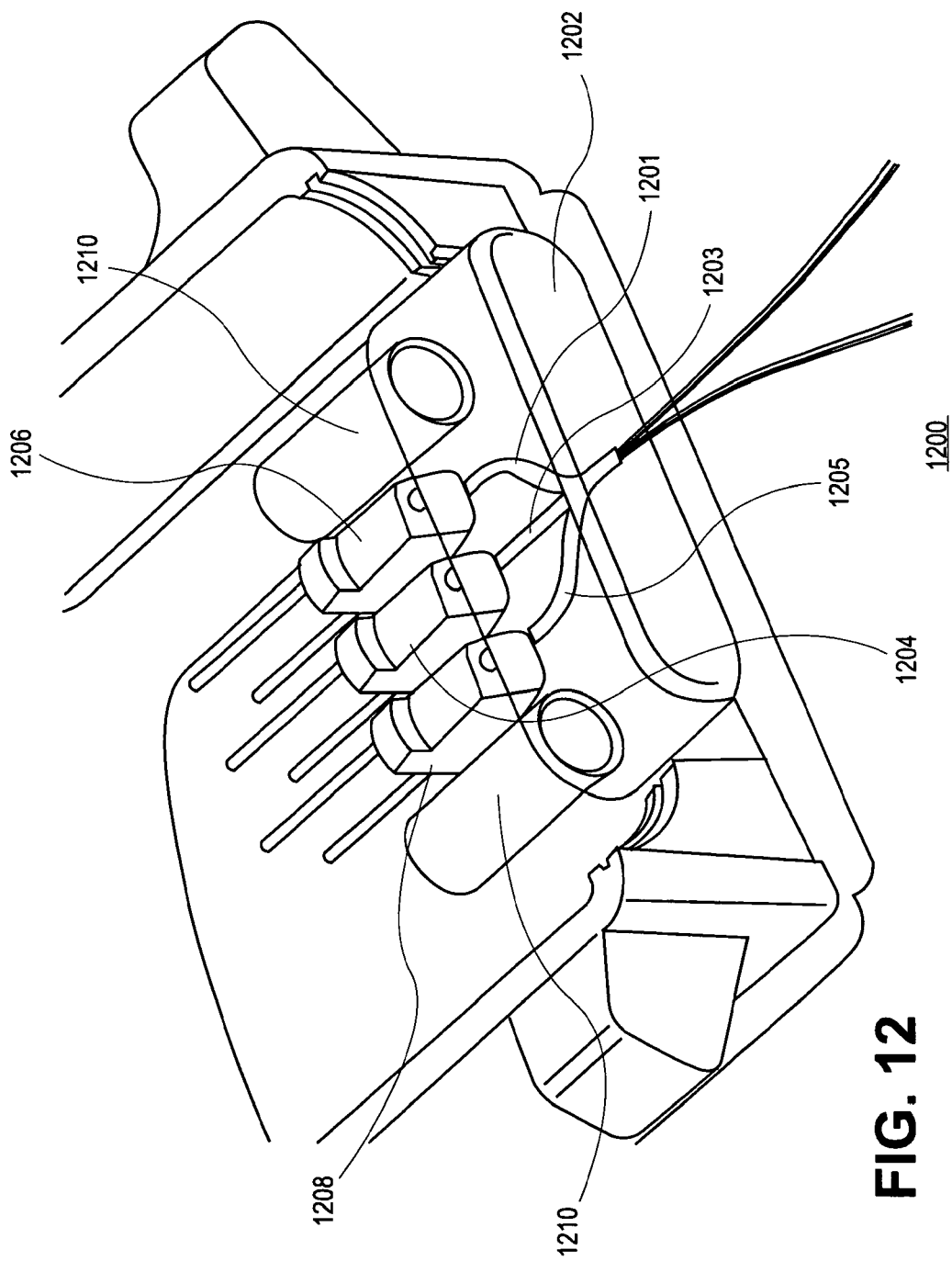
FIG. 12 illustrates a magnetic optical coupling connector for a micro bend-loss sensor according to an embodiment of the present invention.

In alternative embodiments, the optical fibers are held in alignment with the light source and light detectors through a non-permanent connector. The fibers may be secured in a plastic plug that centers the fibers with the source and detector axially. The plug is brought against the light source and light detector in a receptacle, creating good coupling and a strong signal. Magnets may hold the plug in place and helps with aligning the fibers with the source and detector. The magnet makes connecting and disconnecting the optical fiber with the optical components (light detectors and light source) fast and easy. FIG. 12 illustrates a magnetic optical coupling connector 1200 according to an embodiment of the present invention. The plug 1202 is translucent to show the path of the optical fibers 1201, 1203, and 1205 inside. The light source in this case is the clear LED 1204, and the detectors 1206 and 1208 are black. Two cylindrical magnets 1210 flank the optical components to hold the plug 1202 in place.

Alternatively still, a mechanical fit plug connector may be used. It implementation may be similar to that of the magnetic connector but, for security, without the magnets. A tight fit or a snapping mechanism holds the plug in the receptacle and aligns the optical fibers with the optical components.

The connector plug may be fabricated in a gravity casting process. The optical fibers are held in place by alignment holes in the mold. The small magnets or metal cylinders are also placed in the mold and aligned with the magnets in the receptacle. Then liquid plastic is poured around the optical fibers and magnets, embedding them in hard plastic when fully cured. The plug is then removed from the mold and aligns the optical fibers with the optical components in the receptacle.

The clinical force sensing glove system 100 implemented according to embodiments of the present invention may have multiple applications. For example, in a home health scenario, a patient can obtain their own measurements at home and an at-home clinical force sensing glove system 100 may transmit the data to their physician. The software in the clinical force sensing glove system 100 is compatible with any home computer. A wireless transmitter may be connected through a Universal Serial Bus (USB) port along with the calibration load cell. The data may then be transmitted over the internet in real-time so the physician can guide the patient through procedures.

The clinical force sensing glove system 100 also may be used in a clean room setting where the force measurement is brief and the sensor 104 may be disposed of after use.

Alternatively, an array of these low profile force sensors 104 can be used to measure pressure distribution or position.

Another application is in cardiology. A high sensitivity sensor 104 can measure the pulse from an artery. This enables rapid measurement of heart rate, blood pressure, pulse strength, and pulse shapes. This is particularly useful in emergency situations or in home health applications.

In a surgery environment, the clinical force sensing glove system 100 may be used to control tool manipulations.

In alternative embodiments, fiber-optic waveguides at each finger tip and under the palm of the hand may be utilized. In these embodiments, the forces applied by the clinician can be quantified and fed back to them during their practice. Through the use of this clinical glove, quantifying the forces exerted on the body, manual manipulation medical practice can become more quantitative and effective.

Optical fiber based micro-bend loss sensors hold many unique advantages over other optical sensors. For example, their optical design is simple, providing fast response times and a wide range of force measurements with excellent resolution. Second, optical fiber based micro-bend loss sensors are compact. Third, optical fiber based micro-bend loss sensors easy to embed into existing structures. Fourth, optical fiber based micro-bend loss sensors are relatively cheap to make. Fifth, the force sensors embedded in the thumb, fingertips, and palm provide real time, quantitative feed back to clinicians when manual forces are applied to a patient for diagnosis, treatment, and evaluation. The resulting clinical sensing glove implements sensors that are electronically inert and highly sensitive to manual forces applied by the hands.

Because the fiber-optic sensor used in the force sensing glove system may be designed with the clinical setting in mind, its dimensions and materials may present a minimal tactile profile to prevent distraction or disruption of normal sensation through the thumb, fingertips, and palm. Its dimensions may be limited to 10×10×1 mm and sharp edges may be eliminated that could be felt by the user or patient. The overall glove enables a clinician to "feel" a patient and has material properties similar to soft tissues. It also is designed to conform around ventral tips of the thumb, fingertips, and palm of the hand while providing faithful force feedback. The geometry of the corrugated teeth and the materials used in the sensor may determine the sensitivity and range of the fiber-optic sensor and may be tuned to meet the specific design constraints identified for various clinical applications. For some embodiments, the sensor may be capable of detecting forces as low as 1N and as high as 100N. It may be able to resolve 0.1N and be accurate to within 1N.

Because the glove itself may be disposable in order to maintain sanitation for the patient, the glove system's components can be inexpensive and relatively simple for manufacturing. Currently, surgical gloves are sold for approximately $4-5 apiece. The cost of gloves implemented according to embodiments of the present invention may be kept within this range. In a prototype built by the inventors, the sensor, fibers, light detectors, light source, and wiring are housed on the glove.

The optical fiber and sensor may be well-packaged between layers of latex, nitrile, or polystyrene for cleanliness and to prevent tearing. A wireless connection may allow the clinician to walk about freely.

Disposable Clinical Glove Having Grating-Based Sensor(s)

For some embodiments, optical sensors embedded into a disposable glove for haptic tactile feedback, goniometer, and other potential applications may include grating-based sensors. For example, an array of optical sensors may be embedded or molded into the disposable glove for variety of hand related force sensing, position sensing and actuation. The resulting disposable clinical glove may be used for force/pressure, shear, rotation, or hardness measurement.

Bragg Grating-Based Sensor(s)

Pressure and shear on finger tips and palm may be measured using the optical sensor 1300 depicted in FIG. 13, which utilizes Bragg gratings to sense force, pressure, and/or shear according to an embodiment of the present invention. The Bragg grating sensor 1302 includes an applicator 1304 where load is received. Force is translated onto the gap space between four evenly spaced Bragg gratings 1306, 1308, 1310, 1312 on two waveguides 1314 and 1316 micro-fabricated on two polymer layers 1318 and 1320, respectively. For some embodiments, if waveguide gratings in a crisscrossing configuration is used, the optical sensor 1300 may be used as a shear, rotation and/or pressure sensor. Also, in this embodiment, the crisscrossing configuration may be used as a mouse and/or drawing pen.

In operation, a broad band light source such as LED may be introduced into the waveguides 1314 and 1316 via an optical fiber (not shown). Pressure and shear may be obtained from the deformations of the array of Bragg gratings 1306, 1308, 1310, and 1312. The deformation of each pressure point may be determined by monitoring the shift 1322 in Bragg wavelength of the reflected signal with the changes in the measurand in each grating 1306, 1308, 1310, and 1312. In some embodiments, the measurand may be the strain induced by the load on each grating 1306, 1308, 1310, and 1312. The Bragg wavelength, $\lambda_B$, of a grating is given by $\lambda_B=2n\Lambda$, where $\Lambda$ is the grating pitch and n is the effective index of the core of the waveguide. Direction and magnitude of the applied force can be determined by the increase or decrease of the grating periods of these four gratings 1306, 1308, 1310, and 1312.

As described above, the Bragg grating sensor 1302 may be constructed using the two polymer layers 1318 and 1320 with waveguides 1314 and 1316 that have periodically spaced Bragg gratings 1306, 1308, 1310, and 1312. Shear and vertical load may be derived from the strain of two adjacent Bragg gratings (labeled as S1, S2). The load may be transferred to the gratings 1306, 1308, 1310, and 1312 on the waveguides 1314 and 1316 through the applicator 1304, which sits between the top layer 1318 and the polymer layer 1320 that includes the gratings 1306, 1308, 1310, and 1312. The magnitude of the applied pressure is proportional to the sum of the strain while the applied shear is proportional to the difference of the strain obtained by S1 and S2.

When a vertical load 1330 is applied to the applicator 1304, both grating pitches may be elongated due to a Poisson's ratio deformation orthogonal to the applied loading. There may be an increasing shift in wavelength of the light passing through the Bragg grating sensor 1302. On the other hand, when shear force is applied along the axial direction, one grating may be under compression and the other may be under tension because the bottom support of each element (not shown) prevents the gratings from sliding forward. The resulting wavelength shift may have one going up and the other going down. The shear measurement of the entire sensing area of the Bragg grating sensor 1302 may be derived from the axial shear measurement of the two Bragg grating planes, i.e., each waveguide grating layer in the Bragg grating sensor 1302, which are configured so the waveguide of the top and bottom planes are perpendicular to one another. Temperature compensation may be automatic, as wavelength change due to temperature variations may be the same for all gratings 1306, 1308, 1310, and 1312.

The micro-fabricated waveguides 1314 and 1316 and gratings 1306, 1308, 1310, and 1312 may be constructed using PDMS elastomer. PDMS is widely available, clean room compatible and a physically and chemically stable silicone rubber with a wide range of applications. Sylgard 184 silicone elastomer from Dow-Corning Corporation is among the most commonly used PDMS elastomers. The primary advantages of PDMS are that it bonds easily and has very good optical properties such as high transparency, low loss and, most importantly, a refractive index (n=1.43) that closely matches the indices of commercially available optical fibers. Some physical and chemical attributes of PDMS are, compared to other polymers, a unique flexibility (the shear modulus G between 100 kPa and 3 MPa), low durometer hardness (Shore A 40), very low loss tangent (tan $\delta \ll 0.001$), high gas permeability, low temperature variation, and it is virtually inert to most chemicals and essentially non-toxic in nature. It is also a fairly low cost material (approximately $80/kg in today's dollars). PDMS also has optical and physical properties suitable for use in the Bragg grating sensor 1302, and PDMS' low surface energy (~21.6 dyne/cm) allows replicas to be separated from their molds easily.

A simple micro-fabrication technique may be used that allows the rapid construction of complex optical gratings and waveguide system of the Bragg grating sensor 1302. The Bragg grating sensor 1302 may be fabricated using a technique derived from the micro-molding method. The process allows for stacking of many thin patterned PDMS layers to realize a complex three-dimensional (3-D) structure. The master for each layer may be formed on a silicon wafer using AZ1350 photoresist (Shipley Company, Marlborough, Mass.) or epoxy based SU-8 photoresist (MicroChem Corporation XP SU-8 2000 series, Newton, Mass.). PDMS may be cast against the master to produce the molded structure.

Figure 14:
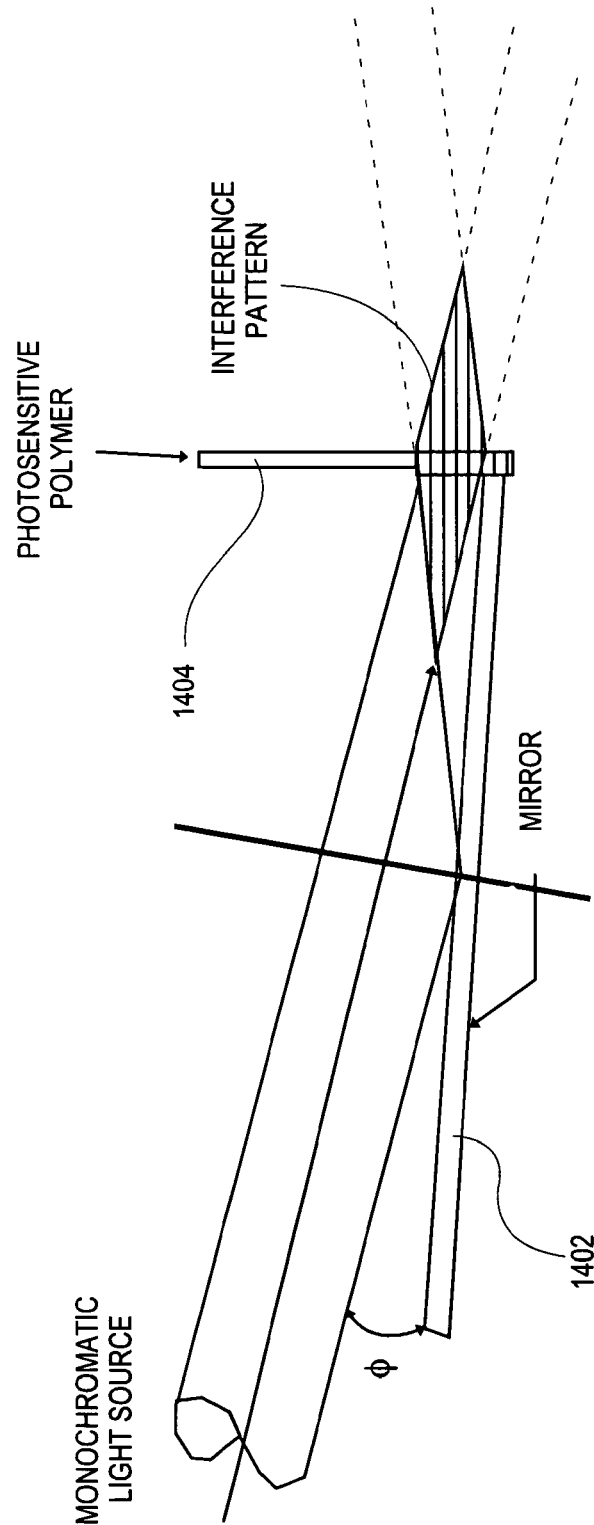
FIG. 14 illustrates a Lloyd's mirror interferometer for a grating-based sensor according to an embodiment of the present invention.

For some embodiments, the gratings 1306, 1308, 1310, and 1312 may be constructed using two polymer layers that have slightly different optical indices. The array of gratings 1306, 1308, 1310, and 1312 may be formed by first exposing a 488 nm wavelength ultraviolet (UV) interference pattern (using an argon laser) on a photosensitive polymer (AZ 1350, refractive index=1.618) placed on top of a silicon substrate to form a master. The film is subsequently developed and there remains a periodicity of fringes on the film. Although there are many techniques of exposing the interference patterns to form the gratings 1306, 1308, 1310, and 1312, the one embodiment utilizes a Lloyd's mirror interferometer configured according to FIG. 14. The interference fringes of constant spatial frequency are formed when a monochromatic, plane wave front is spatially divided in half by a plane mirror 1402 and the two halves are superimposed later when the two are converged on the photosensitive polymer 1404. The spatial frequency $\upsilon$ (fringes/mm) only depends on wavelength, $\lambda$, and the angle, $\phi$, at which the two wave fronts interfere, which is expressed as $\upsilon=2 \sin \phi/\lambda$.

Figure 15:
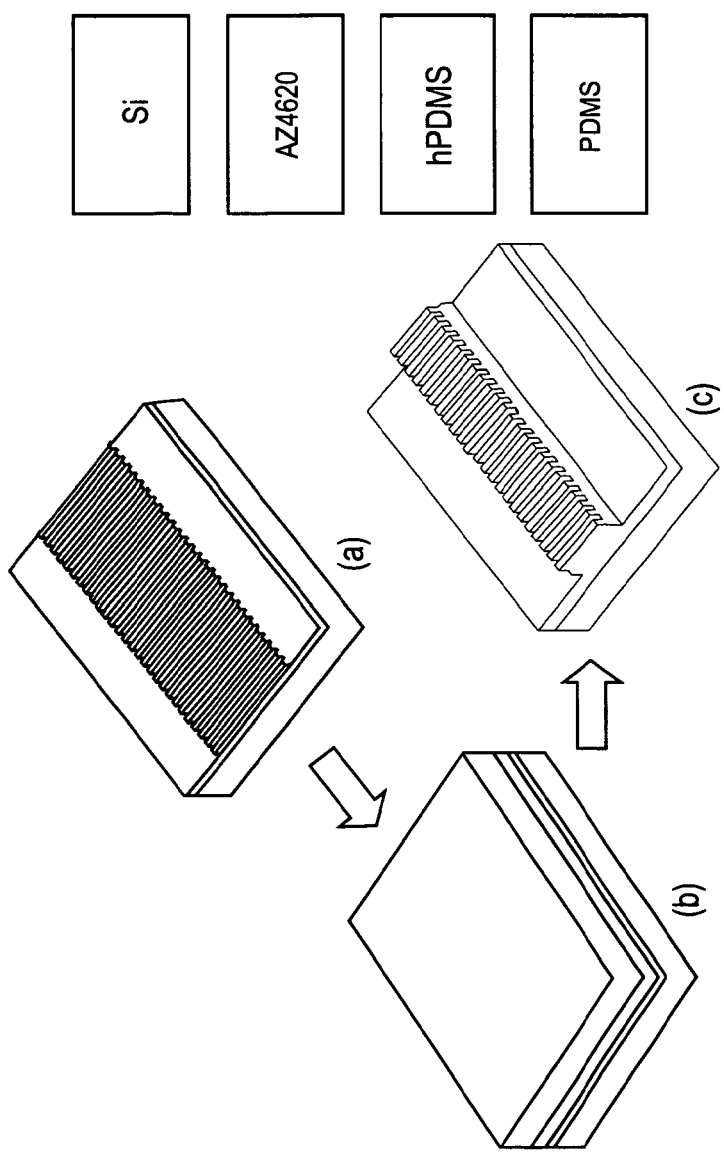
FIG. 15($a$) illustrates a grating pattern formed on an AZ 4620 master for a grating-based sensor according to an embodiment of the present invention.

To fabricate the gratings 1306, 1308, 1310, and 1312 according to one embodiment, a "master" grating pattern may be created through two-beam interference on a positive photoresist, as illustrated in FIG. 15. FIG. 15(a) shows the grating pattern formed on an AZ 4620 master. FIG. 15(b) shows hard PDMS (hPDMS) spin coated on the master over the grating pattern, and PDMS spin coated on the hPDMS. FIG. 15(c) shows the polymer (hPDMS and PDMS) separated from the mold/master.

Figure 16:
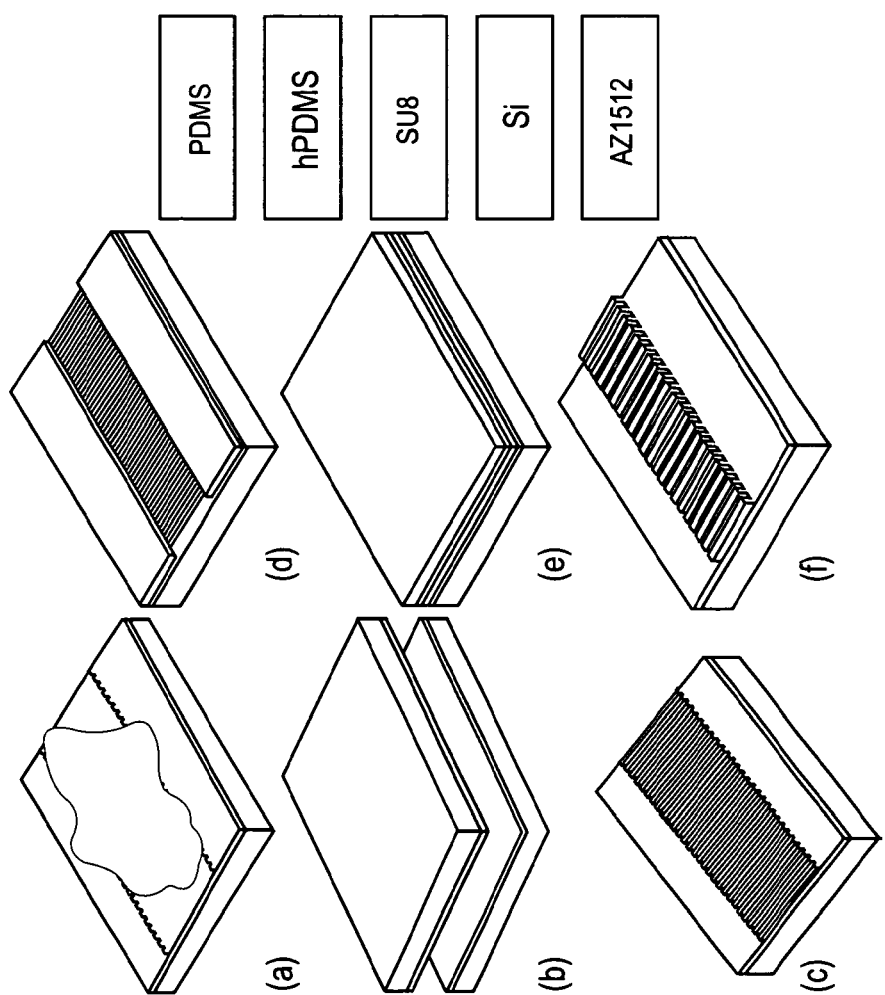
FIG. 16($a$) illustrates a solvent-assist micro-contact molding (SAMIM) process used to transfer a grating pattern onto an epoxy-based SU-8 film for a grating-based sensor according to an embodiment of the present invention, in which the hPDMS stamp is wet with ethanol.

The master serves as the mold to produce a PDMS "stamp" that can be used to transfer the grating pattern onto an epoxy-based SU-8 film via a solvent-assist micro-contact molding (SAMIM) process. FIG. 16 illustrates this process according to an embodiment of the present invention. With the grating pattern applied to the SU-8 substrate, a second layer of AZ1512 is applied to form a trench around the grating, creating a new mold. This mold is then used to create the final PDMS waveguide grating in two spin-coated layers.

In order to prevent stiction between the AZ4620 grating master and the hPDMS stamp, the master may be silanized by exposing the film to trichlorosilane (Gelest, Inc. PA) vapor in a vacuum chamber for 30 minutes. The hPDMS may use a mixture of four different components. The mixture includes of 3.4 grams of (7-8% Vinylmethylsiloxane) (Dimethysiloxane), two drops (approximately 4 μL) of 1.3.5.7-Tetravinyl-1,3,5,7-Tetramethylcyclotetrasiolxane, and one drop (~2 μL) of platinum divinyltetramethyldisiloxane. The solution may then be thoroughly mixed in a polystyrene dish and then put into a desiccator to remove bubbles. One gram of (25-30% Methylhydrosiloxane) (Dimethylsiloxane) may then be added into the solution before pouring and spin coating onto the AZ4620 grating master. The resulting hPDMS film thickness may be around 30-40 μm (@1000 rpm/40 seconds). This resulting hPDMS film may be baked in an oven at 60° C. for 10 minutes. A previously mixed Sylgard 184 may be poured onto the hPDMS layer then cured at 60° C. overnight before releasing from the AZ4620 grating master. The Sylgard 184 is supplied as two-part kits: a liquid base resin and a curing agent. To prepare the Sylgard 184, a mixture of base resin and curing agent in 10:1 ratio was thoroughly mixed and then the air bubbles were removed using a desiccator. A solvent-assisted micro-contact molding (SAMIM) technique was used to transfer the grating pattern onto a final SU8 grating mold using SU8-2002, an epoxy-based negative photoresist (MicroChem. Corp. MA).

FIG. 16(a) illustrates wetting of the hPDMS stamp with ethanol (black splash) according to an embodiment of the present invention. FIG. 16(b) illustrates placing the hPDMS stamp on top of a prebaked SU8-2002 film without any additional pressure applied according to an embodiment of the present invention. FIG. 16(c) illustrates the grating pattern as transferred to SU-8 film after the stamp was released according to an embodiment of the present invention. FIG. 16(d) illustrates the waveguide trench patterned using photolithography according to an embodiment of the present invention. FIG. 16(e) illustrates the spin coat hPDMS and PDMS according to an embodiment of the present invention. FIG. 16(f) illustrates the polymer as released from the mold once the polymer is cured according to an embodiment of the present invention.

For other embodiments, the grating periods may be fabricated using electron-beam writing and exposed by phase mask lithography using a UV laser.

For an optical fiber-based Bragg grating sensor, the waveguide is replaced by an optical fiber. The optical fiber may be embedded into the glove material such as nitrile or elastomer. The Bragg grating may be holographically written into a germanium doped optical fiber by exposure to ultraviolet (around 245 nm) interference patterns, or exposed by a phase mask technique.

Figure 17:
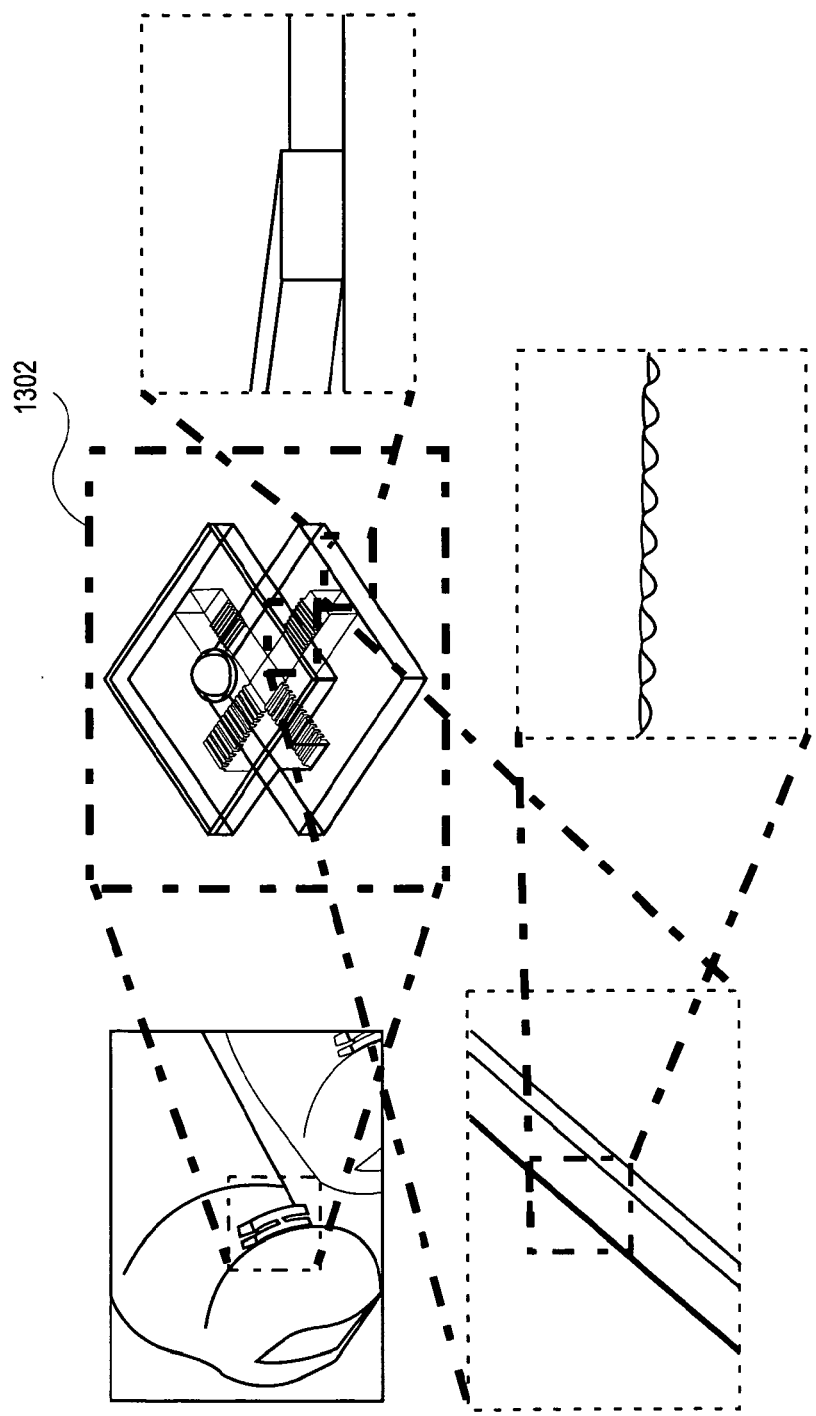
FIG. 17 illustrates a Bragg grating-based sensor disposed in a disposable clinical glove according to an embodiment of the present invention.

FIG. 17 illustrates the Bragg grating sensor 1302 disposed (embedded/attached) in a disposable clinical glove according to an embodiment of the present invention. According to some embodiments, the size of the Bragg grating sensor 1302 may have an area less than approximately 1×1 mm² and a thickness less than approximately 200 μm.

Long Period Grating-Based Sensor(s)

Figure 18:
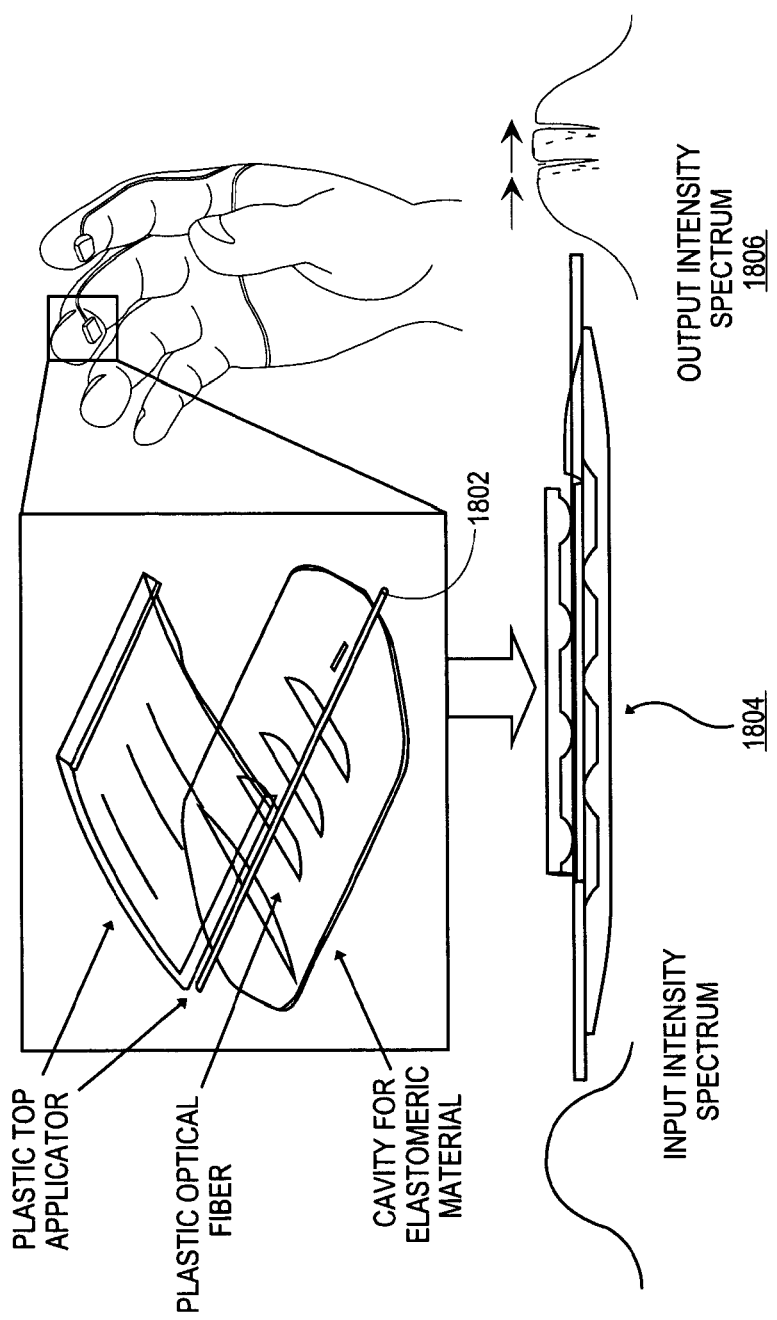
FIG. 18 illustrates a pressure and shear sensor disposed on finger tips and a palm of a disposable clinical glove for a long period grating-based sensor according to an embodiment of the present invention.

Pressure and shear on finger tips and the palm of a disposable clinical glove also may be measured using the glove sensor depicted in FIG. 18, which utilizes a long period grating array to sense force, pressure, and/or shear according to an embodiment of the present invention. That is, instead of using Bragg grating sensor, a higher order grating may be used, such as long period grating. This long period grating may be part of a passive optical fiber 1802 (or micro-fabricated waveguide device) having a periodic refractive index modulation that couples the guided fundamental mode in the core of the optical fiber 1802 to a forward propagating cladding mode. This mode decays rapidly due to scattering at the cladding-air interface and the bend in the optical fiber 1802. An advantage of using a long period grating is that the period is not submicron, which is difficult to make. By increasing the grating period, a sophisticated fabrication process is no longer needed to produce the gratings in the optical fiber 1802.

The long period grating may now be formed mechanically by teeth similar to the applicator 302 shown above in the FIG. 3. Instead of looking at the light attenuation at the output on the other end of the optical fiber 1802, the spectrum is observed instead. Instead of using a spectrometer to observe the wavelength shift 1322 as described above with reference to FIG. 13, a wavelength demultiplexer (described in more detail below) can be used to detect each wavelength from each grating. The transmission spectrum 1806 illustrates that when force is applied to the sensor 1804, the notches in the transmission spectrum 1806 move to a new location depending on the magnitude of the applied force.

In an alternative embodiment, the periodic index change may be produced in the optical fiber 1802 by exposing a regular single mode optical fiber with low dosage of $CO_2$ laser light having a beam width tuned close to the optimal wavelength of the sensor.

Wavelength Analysis for Bragg Grating and Long Period Grating-Based Sensors.

Figure 19:
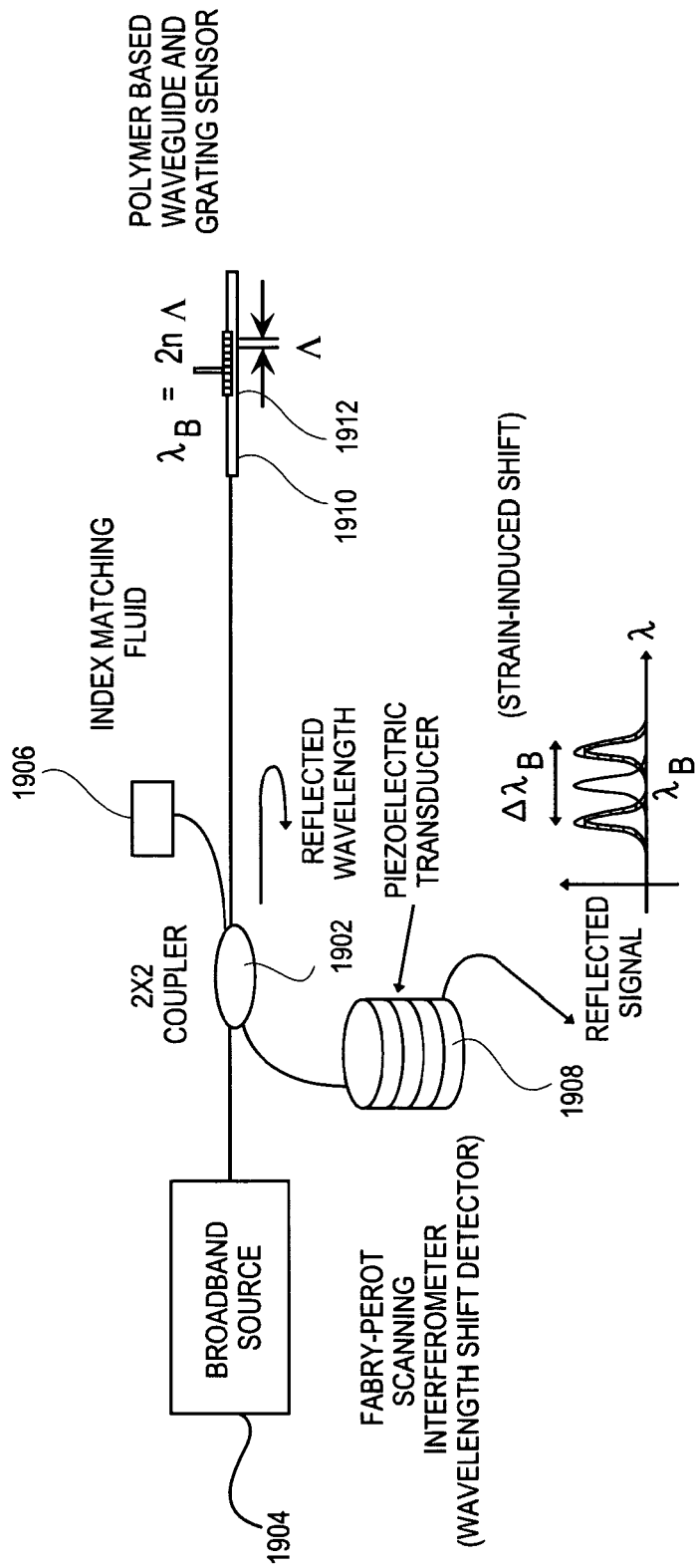
FIG. 19 is a schematic diagram of grating-based sensor wavelength encoding according to an embodiment of the present invention.

In one embodiment, for wavelength shift detection, an optical fiber based Fabry-Perot scanning interferometer may be used. The construction of the sensor is relatively simple with two mirrors directly deposited to the ends of an optical fiber to form an optical cavity. FIG. 19 is a schematic diagram of grating-based sensor wavelength encoding according to an embodiment of the present invention. In the illustrated embodiment, a coupler 1902 is coupled to a broadband light source 1904, index matching fluid 1906, and a Fabry-Perot scanning interferometer wavelength shift detector 1908. An optical fiber 1910 couples the components to each other. One or more gratings 1912 is disposed in the optical fiber 1910.

For some embodiments, wavelength scanning may be accomplished by axially straining a short section of the optical fiber 1910 using the Fabry-Perot piezoelectric actuator 1908. In one embodiment, optical fiber based Fabry-Perot (FP) scanning interferometer may include two mirrors directly deposited to the ends of an optical fiber to form an optical cavity. Wavelength scanning may be achieved by axially straining a short section of the optical fiber by a piezoelectric actuator. As the Fabry-Perot (FP) scanning interferometer 1908 scans over the returning signals from the gratings 1912, the Bragg wavelengths $\lambda_B$ are determined and recorded from the voltage applied to the piezoelectric actuator as the return signals are detected. The phase modulation ($\Delta\phi$) induced by the Bragg wavelength shift, $\Delta\lambda_B$, is given by $\Delta\Phi = 2\pi n_f d \Delta\lambda_B / \lambda_B^2$, where $n_f$ is index of refraction of the fiber and d is the fiber cavity length.

In embodiments of the present invention, the coupler 1902 may be any suitable 2×2 bidirectional coupler that is capable of coupling light into and out of the pressure sensor 100.

In embodiments of the present invention, the broadband light source 1904 may be any suitable light source capable of transmitting a light beam having a broad range of wavelengths. In one embodiment, the broadband light source 1904 may provide ultraviolet (UV), visible, or infrared band of light using laser diode or light emitting diode. In another embodiment, the broadband light source 1904 may provide white light.

In embodiments of the present invention, the index matching fluid 1906 may be any suitable index matching material that is capable of matching the index of refraction n of the coupler 1902 with the index of refraction n of the polymer used.

In embodiments of the present invention, the wavelength shift detector 1908 may be any suitable light detector capable of determining light wavelengths. In embodiments in which the wavelength shift detector 1908 may be located off of the polymer, the wavelength shift detector 1908 may be a spectrum analyzer.

In the illustrated embodiment, the coupler 1902 couples a broadband light beam from the broadband light source 1904 to the array of gratings 1912. Each of the gratings 1912 in the array may reflect light having its specific Bragg wavelength $\lambda_B$ back to the coupler 1902. The coupler 1902 directs the reflected light to the wavelength shift detector 1908, which determines the Bragg wavelength $\lambda_B$ reflected by the gratings 106, 108, 110, 112, 114, and 116.

In an alternative embodiment, an off-the-shelf fiber Bragg grating interrogation system may be used. Currently available Fabry-Perot scanners can be scanned at rates >300 Hz. The minimum resolvable Bragg wavelength shift, $\Delta\lambda_B$ for a free spectral range of forty nm (wavelength range 1525 to 1565 nm) with grating spaced by 625 pm via a sixteen bit digital to analog is around 0.6 pm, which should be sufficient to provide the speed and resolution needed for dynamic strain measurement of stress distributions.

Figure 20:
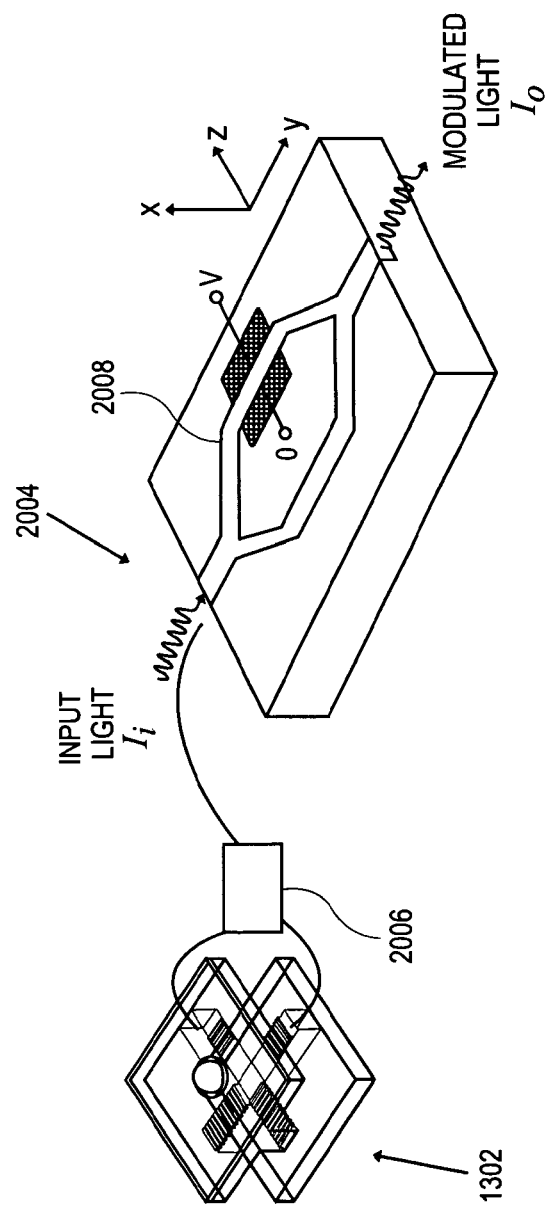
FIG. 20 is a schematic diagram of an integrated electro-optic Mach Zehnder interferometer interrogated system for a grating-based sensor according to an embodiment of the present invention.

In other embodiments, an integrated Fourier transform spectrometer, where signal is analyzed, may be utilized. Several of the integrated Fourier transform spectrometer may be used as interrogation system. FIG. 20 is a schematic diagram of a suitable integrated electro-optic Mach Zehnder interferometer according to an embodiment of the present invention. In the illustrated embodiment, the Bragg grating sensor 1302 is coupled to the integrated electro-optic Mach Zehnder interferometer 2004 via a 2×1 coupler 2006.

The Fourier transform spectrometer uses the integrated electro-optic based Mach Zehnder interferometer 2004 where scanning is done not by moving one or more mirrors but by changing the refractive index of the optical path on one of the arms 2008 in the interferometer 2004. By doing that, the phase modulation is controlled by the input voltage V.

The example integrated Mach-Zehnder waveguide modulator 2004 may be made of electro-optical polymer. The polymer's extraordinary axis is aligned with z-axis, and its ordinary axes are aligned with x- and y-axis.

Other embodiments may utilize a far infrared (IR) spectrometer. For a far IR spectrometer, the waveguide arm 2008 may have a width of 1 µm and voltage V may be applied across the waveguide along z-direction, over a length of 30 mm. The wavelength of the light may be 2000 nm, the electro-optic coefficient may be $r_{33}=40\times10^{-12}$ and the refractive index may be $n_o=1.52$. With these values, the half-wave voltage $V_\pi$ for the transverse electric (TE) wave resolution and phase modulation due to applied voltage may be determined.

Because the phase modulation as a function of refractive index is represented as:

$$\phi = n(E)k_0 L = 2\pi n(E)L/\lambda_0$$

$$\phi_0 \equiv \frac{2\pi n L}{\lambda_0}$$

$$\phi \approx \phi_0 - \pi \frac{rn^3 EL}{\lambda_0}$$

$$E = V/d$$

$$\phi = \phi_0 - \pi \frac{V}{V_\pi}: \text{Phase modulation}$$

$$V_\pi = \frac{d}{L}\frac{\lambda_0}{rn^3}: \text{Half-wave voltage}$$

$$\delta\lambda = \frac{0.5\lambda^2}{\Delta L} \text{scanning resolution,}$$

the resulting $V_\pi=0.475$. If we input a V=100 volt, we get $\Delta\phi=661.96$ and equivalent $\Delta L=1.386\times10^{-4}$ m and the scanning resolution is 2 nm. In the above equations, $\phi$ is phase modulation, $\phi_0$ is the initial phase difference between sensing and reference arms, L is sensing length, E is electrical field, $\lambda_0$ is initial operating wavelength, $k_0$ is wave number in air, n is index of refraction, r is electro-optic coefficient, V is voltage, and d is thickness of the electro-optic material.

A derivation of the specific intensity $I_k(x)$ observed for input of a single wave number k gives $$I_k(x) = J(k)\langle T(k)\rangle \frac{1}{2}[1+\cos(kx)],$$

where J(k) is input intensity and T(k) is coupling efficiency.

Figure 21:
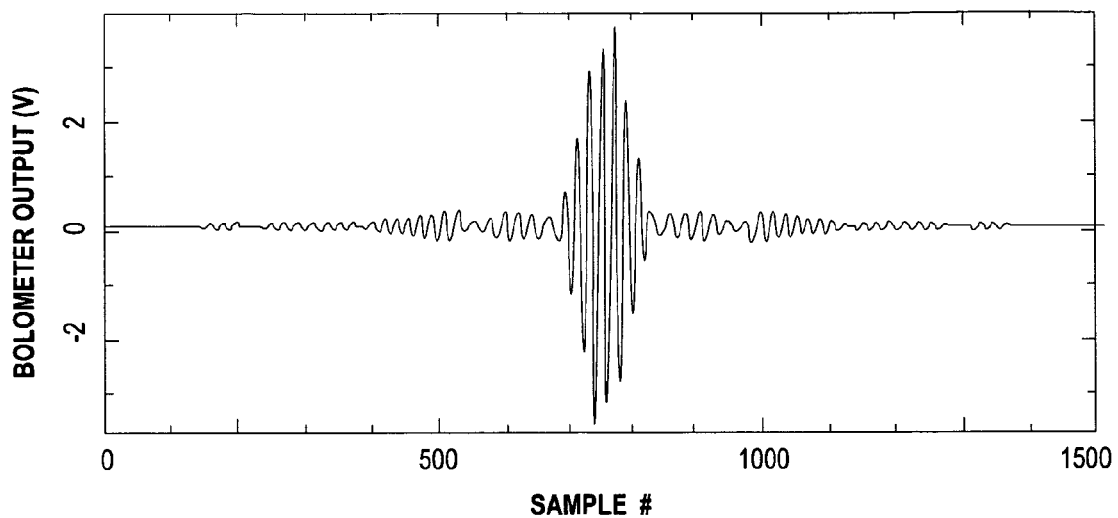
FIG. 21 illustrates an interferogram for a grating-based sensor according to an embodiment of the present invention.

An example of the resulting interferogram according to an embodiment of the present invention is shown in FIG. 21. To obtain the total intensity I(x) measured for a given $\Delta L$ from input at all wave numbers is found by integrating $I_k(x)$, which is equivalent to applying an inverse Fourier cosine transform, where the Fourier cosine transform, $$\mathcal{F}_x^{[c]}[f(x)](k) = R\, \mathcal{F}_x[f(x)](k).$$

where the Fourier cosine transform is the real part of the full complex Fourier transform:

$$I(x) = \int_0^\infty I_k(x)dk = \frac{1}{2}\int_0^\infty [1+\cos(kx)]\langle T(k)\rangle J(k)dk$$

$$\frac{1}{2}\int_0^\infty \langle T(k)\rangle J(k)dk + \frac{1}{2}\int_0^\infty \cos(kx)\langle T(k)\rangle J(k)dk$$

$$\frac{1}{2}I(0) + \frac{1}{2}\int_0^\infty \cos(kx)\langle T(k)\rangle J(k)dk$$

$$\frac{1}{2}I(0) + \frac{1}{2}\mathcal{F}_c^{-1}[\langle T(k)\rangle J(k)].$$

The fact that the intensity of the white fringe (x=0) can be written:

$$I(x) = \int_0^\infty I_k(x=0)dk = \int_0^\infty J(k)\langle T(k)\rangle dk,$$

Figure 22:
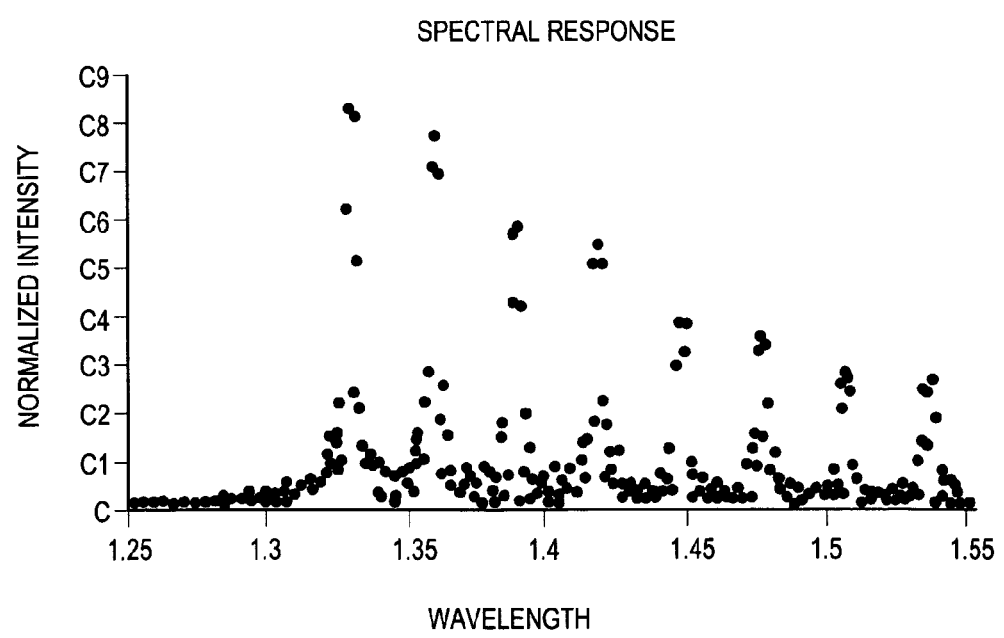
FIG. 22 is a graphical representation of a Fourier transform spectrometer for an example of how a grating spectrum may be generated from a grating-based sensor disposed on a disposable clinical glove according to an embodiment of the present invention.

I(x) can now be inverted for the one-sided case to yield the real spectrum $J(k)\langle T(k)\rangle = 2\mathfrak{F}_c[I(x)-\frac{1}{2}I(0)]$, which is illustrated in FIG. 22. Specifically, FIG. 22 is a graphical representation of the Fourier transform spectrometer for the above example of how the grating spectrum may be generated from the grating-based pressure/shear sensor on a disposable clinical glove according to an embodiment of the present invention. In FIG. 22, the "y" axis is normalized intensity and "x" axis is wavelength.

Alternatively, there are a number of other integrated spectrometers that can be made that include fiber optic Fabry-Perot interferometers and electro-optic liquid crystal based Fourier transform spectrometers that can be used instead of above Mach Zehnder interferometer technique.

Fabrication of Bragg Grating and Long Period Grating-Based Sensor(s)

FIG. 23 illustrates a process for fabricating grating-based sensors for the disposable clinical glove according to an embodiment of the present invention. In the illustrated embodiment, fabrication is based on electro-optic material, however, this device can be made of LiNbO3 where we can push the detection region upward to approximately 1 to 10 µm range instead of approximately 0.2 to 1.8 µm range for the electro-optic material.

In FIG. 23(a), metal may be disposed on a bottom electrode. For some embodiments, gold (Au) may be sputtered on a silicone/elastomer/PDMS substrate. Other deposition techniques may be utilized as well (e.g., spin on, etc.).

In FIG. 23(b), illustrates an embodiment in which the bottom electrode may be patterned using a mask and ultraviolet (UV) radiation. The undesired metal may be removed from the bottom electrode using any suitable removal technique (e.g., etching, etc.).

In FIG. 23(c), illustrates an embodiment in which a cladding layer is disposed on the remaining metal using any suitable deposition technique. The cladding layer may be patterned using a mask and ultraviolet (UV) radiation to achieve substantially the same width as the electro-optic core layer In FIG. 23(d), an electro-optic polymer is disposed on the cladding layer. Also, a PDMS mold is disposed on the electro-optic polymer to stamp the pattern from the mold onto the electro-optic polymer. Some embodiments utilize a solvent-assisted nano-imprint to pattern the electro-optic polymer. The mold may then be removed from the imprinted electro-optic polymer.

In FIG. 23(e), another metal layer may be disposed on the imprinted electro-optic polymer to form a top electrode. For some embodiments, gold (Au) may be sputtered to form the top electrode.

Figure 24:
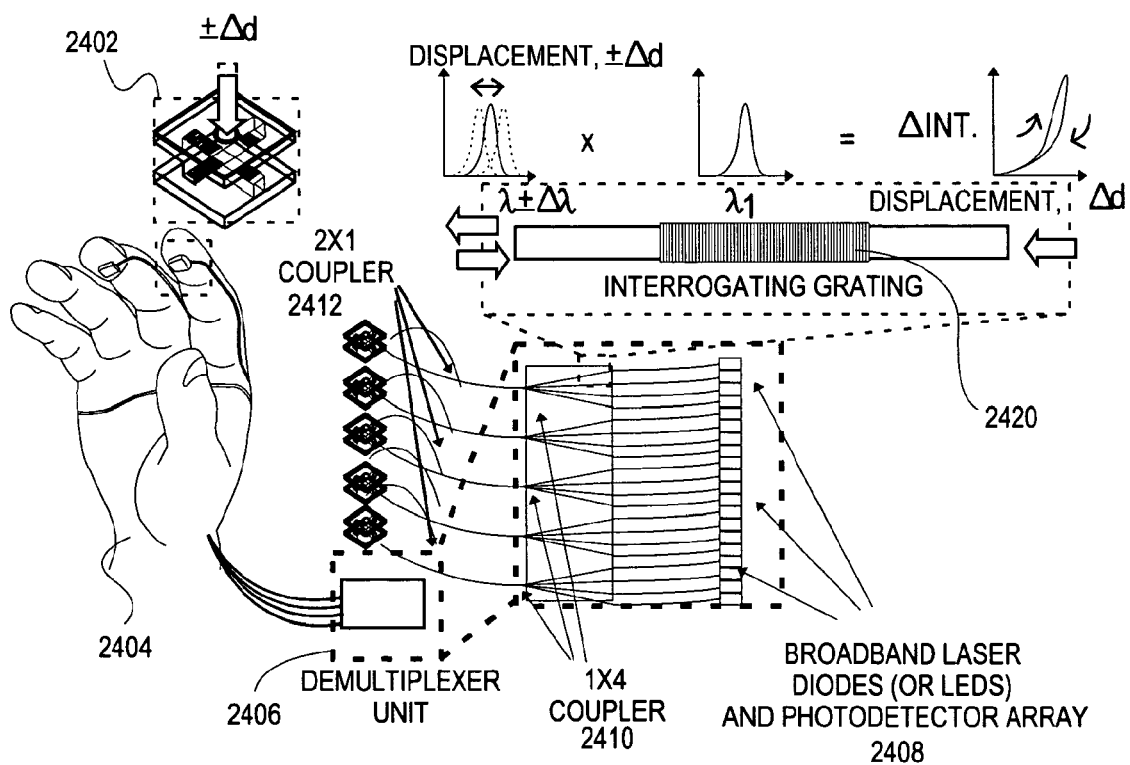
FIG. 24 a schematic diagram of a clinical sensing system for a grating sensor using Bragg grating filters and a multiple channel demultiplexing system according to an embodiment of the present invention.

An alternative to using an interferometry interrogation system and method for wavelength analysis for the above-described grating-based sensors is to use a wavelength demultiplexer where wavelengths from each pressure sensor are analyzed. FIG. 24 illustrates an interrogating system using Bragg grating filters and a multiple channel demultiplexing system, showing how wavelength from each grating on the pressure/shear sensor may be analyzed according to an embodiment of the present invention. In the illustrated embodiment, several grating-based sensors 2402, which are disposed (e.g., embedded) in a disposable clinical glove 2404, are coupled to a demultiplexer unit 2406. The demultiplexer unit 2406 includes light sources (broadband laser diodes or LEDs) and a photodetector array 2408. The demultiplexer unit 2406 also includes a 1×4 coupler 2410 and a 2×1 coupler 2412.

Light from the LEDs inside demultiplexer unit 2406 are introduced to each sensor 2402 through the 4×1 coupler 2410 and then the 2×1 fiber (or waveguide) coupler 2412. Light is filtered when going through Bragg gratings inside the demultiplexer system. Each Bragg grating may be tuned to a specific Bragg wavelength. Therefore only a specific wavelength such as $\lambda_1$ shown in the example gets reflected back to each detector. The remaining light continues travel down the path until it reaches those four Bragg gratings in each pressure/shear sensor embedded in the glove 2404.

Initially, if both the grating inside the demultiplexer (labeled interrogating grating 2420) and the sensor grating have the substantially the same Bragg wavelength, a maximum reflected intensity may be observed at the detector. When a force is applied to the Bragg grating sensor in the glove 2404 in the x, y, z or combination of these directions, a shift in wavelength ($\Delta\lambda$) in each of those four Bragg gratings in each pressure/shear sensor embedded in the glove 2404 may occur. These shifts in wavelength are observed in the reflected Bragg grating peaks (i.e. $\lambda_1+\Delta\lambda$) The reflected light after passing through the interrogating Bragg gratings 2420, due to the fact that interrogating gratings 2420 used as wavelength filters and tuned to specific Bragg wavelengths as the initial Bragg wavelength in the sensor (i.e. $\lambda_1$), the intensity observed at each detector may decrease. The amount depends on the wavelength difference between the interrogating grating 2420 and Bragg gratings in each pressure/shear sensor embedded in the glove 2404. A maximum intensity may be observed at the detector if both the Bragg gratings in each pressure/shear sensor embedded in the glove 2404 and interrogating gratings 2420 have substantially the same wavelength. The output intensity may decrease when the grating periods of the Bragg gratings in each pressure/shear sensor embedded in the glove 2404 are perturbed by an applied load.

One reason the interrogating system is referred to as a demultiplexer is because the reflected light from the Bragg gratings in each pressure/shear sensor embedded in the glove 2404 is split up into different output channels. Each channel has a grating filter that only allows a very narrow band of wavelengths to pass through and only specific wavelength that pass through is detected by the photodetector in the end. Both light sources (in this case either a LED or laser diode) and photodetectors (silicone based is operating in the visible range and germanium based detector is in IR region) are embedded inside the demultiplexer system. The uniqueness of this system is that output from the Bragg gratings in each pressure/shear sensor embedded in the glove 2404 is analyzed in terms of intensity instead of wavelength so the signal does not require a spectrometer to detect these Bragg wavelength peaks in the interrogating system.

Figure 25:
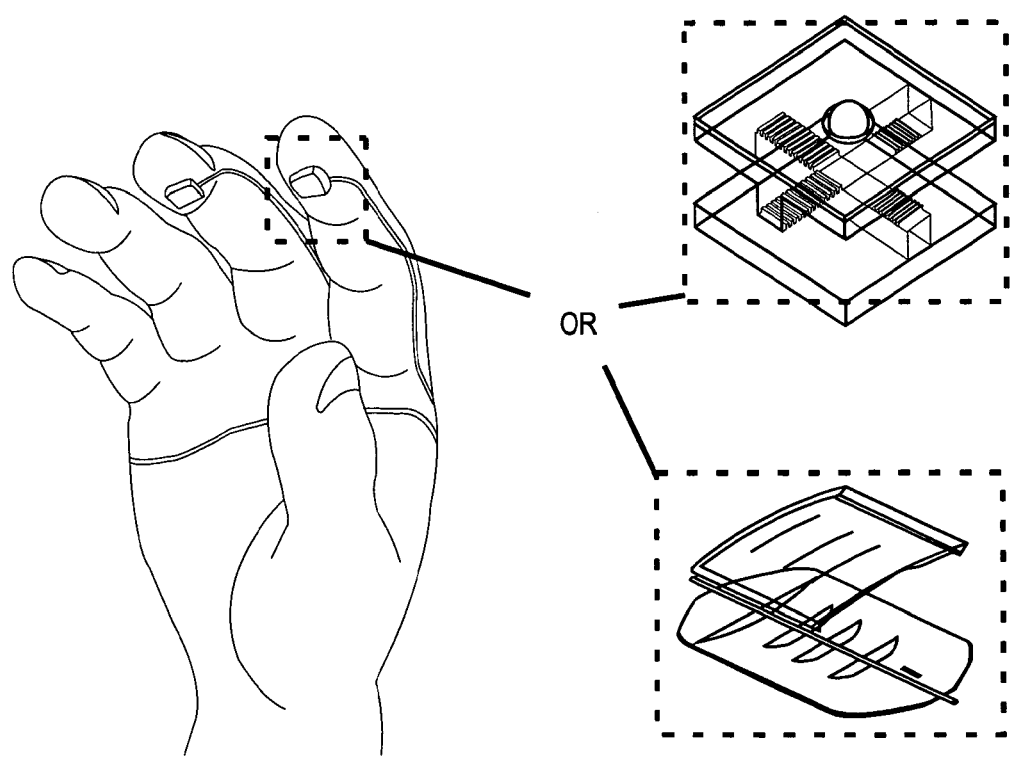
FIG. 25 illustrates a view of the clinical sensing glove depicted in FIG. 24 having two different mechanical deformers for a grating-based sensor according to an embodiment of the present invention.

It is to be noted that the overall grating-based sensor system implemented according to embodiments of the present invention has the same configuration as a micro-bend loss sensor implemented according to embodiments of the present invention and as described in earlier. One difference may be on the pressure sensor. For example, the grating-based sensor system can measure pressure or both pressure and shear on each sensor. In some embodiments of the present invention there may be an array of sensors embedded on desired locations, such as finger tips, the palm, and different metatarsal regions as shown in FIG. 25. In FIG. 25, the overall glove sensor system layout for grating based sensors according to embodiments of the present invention is illustrated, as well as a sensor close up where only a waveguide Bragg grating (a) and fiber optic long period grating sensor (b) are shown.

Figure 26:
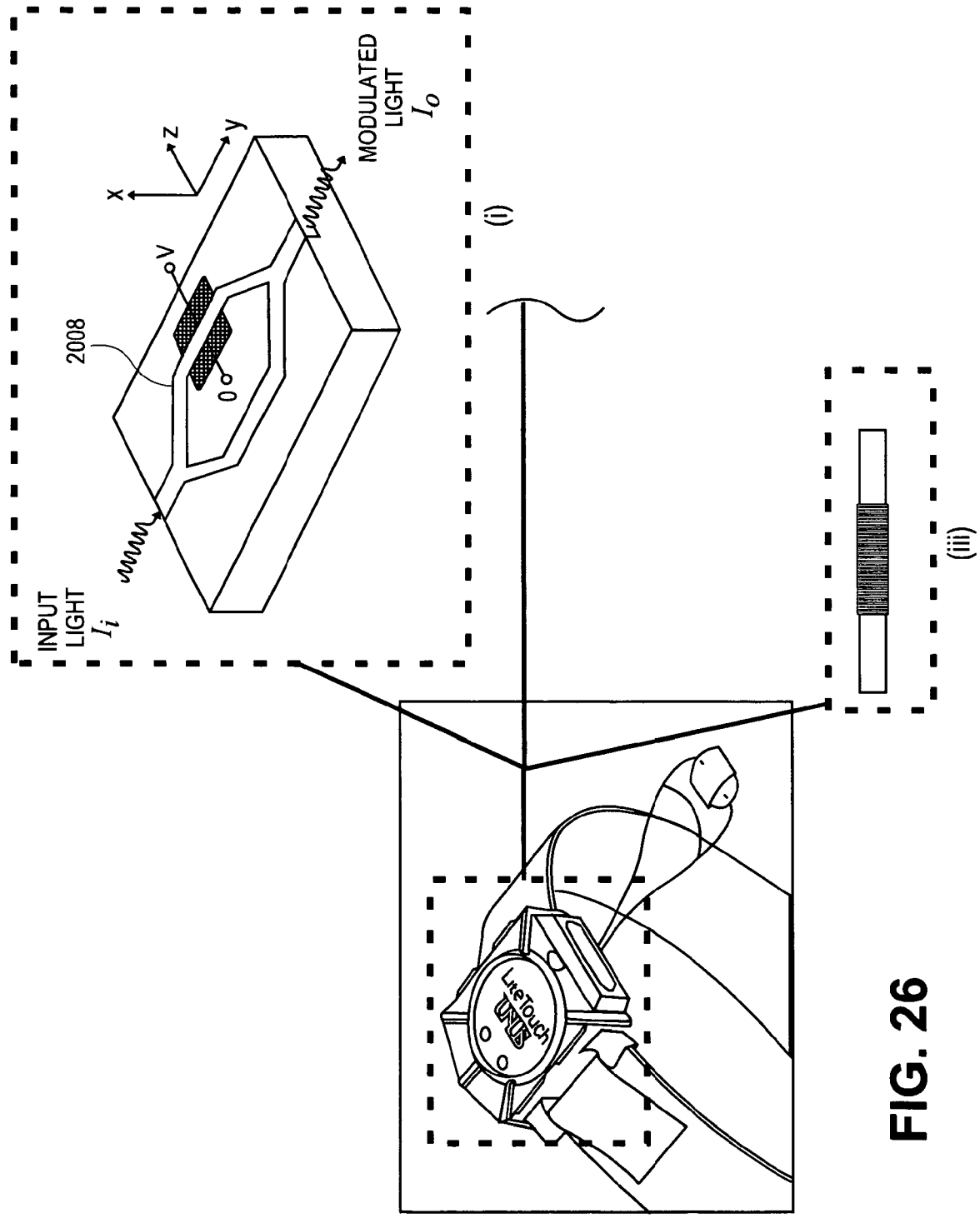
FIG. 26 illustrates an interrogating system embedded inside a wrist cuff unit for a grating-based sensor according to other embodiments of the present invention.
Figure 26:
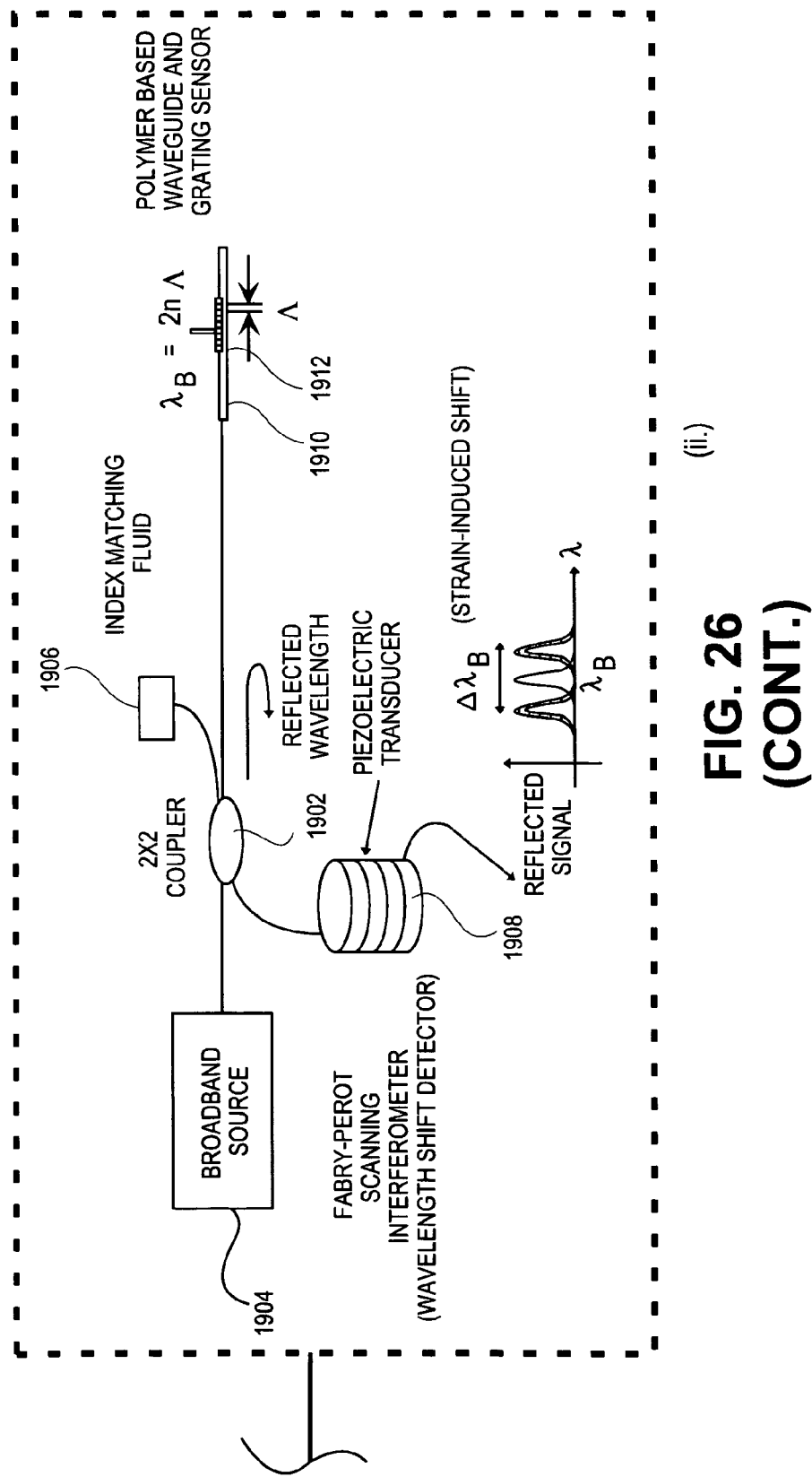

FIG. 26 shows a different interrogating system embedded inside the wrist cuff unit where signals are being analyzed and processed, and sent to a data acquisition system (DAQ) and computer according to other embodiments of the present invention. Specifically, the interrogated system inside watch wrist cuff includes (i) an integrated FTS system, (ii) a scanning spectrometer, and (iii) a demultiplexer detection system.

Hardness Measurement

The same grating-based sensor as described above may also be used as a hardness sensor where the user can use the disposable clinical glove to measure the tissue hardness on patients. The grating-based sensor may be modified to measure different hardness by modifying the insert (e.g., the elastomeric material) inside of the grating-based sensor depicted in FIG. 18 and using polymer material having different stiffness. If one wishes to measure softer tissue, one may embed the grating-based sensor with softer polymer and vice versa.

Goniometer Application

Current methods of determining the degree of disability in a hand utilizes a goniometer measurement at each knuckle of the hand with a time delay between full-hand measurement sets. This is a time-consuming process that requires careful recording of the data sets and multiple measurement runs per session. Nationally, this test is performed many thousands of times annually, so there is a definite market for any product that could improve the current process.

Figure 27:
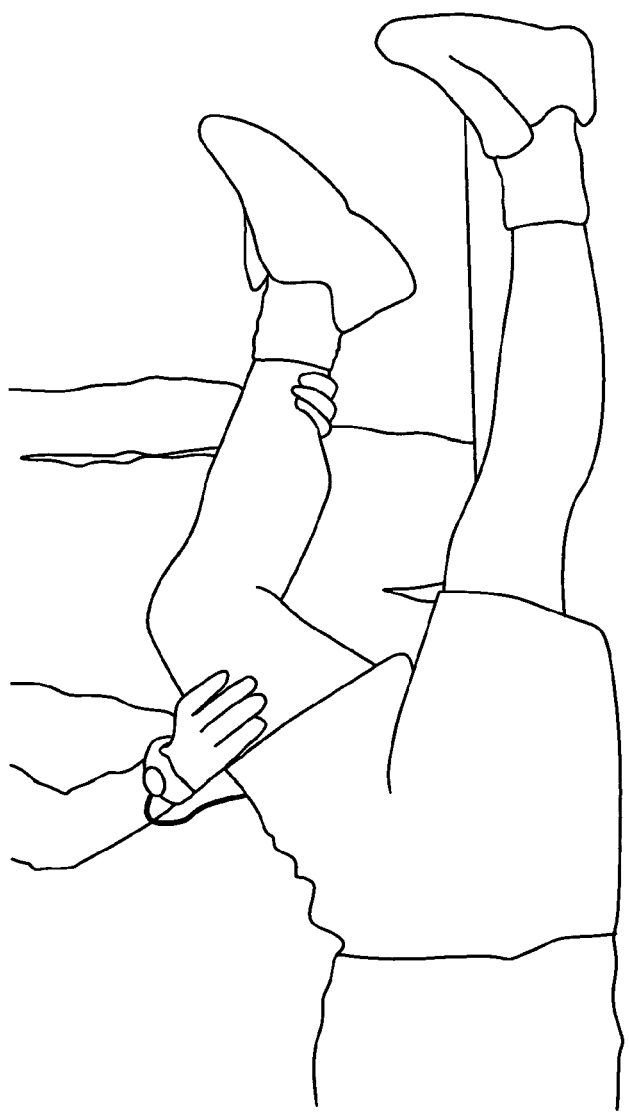
FIG. 27 illustrates a micro-electromechanical systems (MEMS) based one-dimensional gyroscope or accelerometer attached to the top of the disposable clinical glove for measuring angle of rotation of arms and legs according to an embodiment of the present invention.

One improvement according to an embodiment of the present invention uses micro-electromechanical systems (MEMS) based one-dimensional gyroscope or accelerometer attached to the top of the disposable clinical glove having the grating-based sensor where a physician may hit a button on a key board to have the data acquisition to start record rotating angle reference to the starting point when the key was hit for the leg or arm rotation as shown in FIG. 27. Note that the clinician is examining the patient on his leg rotation using the embedded gyroscope glove sensor.

Figure 28:
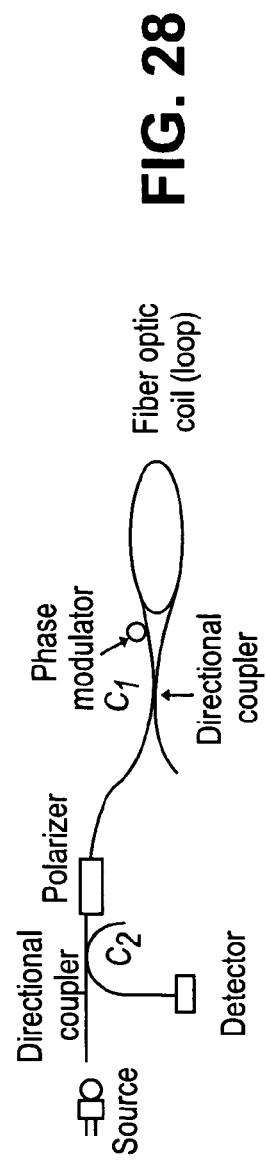
FIG. 28 illustrates a Sagnac interferometer setup for a fiber optic gyroscope to be attached to the disposable clinical glove for measuring angle of rotation of arms and legs according to an embodiment of the present invention.

An alternative improvement according to an embodiment of the present invention involves using a fiber optic gyroscope. The concept is shown in FIG. 28, which illustrates Sagnac interferometer setup and principles according to an embodiment of the present invention. Embodiments utilize a Sagnac interferometer to measure acceleration and deceleration and based on velocity differential to figure out the rotation angles of the arms and legs. The Concept of Sagnac interferometer is as follows. If the loop rotates clockwise, by the time the beams traverse the loop, the starting point may have moved and the clockwise beam may take a slightly longer time than the counterclockwise beam to come back to the starting point. This difference of time or phase may result in a change of intensity at the output light beam propagating toward $C_2$. If the entire loop arrangement rotates with an angular velocity W, the phase difference between the two beams is given by:

$$\Delta \phi = \frac{8\pi NA\Omega}{c\lambda_0}$$

where N is the number of fiber turns in the loop, A is the area enclosed by one turn (which need not be circular, and $\lambda_0$ is the free space wavelength of light.

Disposable Clinical Glove Sensor Having a Fiber Optic Evanescent Sensor(s)

Figure 29:
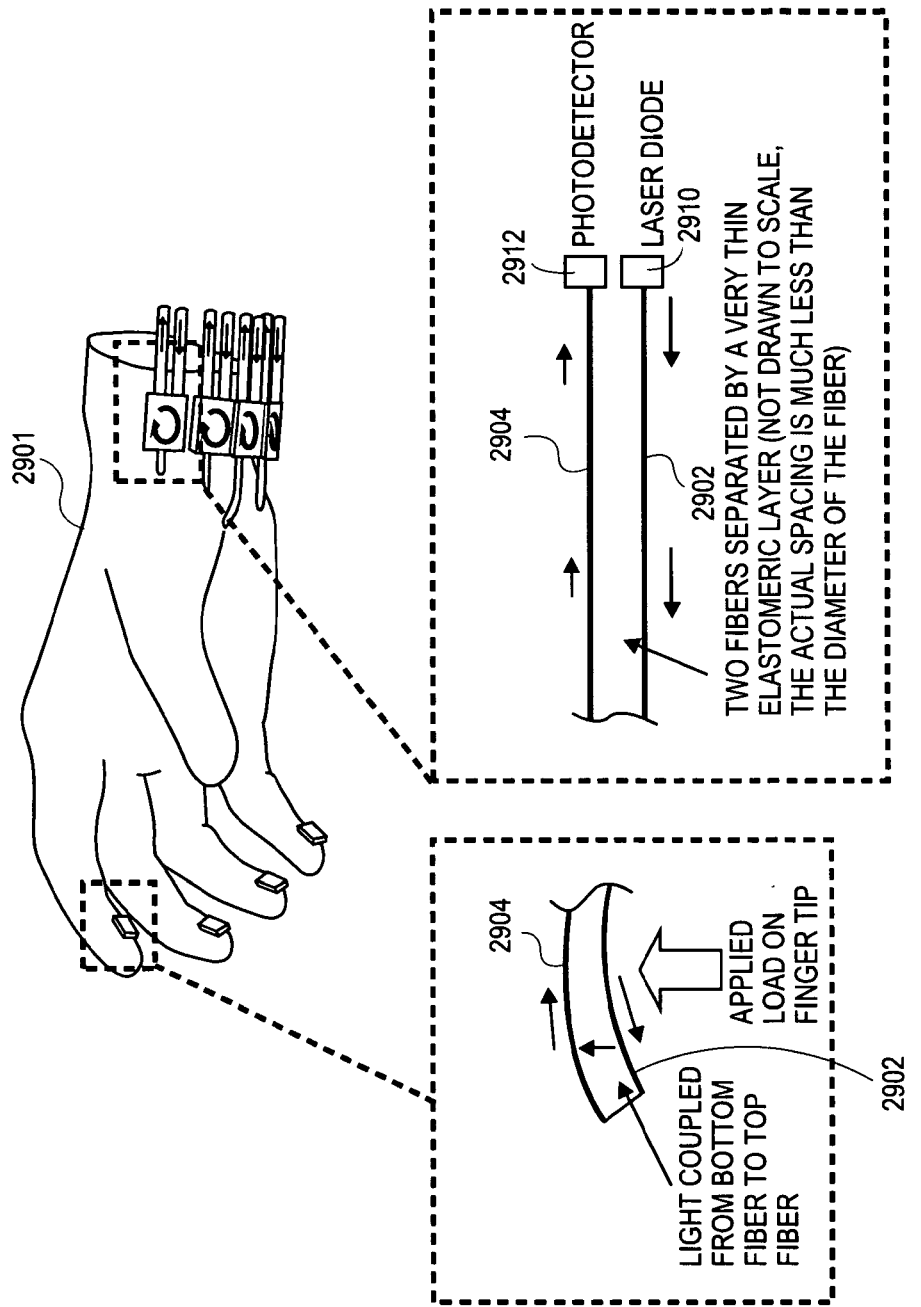
FIG. 29 illustrates a clinical sensing glove having a fiber optic evanescent sensor according to an embodiment of the present invention.

The pressure sensor for haptic tactile feedback, goniometer, and other potential applications also may be accomplished using one or more evanescent wave coupling sensors according to an embodiment of the present invention. One embodiment, illustrated in FIG. 29, includes a strain sensor 2900 disposed in a glove 2901. The sensor 2900 may or may not use an additional applicator depending on the amount of sensitivity desired. The sensor 2900 is based on light coupling between two slightly angled non-contacting multimode fibers 2902 and 2904. The sensor 2900 is fabricated by placing the two light guides 2902 and 2904 in close proximity but separated by a thin layer of matching index silicone rubber 2906. The evanescent field generated by the guiding region allows transverse coupling between the guides 2902 and 2904. The magnitude of coupled light intensity varies with the distance separation between the two guides 2902 and 2904. For multimode fibers, light may be coupled through higher order modes in cladding due to bending. For single mode fibers, light coupled is based on the hypothesis of weak coupling of evanescent wave in cladding. The coupled mode equation is given as:

$$\frac{dA_1}{dz} = -j\beta_1 A_1 + C_{12} A_2$$

$$\frac{dA_{2(1)}}{dz} = -j\beta_2 A_2 + C_{21} A_1$$

where two wave guides have equal propagation constants $\beta_1 = \beta_2$ with far field amplitudes $A_1$ and $A_2$ and C is the coupling coefficient per unit length. The two output intensities from the coupler are given by:

$$I_3 = A_1^2 (\cos C_{12} z)^2$$

$$I_3 = A_1^2 (\sin C_{12} z)^2$$

The above equations clearly show the power is transferred periodically along the z direction from one waveguide to the other. For a complete energy transfer from one waveguide to another, the coupling must be made within a coupled length $l_o$, given by $\pi/2C$. If the coupling length is less than $l_o$, only part of the energy from one wave guide may couple to the other. The coupling coefficient is given as:

$$C = \frac{2\pi}{\lambda \alpha^2} \left( \sqrt{1 - \left(\frac{n_s}{nc}\right)^2} \frac{n_c^2 - n_e^2}{(n_c^2 - n_s^2)^{3/2}} \frac{K_0 \left[ 2(A + (2\pi d)/\lambda)) \sqrt{(n_e^2 - n_s^2)} \right]}{K_1 \left[ \alpha \sqrt{(n_e^2 - n_s^2)} \right]} \right)$$

where $\alpha = 2\pi d/\lambda$. The value inside of ( ) is a constant thus the coupling coefficient is basically a function of $\alpha$, in which case, the magnitude of the coupling change with the distance separation d.

The proposed bending sensor 2900 utilizes this coupling distance for its deflection magnitude measurement. Each coupling sensor is constructed with one fiber running parallel to the adjacent fiber. One fiber is excited by a laser source 2910 while the other senses light to a photodetector 2912. The fibers 2902 and 2904 are separated by the thin layer of index matching silicone rubber or polymer 2906. When the bending occurs, light from the input fiber 2902 may coupled light into the output fiber 2904. By observing the coupled light intensity, the magnitude of bending can be deduced.

The force is measured based on the induced strain on the fiber 2902. When the sensing fiber 2902 gets bent due to finger touching something, a light attenuation occurs in the one fiber may be coupled to another fiber. The output intensity appeared at the detector end may show a proportional intensity change with respect to the applied force.

Figure 30:
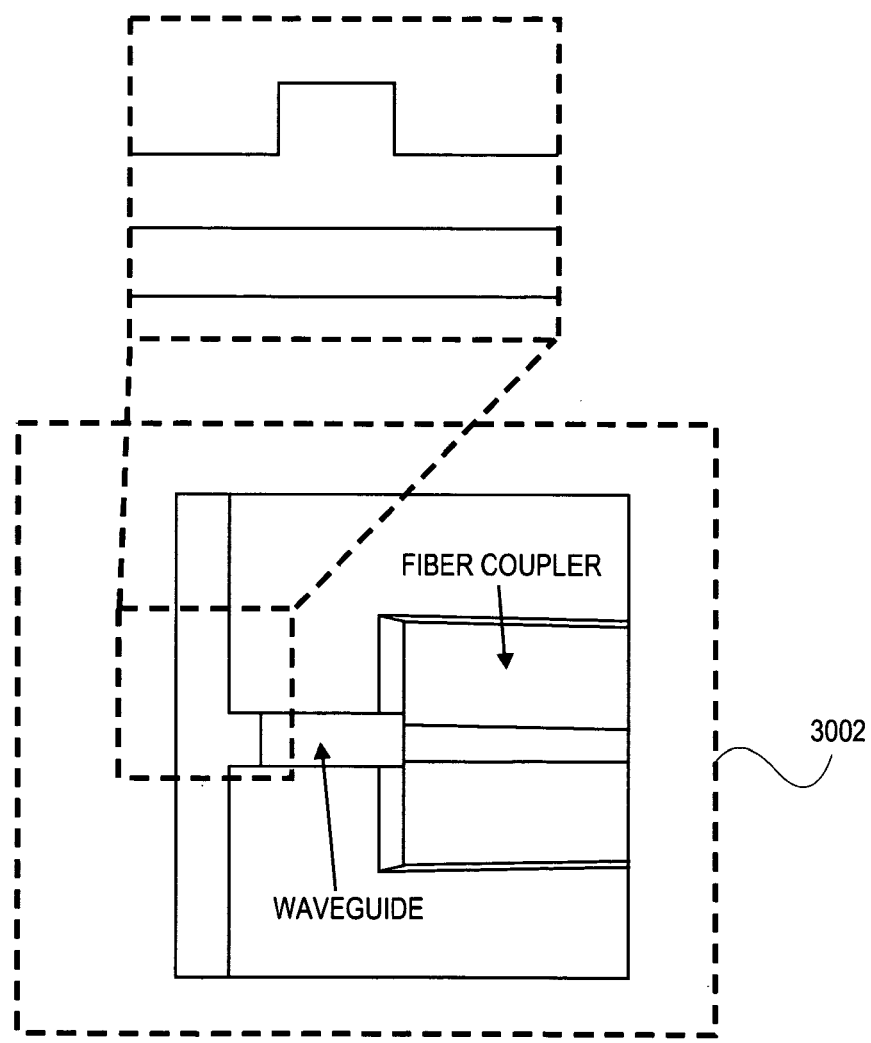
FIG. 30 illustrates a clinical sensing glove having a waveguide layer in an embedded polymeric evanescent waveguide sensor according to an embodiment of the present invention.

For a micro-fabricated version, the sensor arm of the fiber optic setup may be replaced by a micro-fabricated waveguide which may be made at the same time when the glove is made. This can be made by having the waveguide mold already embedded onto the mannequin hand which is used as the glove former. FIG. 30 depicts a waveguide layer 3002 in an embedded polymeric evanescent waveguide sensor according to an embodiment of the present invention. The resulting embedded polymeric evanescent waveguide sensor utilizes two layers of these waveguide structures 3002 sitting on top of each other. The waveguide core structures are separated by a thin layer of cladding that has slightly lower refractive index.

Figure 31:
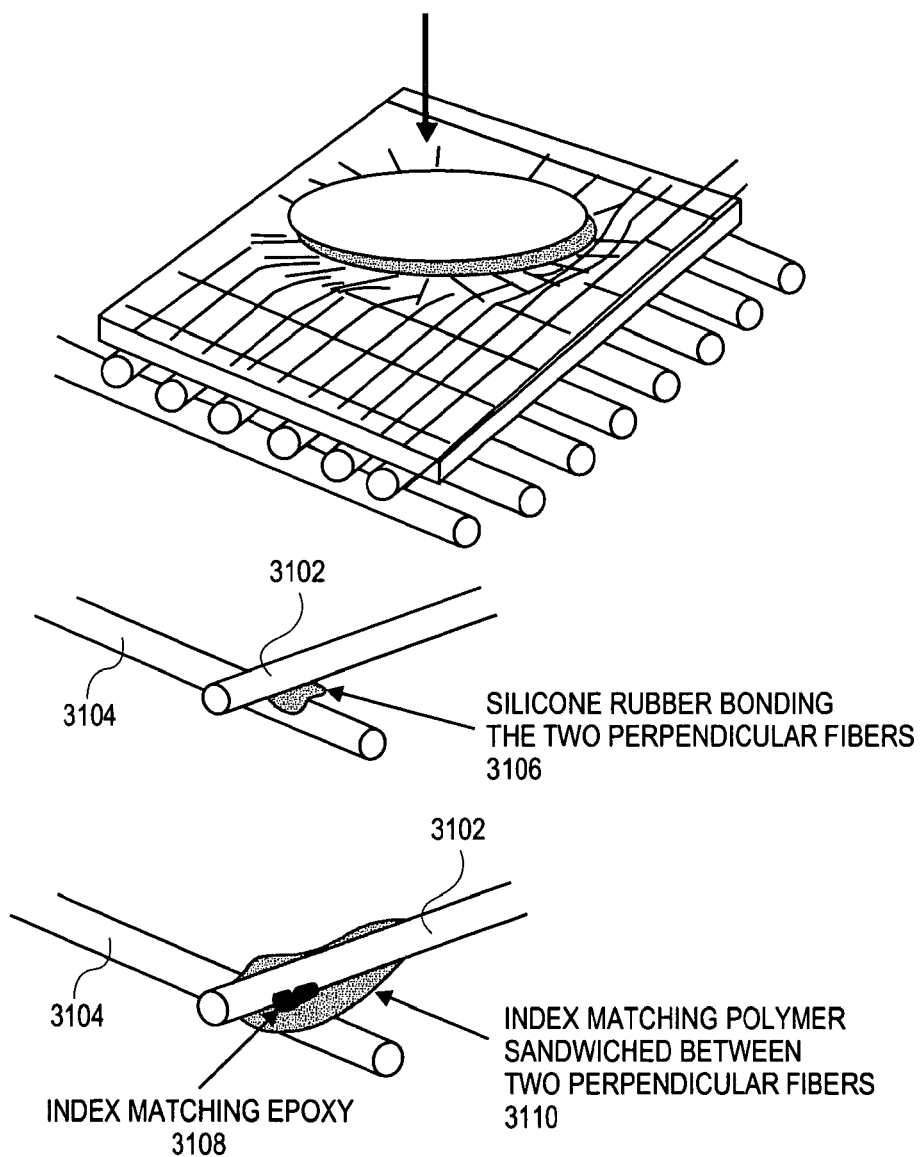
FIG. 31 depicts a distributive tactile sensor for an evanescent coupler-based sensor according to an embodiment of the present invention.

FIG. 31 depicts a tactile sensor according to an embodiment of the present invention that can provide high dexterity in the way the sensor touches. The sensor may be replacing a single sensor configuration at the finger tip. Depending on the number of the fibers used in this sensor, a data acquisition may be used to collect all the signals from the fibers. As mentioned in the design, the position and magnitude of the bend may be determined by the light coupling between the input fibers and output fibers. Light is coupled into one fiber 3102 from a second adjacent fiber 3104 due to the evanescent wave. The closer the fibers 3102 and 3104 are to each other the larger the amount of light that is coupled from one fiber to the other fiber. The output intensity may be modulated according to the distance separating the two fibers 3102 and 3104. There may be silicone rubber 3106 bonding the two perpendicular fibers 3102 and 3104. Index matching epoxy 3108 and/or index matching polymer 3110 may be sandwiched between the two perpendicular fibers 3102 and 3104.

Clinical Glove Sensor Having a Micro Ring Resonator Sensor(s)

Figure 32:
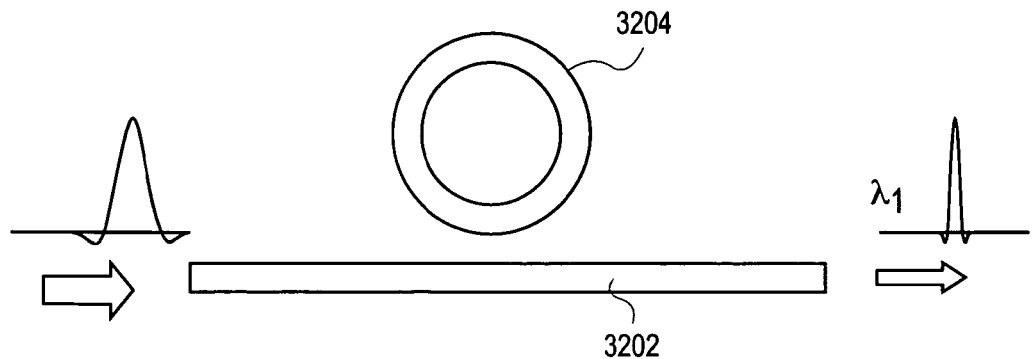
FIG. 32 illustrates a waveguide ring resonator for a ring resonator-based sensor according to embodiments of the present invention.

For some embodiments, optical sensors may be embedded or molded into a disposable clinical glove for variety of hand related force sensing, position sensing, and actuation. In one embodiment, a micro-fabricated ring resonator waveguide is utilized as a force sensor in the glove. A waveguide ring resonator according to embodiments of the present invention is shown in FIG. 32.

In the illustrated embodiment, a waveguide 3202 is and a ring resonator 3204 micro-fabricated on a semi-flexible polymer material. The ring resonator 3204 is used as the wavelength filter similar to other resonating cavities except that the ring resonator 3204 creates a very high fineness (high Q factor) in the output spectrum. The idea is to use the ring resonator 3204 as a sensor, where a broadband light source (e.g., a laser diode or LED) may be used as the input light source into the waveguide 3202. When light is coupled into the ring resonator 3204, depending on the radius of the ring resonator 3204, only a specific wavelength may be coupled out of the waveguide 3202. In some embodiments, a small smooth ball made of harder polymer is placed above the ring resonator 3204. The ring resonator 3204 may be made of semi-flexible material so that the ring resonator 3204 can stretch when an object is pressing against the ring resonator 3204. Due to the ball-induced deformation on the ring resonator 3204 substrate, the ring resonator 3204 may deform slightly. Based on the fact that $$\lambda_m = \frac{2\pi N_{\mathit{eff}} R_{\mathit{eff}}}{m}$$

different wavelengths may be coupled out to the output waveguide 3202. $N_{\mathit{eff}}$ represents effective index of the waveguide and ring structure, $R_{\mathit{eff}}$ represents effective radius of the ring 3204, defined as the radial distance to the centroid of the radial function, and m represents the $m_{th}$ order interference peak.

Figure 33:
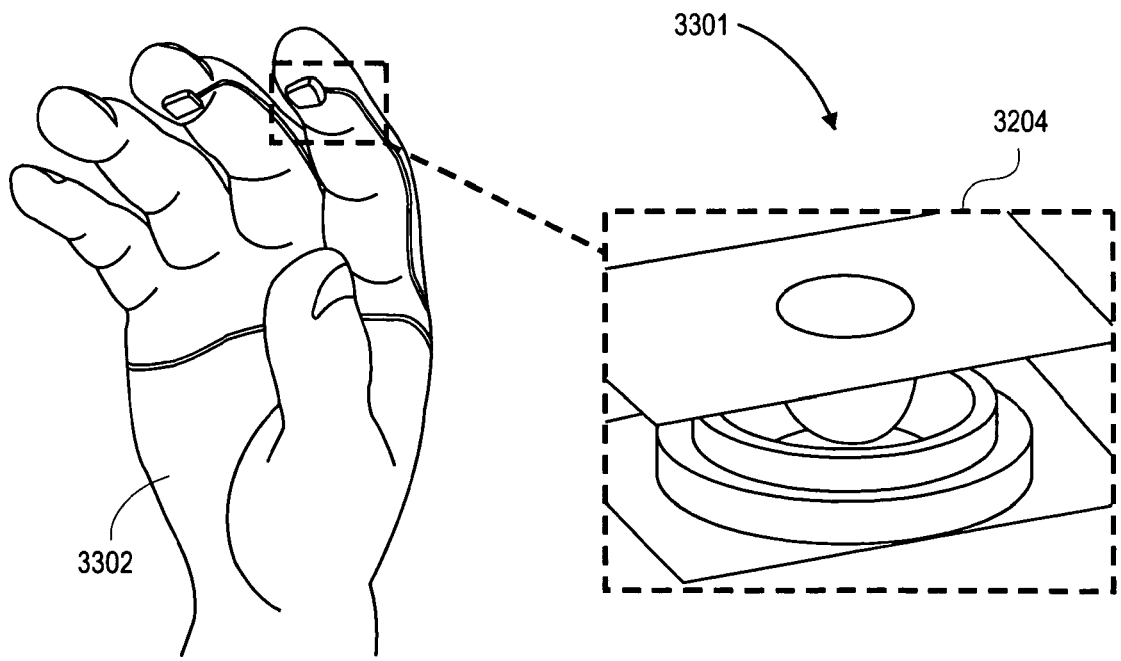
FIG. 33 illustrates a disposable clinical sensing glove having molded waveguides and a micro-ring resonator-based sensor according to an embodiment of the present invention.

FIG. 33 illustrates a disposable glove 3302 having molded waveguides and a micro-ring resonator sensor 3301 according to an embodiment of the present invention. FIG. 33 also shows a close-up view of the ring resonator 3204. When force is applied to the ring resonator 3204, the output wavelength of input light may change.

For some embodiments, the wavelength can be changed when $N_{\mathit{eff}}$ and $R_{\mathit{eff}}$ vary. By fabricating micro-rings with polymer, we are able to vary $R_{\mathit{eff}}$ by the applied force. As a result, the resonant peaks may be shifted. The half bandwidth of the detected signal power ($\Delta\lambda$) is determined by $$\Delta\lambda = \frac{2\kappa_T^2 \lambda_m^2}{(2\pi)^2 R_{\mathit{eff}} N_{\mathit{eff}}}.$$

The half-bandwidth value $\Delta\lambda$ may be as small as possible. If the effective radius $R_{\mathit{eff}}$ of the ring 3204 increases, the half-bandwidth value $\Delta\lambda$ may decrease. But an effective radius $R_{\mathit{eff}}$ increase also may lead to an increase in $\kappa_T$, which may result in an increase in the half-bandwidth value $\Delta\lambda$. Thus, this is a trade off situation and the value of effective radius $R_{\mathit{eff}}$ of the ring 3204 may be optimized.

In some embodiments, the optical set up may be similar to the interrogation system used for the grating-based interrogation system. In one embodiment, for wavelength shift detection, an optical fiber based Fabry-Perot scanning interferometer may be used. The construction of the sensor includes two mirrors directly deposited at the ends of an optical fiber to form an optical cavity. FIG. 19 described above is suitable for one interrogations system.

As described above with reference to FIG. 19, wavelength scanning may be accomplished by axially straining a short section of the optical fiber 1910 using the Fabry-Perot piezoelectric actuator 1908. In one embodiment, optical fiber based Fabry-Perot (FP) scanning interferometer may include two mirrors directly deposited to the ends of an optical fiber to form an optical cavity. Wavelength scanning may be achieved by axially straining a short section of the optical fiber by a piezoelectric actuator. As the Fabry-Perot (FP) scanning interferometer 1908 scans over the returning signals from the gratings 1912, the Bragg wavelengths $\lambda_B$ are determined and recorded from the voltage applied to the piezoelectric actuator as the return signals are detected. The phase modulation ($\Delta\phi$) induced by the Bragg wavelength shift, $\Delta\lambda_B$, is given by $\Delta\Phi = 2\pi n_f d \Delta\lambda_B / \lambda_B^2$, where $n_f$ is index of refraction of the fiber and d is the fiber cavity length.

In an alternative embodiment, an off-the-shelf fiber Bragg grating interrogation system may be used. Currently available Fabry-Perot scanners can be scanned at rates >300 Hz. The minimum resolvable Bragg wavelength shift, $\Delta\lambda_B$ for a free spectral range of forty nm (wavelength range 1525 to 1565 nm) with grating spaced by 625 pm via a sixteen bit digital to analog is around 0.6 pm, which should be sufficient to provide the speed and resolution needed for dynamic strain measurement of stress distributions.

Figure 34:
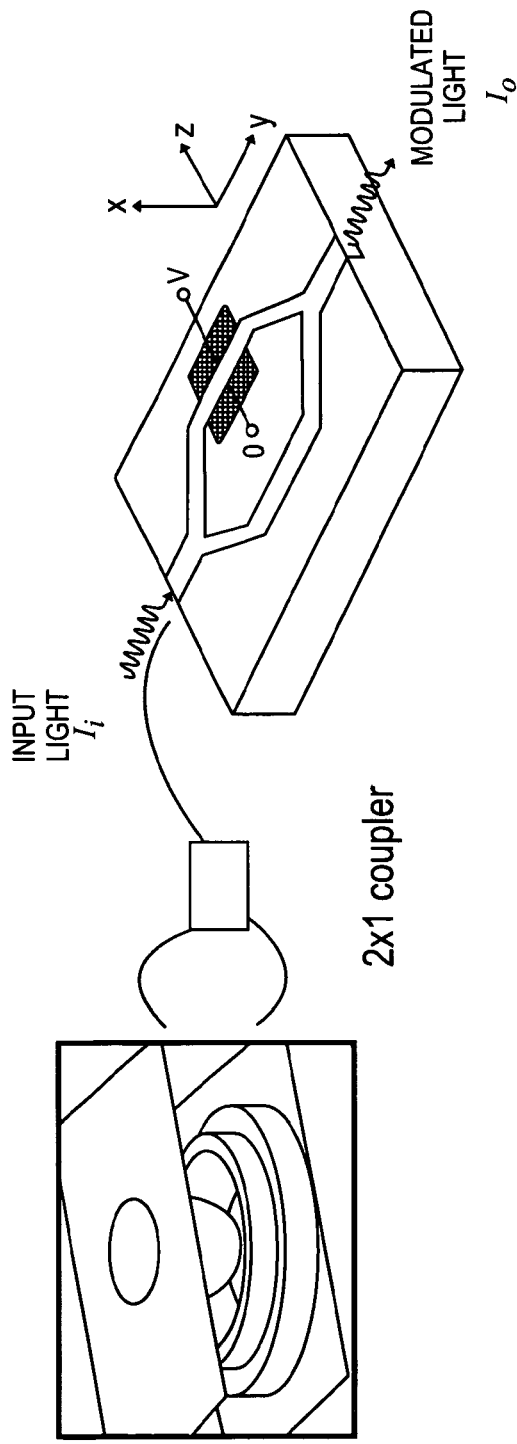
FIG. 34 is a schematic diagram of a suitable integrated electro-optic Mach Zehnder interferometer for a ring resonator-based sensor according to an embodiment of the present invention.

In other embodiments, an integrated Fourier transform spectrometer, where signal is analyzed, may be utilized. Several of the integrated Fourier transform spectrometer may be used as interrogation system. FIG. 34 is a schematic diagram of a suitable integrated electro-optic Mach Zehnder interferometer according to an embodiment of the present invention. In the illustrated embodiment, the ring resonator sensor 3301 is coupled to the integrated electro-optic Mach Zehnder interferometer 2004 via the 2×1 coupler 2006.

As described above, the Fourier transform spectrometer uses the integrated electro-optic based Mach Zehnder interferometer 2004 in which scanning is done not by moving one or more mirrors but by changing the refractive index of the optical path on one of the arms 2008 in the interferometer 2004. By doing that, the phase modulation may be controlled by the input voltage V.

The example integrated Mach-Zehnder waveguide modulator 2004 may be made of electro-optical polymer. The electro optic material includes of many ellipsoids. The longer axis is called ordinary axis and the other two axes are called extraordinary axes. In one embodiment, the polymer's extraordinary axis is aligned with z-axis, and its ordinary axes are aligned with x- and y-axes.

Other embodiments may utilize a far infrared (IR) spectrometer. For a far IR spectrometer, the waveguide arm 2008 may have a width of 1 µm and voltage V may be applied across the waveguide along z-direction, over a length of 30 mm. The wavelength of the light may be 2000 nm, the electro-optic coefficient may be $r_{33}=40\times10^{-12}$ and the refractive index may be $n_o=1.52$. With these values, the half-wave voltage $V_7$, for the transverse electric (TE) wave resolution and phase modulation due to applied voltage may be determined.

Because the phase modulation as a function of refractive index is represented as:

$$\phi = n(E)k_0 L = 2\pi n(E)L/\lambda_0$$

$$\phi_0 \equiv \frac{2\pi n L}{\lambda_0}$$

$$\phi \approx \phi_0 - \pi \frac{rn^3 EL}{\lambda_0}$$

$$E = V/d$$

$$\phi = \phi_0 - \pi \frac{V}{V_\pi}: \text{Phase modulation}$$

$$V_\pi = \frac{d}{L}\frac{\lambda_0}{rn^3}: \text{Half-wave voltage}$$

$$\delta\lambda = \frac{0.5\lambda^2}{\Delta L} \text{scanning resolution,}$$

the resulting $V_\pi=0.475$. If we input a V=100 volt, we get $\Delta\phi=661.96$ and equivalent $\Delta L=1.386\times10^{-4}$ m and the scanning resolution is 2 nm. $\phi$ is phase modulation, $\phi_0$ is the initial phase difference between sensing and reference arms, L is sensing length, E is electrical field, $\lambda_0$ is initial operating wavelength, $k_0$ is wave number in air, n is index of refraction, r is electro-optic coefficient, V is voltage, and d is thickness of the electro-optic material.

A derivation of the specific intensity $I_k(x)$ observed for input of a single wave number k gives $$I_k(x) = J(k)\langle T(k)\rangle\frac{1}{2}[1+\cos(kx)],$$

where J(k) is input intensity and T(k) is coupling efficiency.

An example of the resulting interferogram according to an embodiment of the present invention is shown in FIG. 21.

To obtain the total intensity I(x) measured for a given $\Delta L$ from input at all wave numbers is found by integrating $I_k(x)$, which is equivalent to applying an inverse Fourier cosine transform, where the Fourier cosine transform, $$\mathcal{F}_x^{(c)}[f(x)](k)=R[\mathcal{F}_x[f(x)](k)].$$

where the Fourier cosine transform is the real part of the full complex Fourier transform:

$$I(x) = \frac{1}{2}\int_0^\infty \langle T(k)\rangle J(k)dk + \frac{1}{2}\int_0^\infty \cos(kx)\langle T(k)\rangle J(k)dk\frac{1}{2}I(0) +$$

$$\frac{1}{2}\int_0^\infty \cos(kx)\langle T(k)\rangle J(k)dk\frac{1}{2}I(0) + \frac{1}{2}\mathcal{F}_c^{-1}[\langle T(k)\rangle J(k)].$$

The fact that the intensity of the white fringe (x=0) can be written $$I(x) = \int_0^\infty I_k(x=0)dk = \int_0^\infty J(k)\langle T(k)\rangle dk,$$

(x) can now be inverted for the one-sided case to yield the real spectrum $J(k)\langle T(k)\rangle = 2\mathfrak{I}_c[I(x)-\frac{1}{2}I(0)]$, which is illustrated in FIG. 22. Specifically, FIG. 22 is a graphical representation of the Fourier transform spectrometer for the above example of how the grating spectrum generated from the grating-based pressure/shear sensor on a disposable clinical glove.

Alternatively, according to other embodiments there are number of other integrated spectrometers that can be made that include fiber optic Fabry-Perot interferometers and electro-optic liquid crystal based Fourier transform spectrometers that can be used with the ring resonator sensor 3301 instead of the above Mach Zehnder interferometer technique.

Fabrication of Ring Resonator-Based Sensor(s)

According to embodiments of the present invention, a rectangular waveguide may be embedded on the surface of a disposable clinical glove. This may be done by molding the ring resonator sensor with the glove at the same time as the glove is made (as described above with reference to FIG. 30, which shows a waveguide on glove manufacturing process and/or FIG. 41, which shows the clinical glove using macro bend loss sensor. Alternatively, the rectangular waveguide may be made of separate substrate and adhered to the finger tips and palm of the glove.

An alternative embodiment to the micro-fabricated version utilizes a fiber optic micro-ring resonator structure, in which a ring structure is lithographically exposed on the surface of an optical fiber. The optical fiber then may be embedded in the disposable glove as described above for embedding other types of fiber optic sensors.

Other embodiments of making this ring structure on fiber use a D optical fiber and electroplate photoresist onto the optical fiber then utilizing photolithography to expose the ring structure onto the optical fiber. Alternative embodiments use electron beam lithography to write a ring structure on a photoresist (e.g. PMMA) layer on the optical fiber.

Figure 35:
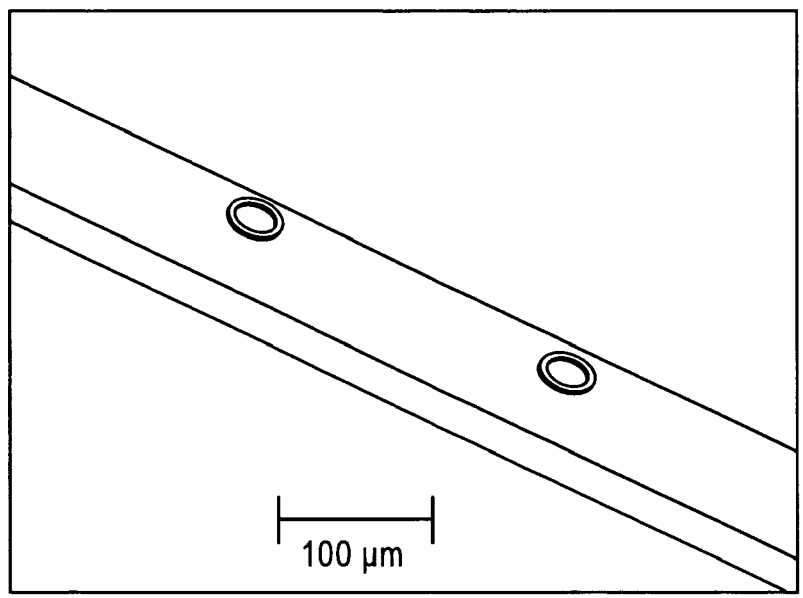
FIG. 35 is a scanning electron microscopy (SEM) rendition of a free-standing optical fiber having two micro-rings for a ring resonator-based sensor fabricated using two-photon polymerization according to an embodiment of the present invention.

Alternatively still, a three-dimensional micro-fabrication process based on two-photon polymerization may be used to fabricate the ring resonator-based sensor. Two-photon polymerization uses ultra-short laser pulses that are focused into the volume of a photosensitive material (or photoresist). The pulses initiate two-photon polymerization via two-photon absorption and subsequent polymerization. After illumination of the desired structures inside the photoresist volume and subsequent development, the polymerized material remains in the prescribed three-dimensional form. FIG. 35 is a scanning electron microscopy (SEM) of a free-standing optical fiber 3502 having two micro-rings 3504 and 3506 on the polished flat fabricated using two-photon polymerization according to an embodiment of the present invention.

Disposable Clinical Glove Having Polarimetric Sensor(s)

For some embodiments, optical sensors embedded into a disposable glove for haptic tactile feedback, goniometer, and other potential applications may include polarimetric sensors. A polarimetric sensor according to embodiments of the present invention utilizes the relative change in the optical path length between the two orthogonally polarized modes. In one embodiment, a single-mode high birefringence (Hi-Bi) optical fiber may be utilized in the polarimetric configuration. The technique is attractive, as polarimetric sensors are considerably easier to construct than their better-known interferometric-sensor counterparts yet they maintain almost the same sensitivity (2 orders of magnitude lower). The twin mode propagation also provides a higher immunity to environmental and laser phase noise than the ordinary interferometers, which is helpful when measuring temperature-dependent force parameters.

Figure 36:
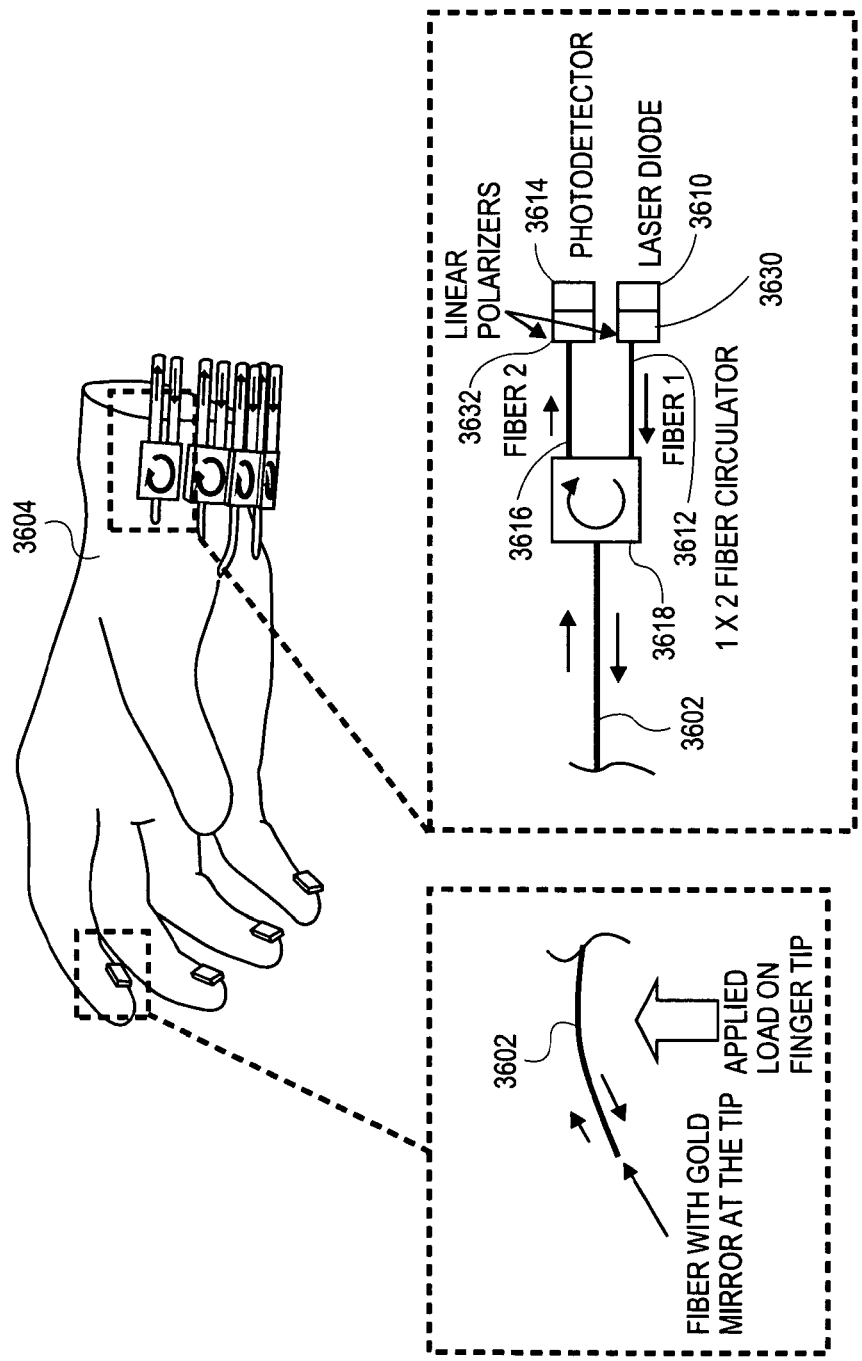
FIG. 36 illustrates a disposable clinical sensing glove having a polarimetric sensor disposed thereon according to an embodiment of the present invention.

FIG. 36 illustrates a disposable clinical glove having a polarimetric sensor according to an embodiment of the present invention. The polarimetric sensor may or may not use an additional applicator depending on the amount of sensitivity desired. In the illustrated embodiment, a fiber optic probe 3602 is embedded in fingertips of a glove 3604. The sensor 2900 may or may not use an additional applicator depending on the amount of sensitivity desired. The probe 3602 may include an optical fiber 3603 having a gold mirror at its tip. On the wrist portion of the glove 3604 is a laser diode 3610 coupled to a linear polarizer 3630, which is coupled to an optical fiber 3612. Also on the wrist portion a photodetector 3614 is coupled to a linear polarizer 3632, which is coupled to an optical fiber 3616. The optical fiber 3612 and the optical fiber 3616 are coupled to a 1×2 fiber circulator 3618, which is coupled to the optical fiber 3602. The optical fiber 3612 and the optical fiber 3616 may be polarization maintaining optical fibers. An individual fingertip and/or palm sensor may be coupled to an individual 1×2 fiber circulator. One or more of the finger tips and/or palm of the glove 3604 may include an applicator, such as the applicators illustrated in FIG. 25 above.

In one embodiment, the amplitude of force may be obtained by monitoring the shift in polarization of the optical signal reflected from the optical fiber 3606 with the changes in the birefringence of a fiber optic probe 3602. In this embodiment, the measurand is the strain induced by the load on the fiber optic probe 3602. Here, force measurement can be amplified by having the force applicator 1302 (e.g. heart rate monitoring or sound). The birefringence resulting from an applied strain field change is given as ΔB, where ΔB is a function of difference in the photo elastic effect (stress induced index change) between the two polarization Eigen modes and geometric change. The phase change due to the temperature or strain modulation can be expressed as $$\delta\phi = \frac{2\pi\delta l \Delta B}{\lambda},$$

where λ is wavelength of the input light source, δl is sensing length, and the resulted output intensity is given as $$I = \frac{1}{2}[1 + |\gamma|\cos(\delta\phi)].$$

The birefringence of the bow-tie fibers 3612 and 3616 can be calculated using the stress optic law by determining the stress condition at the center of the fiber cores. The description of the stress state is an approximation and may be of sufficient accuracy to determine the birefringence, but may not be suitable for analyzing and characterizing optical sensors. For some embodiments, the birefringence as a function of temperature and strain is given by:

$$\Delta B_{temp} = -\frac{2CE(T-T_c)}{\pi(1-v)}(\alpha_2 - \alpha_1)\left(\ln\left(\frac{b}{a}\right) - \frac{3}{4}(b^4 - a^4)\right)\sin(2\varphi_b)$$

and $$\Delta B_{strain} = -\frac{2CE\varepsilon}{\pi(1-v)}(v_2 - v_1)\left(\ln\left(\frac{b}{a}\right) - \frac{3}{4}(b^4 - a^4)\right)\sin(2\varphi_b)$$

respectively, where $\alpha_1, \alpha_2$ are the thermal expansion coefficients of the cladding and the bow-tie material regions, and $\alpha_1 - \alpha_2 = -1.14\times10^{-6}/°$ C., $v_1, v_2$ are the Poisson ratios of the cladding and bow-tie region where $v=v_1$ is the Poisson ratio of the optical fiber core, $T_c=900°$ C. is the setting temperature, T is the ambient temperature (variable), C is the stress optic coefficient and $C=-3.36\times10^{-6}$ mm$_2$/N E is the Young's Modulus of the optical fiber (E=7.83×10$^{10}$ N/m$^2$), $\phi_b=45°$ is the angle of the bow-tie, ε is the axial strain (variable), a=0.056 and b=0.36 are the normalized radius from the fiber axis to the beginning of the bow-tie and the radius from the fiber axis to the end of the bow-tie, respectively. These values are valid only for bare fiber where the temperature is assumed constant over the entire fiber cross section and for uni-axial strain in the direction of the fiber. Also, temperature and elastic properties are assumed constant in the fiber cross section and only the variation of the Poisson ratio is assumed to contribute to the birefringence.

The proposed polarimetric sensor setup shown in FIG. 36 may operate as follows. Light from the un-polarized diode laser 3610 emitting in the IR region (e.g. 1300 or 1550 nm) is launched into the input end of the fiber 3612 through the linear polarizer 3630. The polarizer 3630 is used to rotate the plane of polarization of the input light beam at 45° or 135° with respect to the principal axes of the input fiber of the 2×1 fiber coupler 3618. This excites the two orthogonal Eigen axes equally. The output from the coupler 3618 is connected to the optical fiber 3602 used as the sensing fiber. The sensing fiber 3602's surfaced end is coated with a deposited gold thin film as mirror, where the mirror provides the reflection of the signal to the detector 3614. The displacement of the fiber 3602 is measured based on the intensity variation created by the strain-induced birefringence effect of the sensor fiber 3602. Using this relationship, the force applied on the finger tip is detected based the phase modulation due the birefringent effect. The fiber rotator 3618 is used to allow light to travel only from input fiber 3612 to sensor fiber 3602 and then to detector fiber 3616. No light may be coupled into detector fiber 3616 when light is input from sensor fiber 3602. This is to prevent any interference between the input light and the reflected light occurred at sensor fiber 3602. The polarizer 3632 at the detector 3614 is used as an analyzer. The optical components are made with receptacle style connectors that allow optical components to snap on easily.

The polarimetric sensor may operate in two regimes. One regime is a linear regime, in which the induced perturbation is small. This implies that the elongation of the sensor fiber 3602 is kept small so that the resulting output is therefore a varying intensity pattern which depends on the parameter being measured, and the fringe pattern should be absent to keep the phase change δφ less than π/2.

Figure 37:
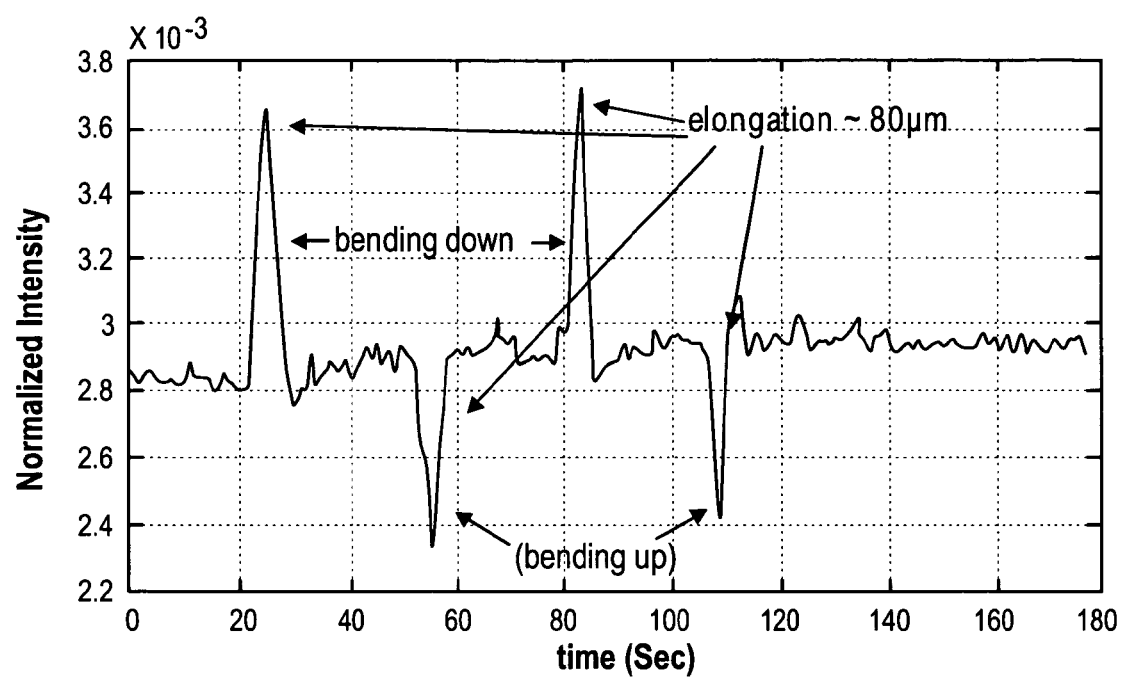
FIG. 37 illustrates an example of a dynamic load on a polarimetric sensor according to an embodiment of the present invention.

A second regime is a nonlinear range in which large perturbations force the output into the nonlinear range, thereby inducing fringes. Most fiber-optic sensors, being highly sensitive, operate in this mode and a fringe counting technique needs to be used to process the output signal. However, the magnitude of the bending required for the fringe counting technique to be useful in this set-up may be far too great (>10 cm or 530N for 15 fringes). Based on this condition, the first technique was may be more suitable. In the detection scheme for a strain sensor, it may be desirable to monitor both the amplitude and the direction of a dynamically varying strain. In the vibration of a cantilever beam, one may want to measure the amplitude of the vibration as well as to indicate whether the strain on parts of the beam is tensile or compressive. An example of dynamic load on the sensor according to an embodiment of the present invention is shown in FIG. 37.

Figure 38:
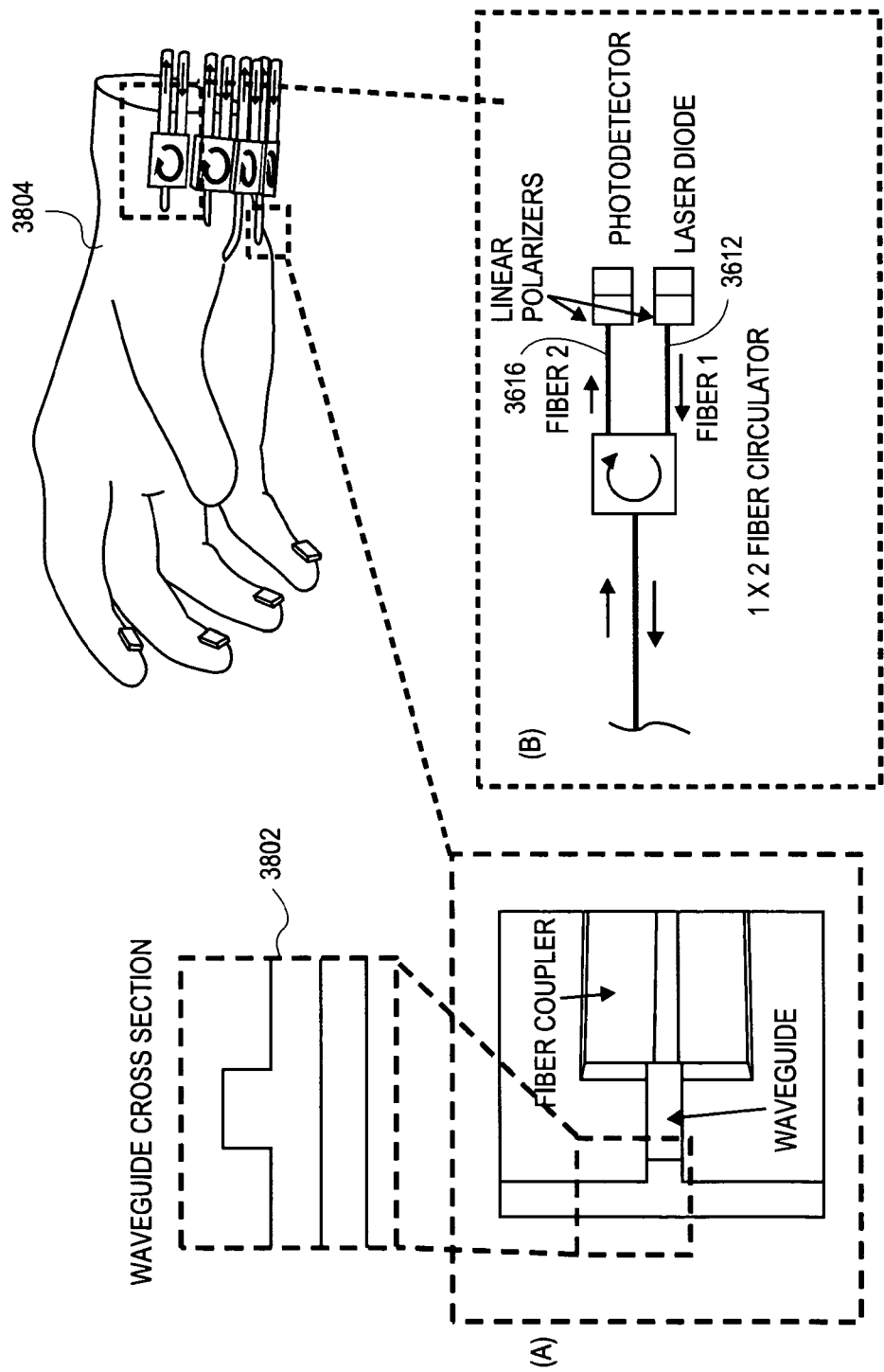
FIG. 38 illustrates another view of a disposable clinical glove having a polarimetric sensor according to an embodiment of the present invention.

FIG. 38 illustrates another view of a disposable clinical glove with a polarimetric sensor according to an embodiment of the present invention. The illustrated embodiment includes a micro-fabricated waveguide 3802, which may be made at the same time when a glove 3804 is made. This can be made by having a waveguide mold already embedded onto a mannequin hand, which is used as the glove former. FIG. 38 shows example of what the waveguide 3802 might look like near the interconnect between the input fiber 3612 and the micro-fabricated waveguide 3802 on the glove 3804.

Disposable Clinical Glove Having Phase Modulation Sensor(s)

Figure 39:
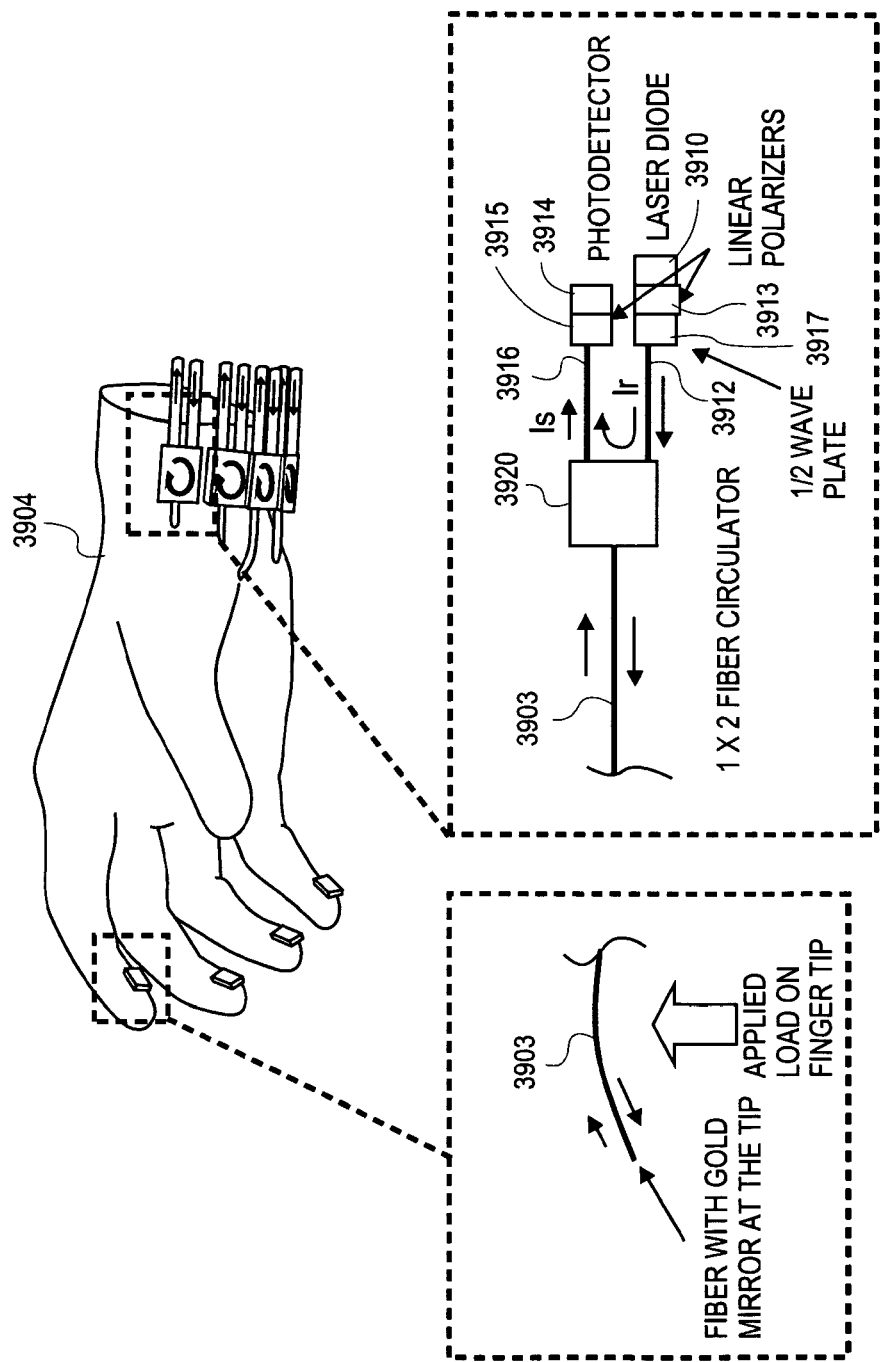
FIG. 39 illustrates a Michelson interferometer application for a phase modulation-based sensor in a disposable clinical glove according to an embodiment of the present invention.

For some embodiments of the present invention, optical sensors embedded into a disposable glove for haptic tactile feedback, goniometer, and other potential applications may include phase modulation sensors. A phase modulation sensor according to embodiments of the present invention utilizes a Michelson interferometer technique for force, pressure, sound, and/or hardness measurement. The sensor may or may not use an additional applicator depending on the amount of sensitivity desired. A Michelson interferometer application according to an embodiment of the present invention is shown in FIG. 39. In the illustrated embodiment, a fiber optic probe 3902 is embedded in fingertips of a glove 3904. The probe 3902 may include an optical fiber 3903 having a gold mirror at its tip. On the wrist portion of the glove 3904 is a laser diode 3910 coupled to an optical fiber 3912, which is coupled to a linear polarizer 3913. Also on the wrist portion of the glove 3904 is a photodetector 3914 coupled to a linear polarizer 3915, which is coupled to a half-wave plate 3917. The half-wave plate 3917 is coupled to an optical fiber 3916. The optical fiber 3912 and the optical fiber 3916 are coupled to a 1×2 fiber circulator 3918, which is coupled to the optical fiber 3902. An individual fingertip and/or palm sensor may be coupled to an individual 1×2 fiber circulator.

The illustrated Michelson interferometer sensor utilizes the relative change in the optical path length between the incident and reflected beam due to an elongation or optical index change in the optical fiber 3903. Here, the optical fiber 3903 is a single-mode polarization maintaining optical fiber. The Michelson interferometer sensor is attractive because it is highly sensitive to the strain induced on the optical fiber 3903. Therefore is it chosen for the force sensor.

Figure 40:
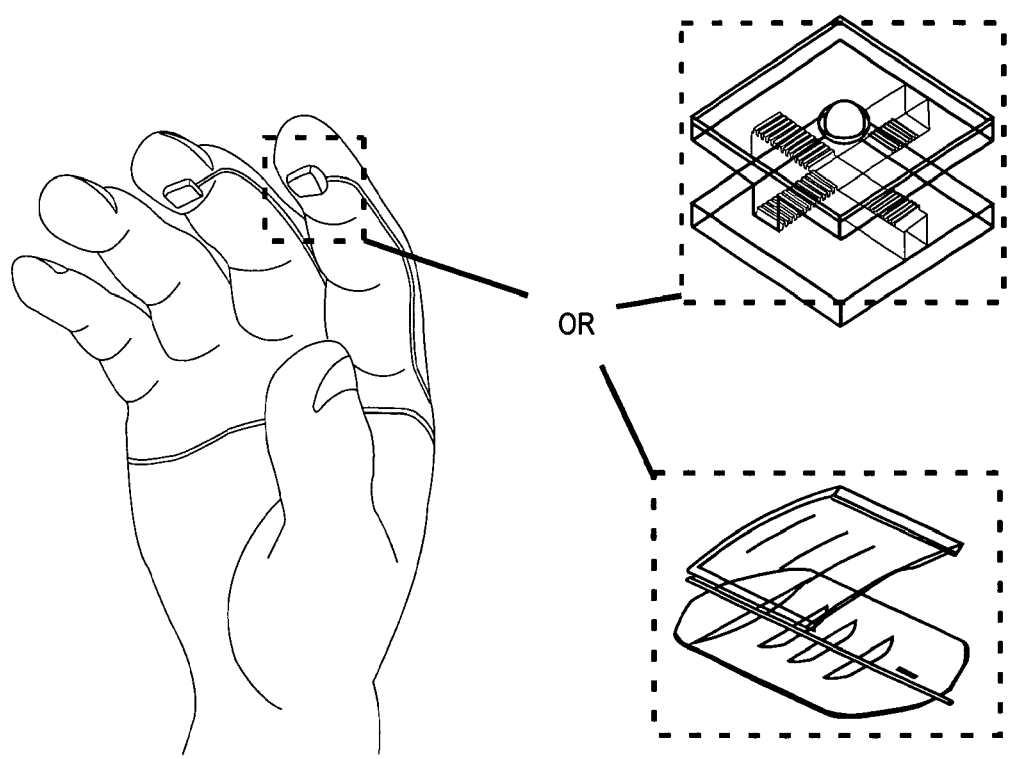
FIG. 40 illustrates a force applicator for a phase modulation-based sensor according to an embodiment of the present invention.

For some embodiments, the amplitude of force may be obtained by monitoring the shift in optical path length of the reflected signal with respect to the incident intensity of the fiber optic probe 3902. The measurand is the strain induced by the load applied transversely near the tip of the fiber optic probe 3902. Here, force measurement may be amplified by having a force applicator as shown in FIG. 40 (e.g. heart rate monitoring). The phase modulation resulting from an applied strain field change is given as $\Delta\phi$, where $\Delta\phi$ is a function of the difference in the photo elastic effect and physical geometry change of the optical fiber 3903.

Based on that, the bend induced phase shift may be written as $\Delta\phi = k\Delta L + L\Delta k$, where the first term $k\Delta L$ corresponds to the change in the optical fiber 3903's length and the second term $L\Delta K$ corresponds to the photo elastic effect. When strain configuration is taken into account, the first term represents the effect of the physical change of length due to the strain becomes $\Delta\phi = k_o n S_1 \Delta L$, where S is the strain vector and the subscript 1 of the strain vector refers to the longitudinal direction, i.e., along the optical fiber 3903's axis, in this case x direction. The transverse components 2 or 3 of the optical indicatrix are equivalent here because of the radial symmetry. The strain vector may be different depending on the difference in stress.

The second term, the change in phase due to a change in k, come about from two effects: the strain-optic effect whereby the strain changes the refractive index of the fiber, and a wave guide mode dispersion effect due to a change in fiber diameter produced by strain:

$$L\Delta k = L\frac{dk}{dn}\Delta n + L\frac{dk}{dD}\Delta D.$$

The strain-optic effect whereby the strain changes the refractive index of the fiber 3903 when light is propagating in the axial direction (x direction) of the fiber 3903 is expressed as $$\Delta n = -\frac{1}{2}n^3 \Delta\left(\frac{1}{n^2}\right)_{x,y,z}.$$

Based on the theory, the propagation constant is $k=nk_o$, and hence $$\frac{dk}{dn} = k_o.$$

The strain-optic effect appears as a change in the optical indicatrix $$\Delta\left(\frac{1}{n^2}\right)_i = \sum_{i=1}^{6}\rho_{ij}S_j$$

where μ is the Poisson's ratio. The strain ϵ is related to the applied pressure P by the value of Young's modulus, E, in the form of $\epsilon = -P/E$. Without shear strain, $S_4, S_5, S_6 = 0$, we only need to considered i, j=1, 2, 3 elements of the strain-optic tensor for a homogeneous isotropic material. For an isotropic medium, $\rho_{ij}$ has only two numerical values, designated $\rho_{11}$ and $\rho_{12}$.

When values are plugged in, the effect by the change in diameter is relatively small than the other two terms by two or three orders of magnitude. Therefore, the bend induced phase shift is reduced to length change and photo elastic effect $$\Delta \phi = k_o n S_1 \Delta L - \left(\frac{1}{2}\right) L k_o n^3 \sum_{i=1}^{6} \rho_{ij} S_j$$

$$\begin{aligned} I &= \langle E_r^2 \rangle + \langle E_s^2 \rangle + 2\langle E_r E_s \rangle \\ &= I_r + I_s + 2(I_r I_s)^{0.5} \cos(\Delta\phi) \\ &= I_o[\alpha_r k_f k_b + \alpha_s(1-k_f) + 2\sqrt{\alpha_r \alpha_s k_f k_b (1-k_f)} \cos(\Delta\phi)] \end{aligned}$$

Where < > denotes a time average over a period >$2\pi/\omega_o$, $\alpha_r$ and $\alpha_s$ are optical losses associated with reference and signal paths and $k_f$, $k_b$ are associated with coupling coefficients with light traveling forward and back from the sensor 3903.

The setup illustrated in FIG. 39 features an input channel, an output channel, and a sensor channel. The input channel includes the laser diode 3910, the linear polarizer 3913, the half-wave plate 3917, and the optical fiber 3912. The output channel includes the photodetector 3914, the linear polarizer 3915 and the optical fiber 3916. The sensor channel includes the optical fiber 3903 and the embedded sensor. The laser diode 3910 is used as a monochromatic light source. The combination of the polarizer 3913 and a half-wave plate 3917 placed in front of the laser diode 3910 are used to avoid the reflected light from interfering with the input light by changing the reflected light from linearly polarized to circularly polarized. Light entering from the input channel splits at the 1×2 coupler 3920, where the reference light gets channeled to the output fiber 3916 and the other portion of the light continues to the sensing fiber 3903. The light in the sensor channel continues its journey until it reaches the mirror at the end of the fiber 3903, where the majority of the light gets reflected. Once the reflected light reaches the coupler 3920, again the light splits into two where one goes to the detector 3914 and it combines with the reference light and forms the interference as we expected and the other is coupled to the input channel, where it is eventually dissipated.

Force may be measured based on the induced strain on the fiber 3903. When the sensing fiber 3903 gets bent due to a finger touching something, a phase shift occurs between the reference and sensing arms. The phase shift as described earlier may be proportional to the bending profile which in turn is proportional to the applied force.

For small forces, no applicator may be needed and the phase shift may be kept at less than $\pi/2$ to keep the operation within the linear region as described in polarimetric sensor. If larger force measurement is desired, the sensor may operate at the nonlinear region similar to the polarimetric sensor. In the nonlinear range in which large perturbations of force are applied, the output goes into the nonlinear range, thereby inducing fringes.

If the applied force is too small to be detected without an applicator, such as monitoring sound or heart beat, then force measurement can be amplified by having a force applicator as shown in FIG. 40, where the teeth and/or the ball of the applicator can increase the bending on the fiber 3903 to induce a larger phase shift.

Figure 41:
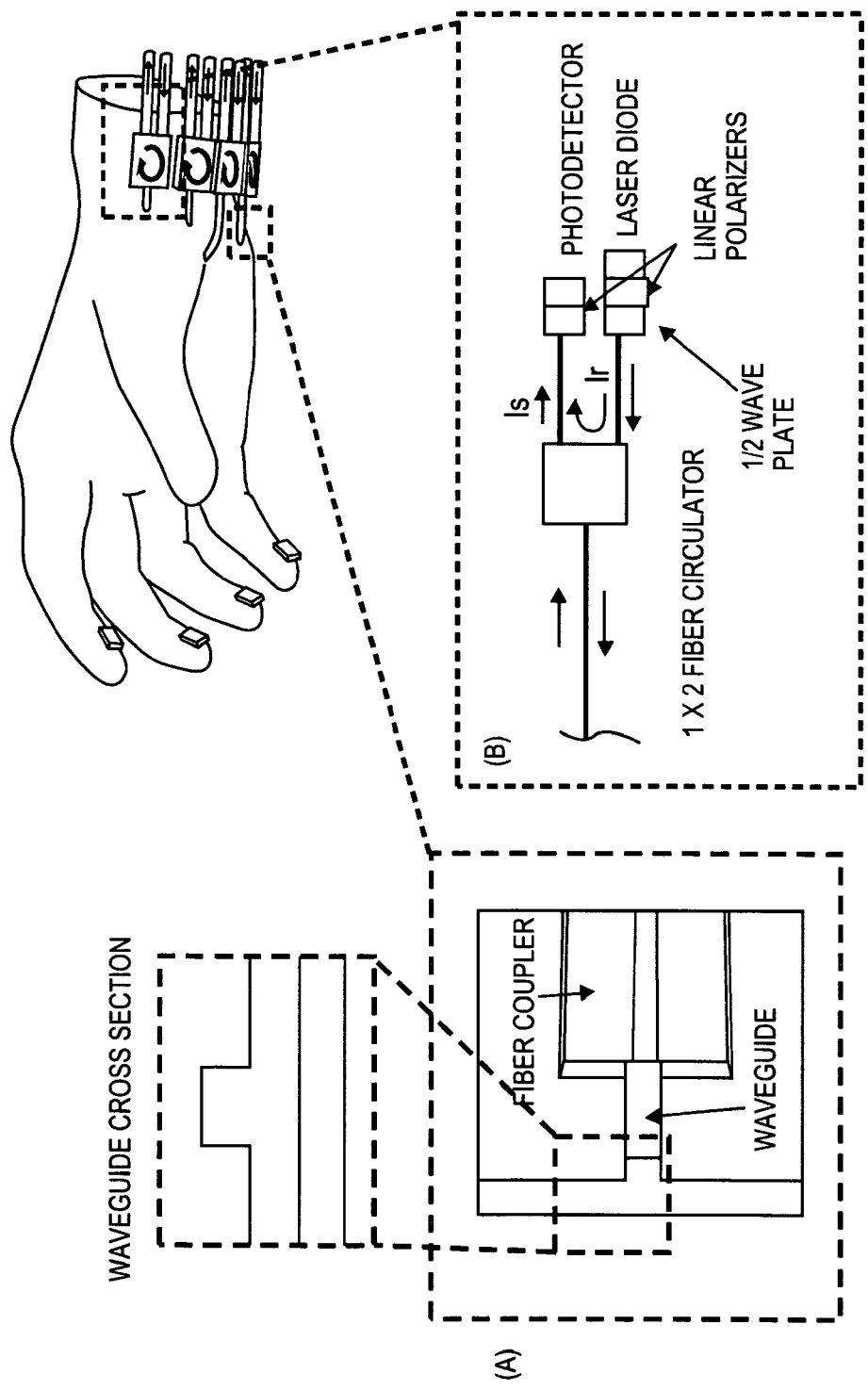
FIG. 41 illustrates an example waveguide near an interconnect between an input fiber and a micro-fabricated waveguide for a phase modulation-based sensor according to an embodiment of the present invention.

For a micro-fabricated embodiment, the sensor arm of the fiber optic setup may be replaced by a micro-fabricated waveguide, which may be made at the same time when the glove 3904 is made. The sensor may or may not use an additional applicator depending on the amount of sensitivity desired. This can be accomplished by having the waveguide mold already embedded onto a mannequin hand, which is used as the glove former. An example embodiment of what the waveguide might look like near the interconnect between the input fiber and the micro-fabricated waveguide on the glove is shown in FIG. 41.

Disposable Clinical Glove Having Macro-Bend Loss Sensor(s)

For some embodiments of the present invention, optical sensors embedded into a disposable glove for haptic tactile feedback, goniometer, and other potential applications may include macro bend loss sensors. A macro bend loss sensor according to embodiments of the present invention utilizes micro-fabricated and fiber optic based sensors.

Figure 42:
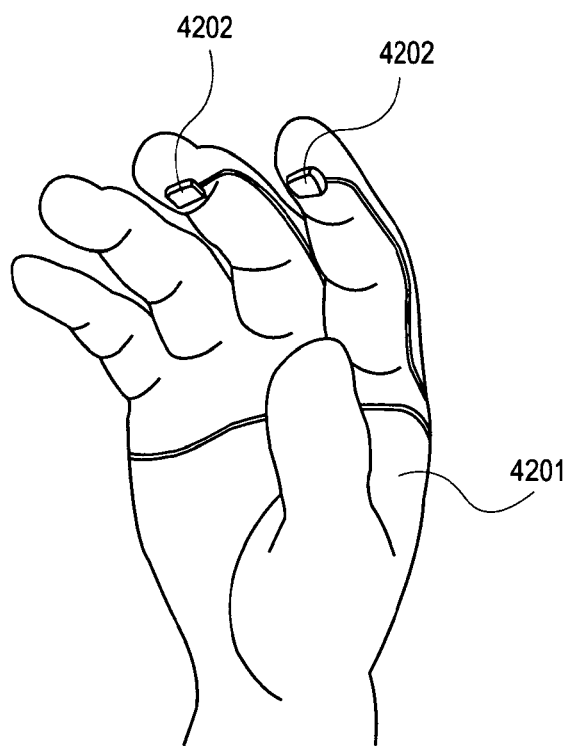
FIG. 42 illustrates a disposable clinical sensing glove having a macro bend-loss sensor according to an embodiment of the present invention.

FIG. 42 illustrates a disposable clinical glove 4201 according to an embodiment of the present invention. At least one sensor 4202 is embedded in the glove 4201.

For some embodiments, a sensor may be embedded into a glove either in a fiber-optic configuration or micro-fabricated configuration. FIG. 42 depicts the embedded micro-fabricated waveguide intensity modulated sensor. A fiber optic version may be similar except micro-fabricated waveguides may be replaced by optical fibers.

Various glove materials can be embedded. These glove materials may be Latex, Polyurethane, silicone rubber, nitrile rubber, PVC rubber, vinyl rubber and Neoprene Rubber. Most of these materials are transparent in the visible or IR band (e.g. latex n~1.58 @ 415 nm, silicone n~1.397 @ 1.55 um, polyurethane n~1.6 @ 600 nm). Therefore, the waveguide sensor and glove could be manufactured at the same time using a single mold where the mold has both waveguide and glove formers. However, if needed, silicone, PMMA or polyurethane-based materials may be used to fabricate the waveguide sensor on top other types of rubber glove substrates after glove is made.

The force measurement is derived from the bend-loss from the optical waveguides; as the sensor is loaded, the waveguide is bent and the light intensity in the waveguide is attenuated. The operating principle of the bend-loss sensor depends on the transmission power loss caused by the energy in the evanescent field. Light at a bend inside a waveguide exceeds the velocity of light propagating inside a straight waveguide and hence it can no longer be guided, which causes light energy to be radiated away from the waveguide. The light intensity attenuation coefficient $\alpha$ has the form of $\alpha = C_1 \exp(-C_2 R)$, where $C_1$ and $C_2$ are constants that depend on the dimensions of the waveguide and on the shape of the modal fields, and R is the radius of curvature of the waveguide. The two constants can be determined by measuring the attenuation at two predefined bending radii. A more rigorous derivation of the above equation using a slab waveguide structure can be found by the ratio of the power lost into the air over power transmitted in the waveguide. Applying the effective index method to our waveguide structure in FIG. 42, an equivalent waveguide bend loss can be expressed as $$\alpha = \gamma \frac{\cos^2(ha) \exp\left(\frac{2(\beta_z - \beta_o)R}{\gamma \beta_o}\right) \exp\left(\frac{a\lambda_1}{\gamma}\right)}{\left(\frac{a}{2} + \frac{1}{2h}\sin(ha) + \gamma \cos^2\left(\frac{ha}{2}\right)\right) a^2},$$

where a is the width of the waveguide, $\lambda_1$ is the wavelength in the medium surrounding the waveguide, R is radius of curvature of the bend, $\beta_o$ is the propagation constant of unguided light in air, $\beta_z$ is the propagation constant in the waveguide at radius R, h and $\gamma$ are real and imaginary parts of the propagation constant along the width direction, respectively. Thus the radiation loss depends exponentially on the radius of curvature of the waveguide; as the waveguide is bent, light is attenuated. Other factors that can be adjusted to increase the radiation loss during bending include decreasing: 1) the propagation constant of the waveguide compared to that of its surrounding materials, 2) the width of the waveguide and 3) the height to width aspect ratio of the waveguide. Note that $$\alpha = \gamma \frac{\cos^2(ha)\exp\left(\frac{2(\beta_z-\beta_o)R}{\gamma\beta_o}\right)\exp\left(\frac{a\lambda_1}{\gamma}\right)}{\left(\frac{a}{2}+\frac{1}{2h}\sin(ha)+\gamma\cos^2\left(\frac{ha}{2}\right)\right)a^2}$$

holds true for waveguides with square cross sections.

Figure 43:
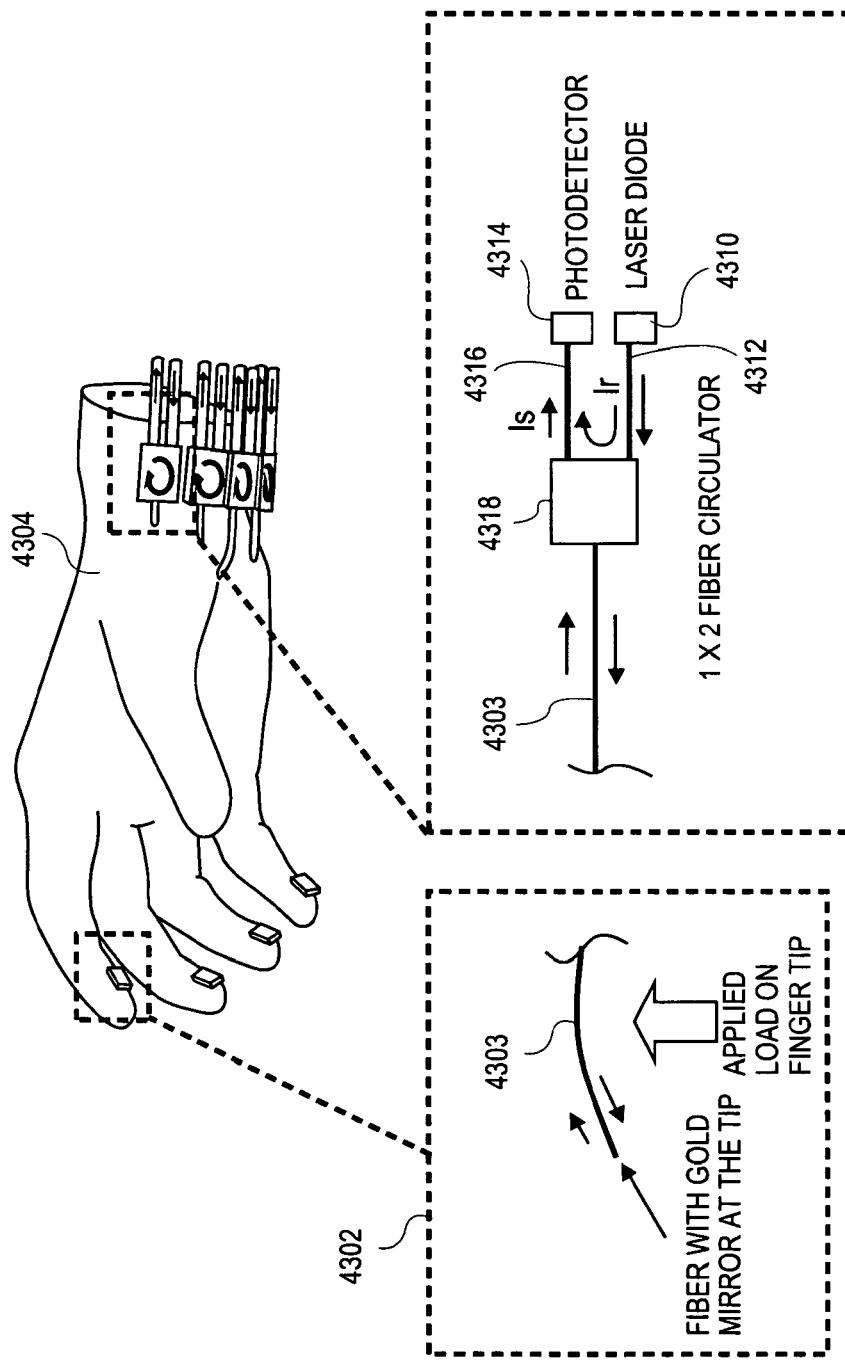
FIG. 43 illustrates a fiber optic configuration for a macro bend-loss sensor according to an embodiment of the present invention.

The equation $\alpha = C_1 \exp(-C_2 R)$ applies for a fiber optic sensor as well. A fiber optic configuration according to an embodiment of the present invention is illustrated in FIG. 43. In the illustrated embodiment, a fiber optic probe 4302 is embedded in fingertips of a glove 4304. The probe 4302 may include an optical fiber 4303 having a gold mirror at its tip. On the wrist portion of the glove 4304 is a laser diode 4310 coupled to an optical fiber 4312. Also on the wrist portion a photodetector 4314 is coupled to an optical fiber 4316. The optical fiber 4312 and the optical fiber 4316 are coupled to a 1×2 fiber circulator 4318, which is coupled to the optical fiber 4302. An individual fingertip and/or palm sensor may be coupled to an individual 1×2 fiber circulator.

The setup illustrated in FIG. 43 features an input channel, an output channel, and a sensor channel. The input channel includes the laser diode 4310 and the optical fiber 4312. The output channel includes the photodetector 4314 and the optical fiber 4316. The sensor channel includes the optical fiber 4303 and the embedded sensor. The laser diode (or LED) 4310 is used as a light source.

Light entering from the input channel splits at the 1×2 coupler 4320, where the reference light gets channeled to the output fiber 4316 and the other portion of the light continues to the sensing fiber 4303. The light in the sensor channel continues its journey until it reaches the mirror at the end of the fiber 4303, where the majority of the light gets reflected. Once the reflected light reaches the coupler 4320, again the light splits into two where one portion goes to the detector 4314 and it combines with the reference light and forms the interference as we expected and the other portion of the reflected light is coupled to the input channel, where it is eventually dissipated.

The force is measured based on the induced strain on the fiber 4302. When the sensing fiber 4302 is bent due to a finger touching something, light attenuation occurs in the fiber 4302. The output intensity appearing at the detector 4314 end may show a proportional intensity change with respect to the applied force.

Figure 44:
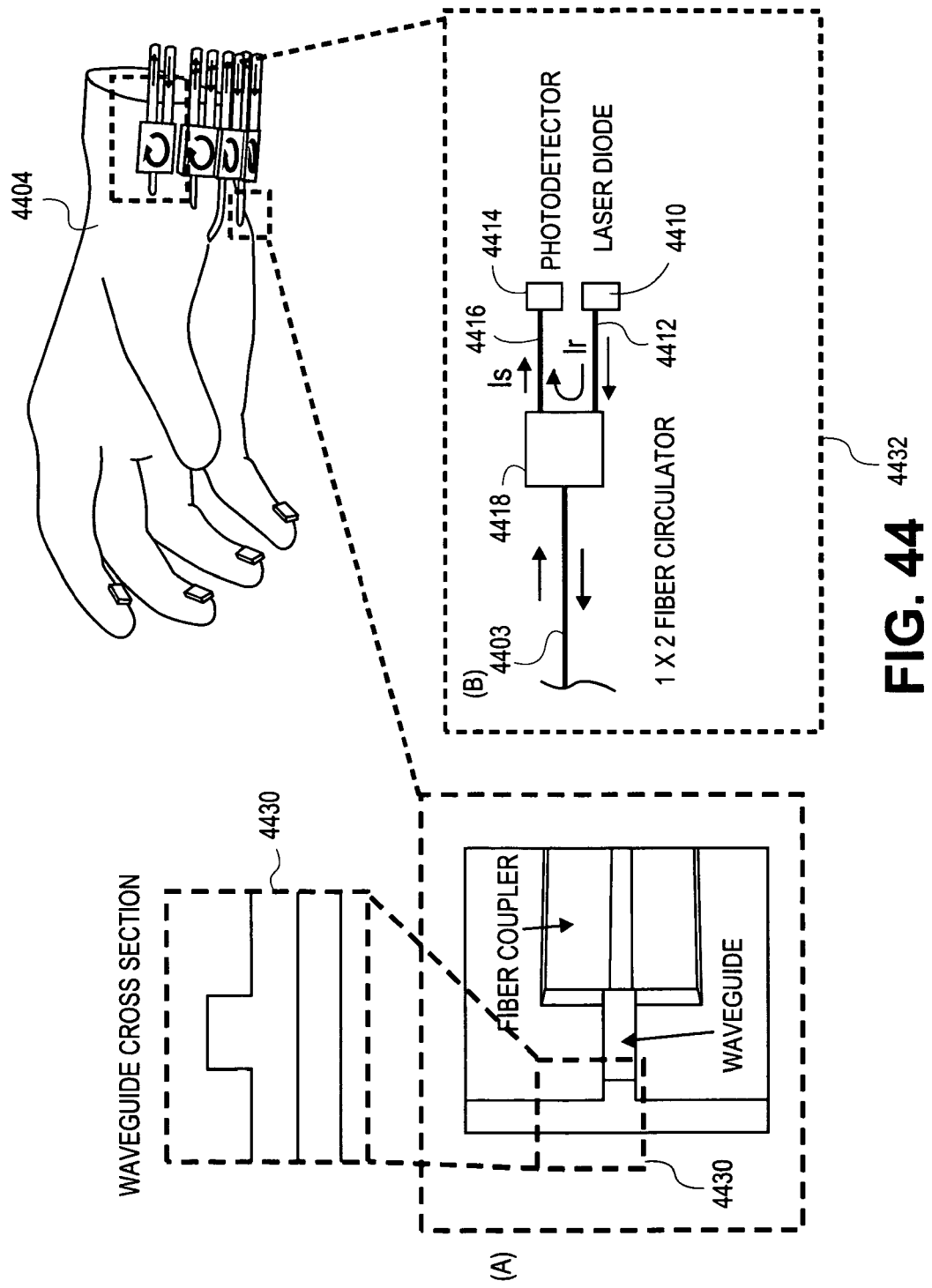
FIG. 44 illustrates an example of what a waveguide might look like near the interconnect between an input fiber and a micro-fabricated waveguide for a macro bend-loss sensor on a glove according to an embodiment of the present invention.

For embodiments implementing micro-fabricated waveguides, the sensor arm of the fiber optic setup may be replaced by a micro-fabricated waveguide which may be made at the same time when the glove is made. This can be made by having the waveguide mold already embedded onto the mannequin hand that is used as the glove former. The sensor may or may not use an additional applicator depending on the amount of sensitivity desired. An example of what the waveguide might look like near the interconnect between the input fiber and the micro-fabricated waveguide on the glove according to an embodiment of the present invention is shown in FIG. 44. In the illustrated embodiment, the micro-fabricated waveguide 4430 also is shown in cross-section along with a Michelson interferometer 4432.

Fabrication of Disposable Clinical Glove Having Macro Bend Loss Sensor(s)

Figure 45:
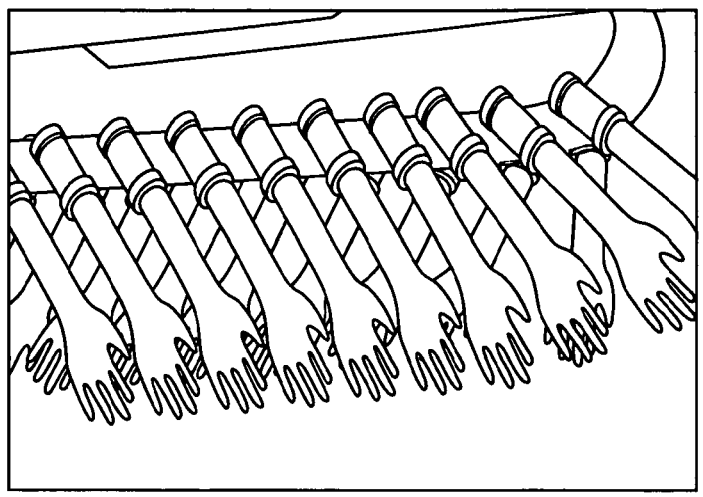
FIG. 45 illustrates glove formers being inspected and cleaned before molds are dipped into coagulant tanks according to an embodiment of the present invention.
Figure 46:
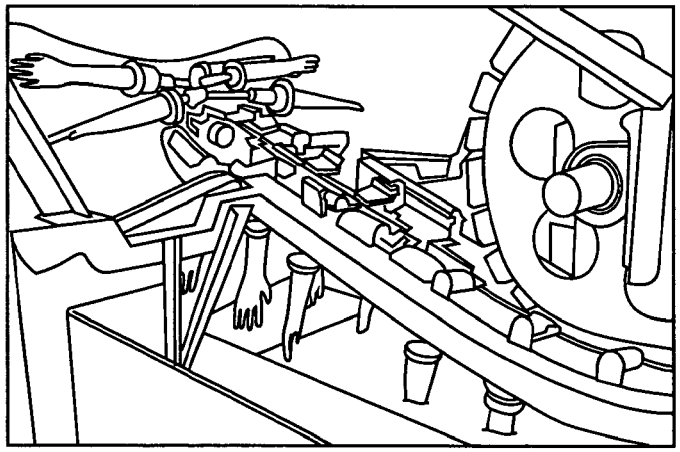
FIG. 46 illustrates glove formers dipped into a coagulant bath according to an embodiment of the present invention.
Figure 47:
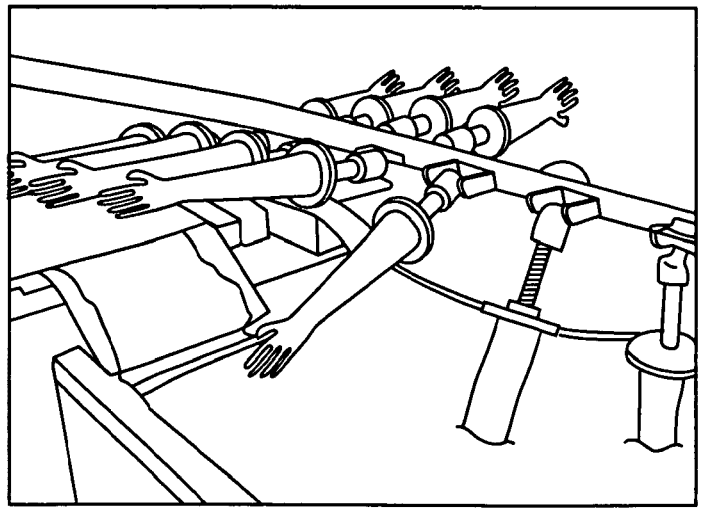
FIG. 47 illustrates gloves put through a leaching line according to an embodiment of the present invention.

For waveguide sensors that don't require force applicator, two fabrication processes may be used. In one embodiment, direct fabrication of the waveguide on the glove may be used. An example of the fabrication is shown in FIG. 44. In this embodiment, a latex-based glove with a sensor is constructed at the same time. First the rectangular waveguide or rib waveguide mold is fabricated. There are several techniques that can be used to fabricate the mold. An excimer laser may be used to directly engrave the rectangular (or close to rectangular shape) groove into a mannequin hand using a three-dimensional controlling stage system. The resolution of the excimer laser should be sufficient for fabricating the waveguide dimensions. Another direct mechanism for disposing the waveguide mold onto the glove former according to an embodiment of the present invention is to electrode-deposit a layer of UV sensitive polymer on the mannequin hand and then expose the waveguide pattern on the UV sensitive polymer. A third mechanism for disposing the waveguide mold into the glove former according to an embodiment of the present invention is to deposit UV sensitive silicone rubber on a rubber glove after the glove has been made but still on the glove former and lithographically expose the waveguide pattern on the glove. Several types of patternable silicone rubber such as PDMS are currently available for commercial use. Once the waveguide trench is made on the glove former, a typical glove making process can be used. A typical latex glove fabrication process is shown in FIGS. 45-47.

Figure 48A:
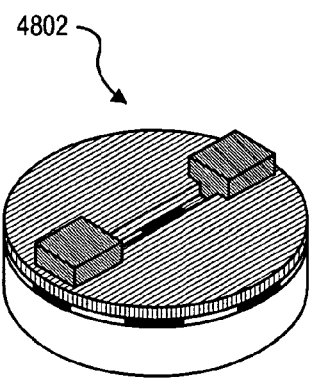
FIG. 48(a) illustrates a three-layer SU-8 mold for a macro bend-loss sensor according to an embodiment of the present invention.
Figure 48B:
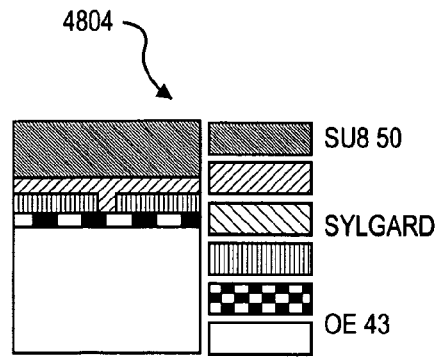
FIG. 48(b) illustrates a cross-section of an SU-8 mold having a two-layer elastomeric casting for a macro bend-loss sensor according to an embodiment of the present invention.

In an alternative embodiment, a silicon rubber waveguide may be fabricated first and then adhered to a glove. The fabrication process may involve casting a two-layered PDMS structure from a three layered SU8 mold as shown in FIG. 48. FIG. 48(a) illustrates a three-layer SU-8 mold according to an embodiment of the present invention and FIG. 48(b) illustrates a cross-section of the SU-8 mold having a two-layer elastomeric casting according to an embodiment of the present invention.

Figure 49A:
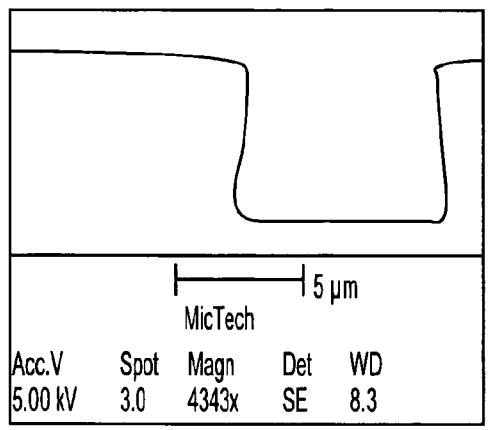
FIG. 49(a) illustrates an SU8 waveguide trench cross section for a macro bend-loss sensor according to an embodiment of the present invention.
Figure 49B:
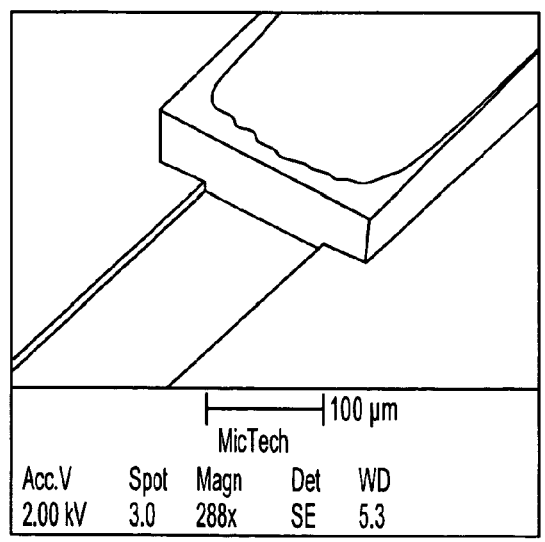
FIG. 49(b) illustrates an SU8 coupler bump and a tapering 125 µm wide waveguide trench for a macro bend-loss sensor according to an embodiment of the present invention.

In some embodiments, the SU8 mold includes a rectangular waveguide trench and a fiber coupler mount, as illustrated in FIG. 49. In the illustrated embodiment, FIG. 49(a) shows an SU8 waveguide trench cross section and FIG. 49(b) shows an SU8 coupler bump and a tapering 125 μm wide waveguide trench. In one embodiment, the waveguide may eventually taper down from 125 μm to a final 10 μm width.

For the SU8 mold substrate, a p-type single sided polished silicon wafer was used. The substrate was cleaned by immersing a diluted hydrofluoric acid (HF) (10:1) solution to remove any naturally grown oxide layer. The wafer was then rinsed thoroughly in deionized (DI) water, blown dry using nitrogen gas, and then dehydrated in an oven at 110° C. for at least 30 minutes. In order to create a good adhesion between the SU8 and the silicon wafer, a thin layer (2 μm) of SU8-2002 (Micro-Chem, MA.) was spin coated onto the silicon substrate, following instructions provided by the MicroChem. Corp.

To fabricate a waveguide trench, a 10 μm SU8-2010 resist was spun on top of the SU8-2002 layer. In order to reduce the intrinsic stress that occurred during prebaking, the temperature was ramped from 22° C. to 65° C. at a rate of 3° C./min and held at that temperature for a minute before continuing ramping to the recommended temperature of 95° C. The sample was then held at that temperature for 2 minutes before gradually ramping down to room temperature at a rate of 2° C./min.

The waveguide trench pattern may be transferred from a quartz mask to the film by exposing the film on a contact aligner with a mercury broadband light source. Based on repeated trials, it was found that the film reproduces features best when exposed at 130 mJ/cm$^2$.

For the post exposure bake, the film was placed on a hotplate for 30 minutes at 60° C. This temperature was much lower than the post bake temperature of 95° C. recommended by the manufacturer. This greatly reduced the internal stress, which may be discussed in more detail in the result and discussion section. After cooling the film to room temperature, the film was then developed in SU8 developer (PGMEA, an ethyl lactate and diacetone alcohol, MicroChem, Corp. MA.) for about 2 minutes with mild agitation.

For the coupler parts, SU8 50 (MicroChem. Corp., MA.) may be to create two large rectangular shaped plateaus. The process is basically similar to the procedure described earlier for SU8-2010. For SU8 50, a 58.5 μm (actual average resulting height ~56.2 μm) thick film is spun on top of the SU8-2010 layer. The film may be prebaked on a hotplate. The temperature may be ramped from 22° C. to 65° C. at 3° C./min and held for 7 minutes before ramping up to 95° C. The temperature may be held for 23 minutes and then ramped down to 22° C. at a rate of 2° C./min. The film may then be exposed with a coupler pattern from the quartz mask at 370 mJ/cm$^2$, and then post exposure baked at 60° C. for 30 minutes.

The whole wafer may then be immersed in SU8 developer for 6 minutes and 30 seconds. At this point, a 3-layer SU8 waveguide mold is completed, as illustrated in FIG. 49. To accommodate higher tolerance of coupling, the width of the waveguide trench may be purposely made to the size of optical fiber diameter of 125 μm, as illustrated in FIG. 49(*b*). The 125 μm waveguide may then be tapered down to the final 10 μm waveguide width, as illustrated in FIG. 49(*a*). The resulting waveguide trench may appear slightly curved.

For elastomer casting, different two-part silicone elastomers from two vendors were used: OE 43 (n=1.417 @ λ=1.55 μm from Gelest Inc.) for the core and Sylgard 184 (n=1.398 @ λ=1.55 μm from Dow Corning) for the cladding. The refractive indices of transverse electric (TE) and transverse magnetic (TM) polarizations for both elastomers were found to be the same. Based on the measurement, the optical property of the material may appear to be isotropic.

Figure 50A:
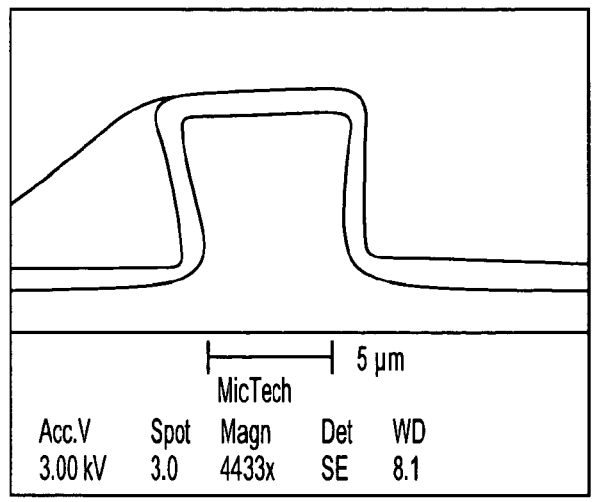
FIG. 50(a) illustrates a cross section of a PDMS waveguide for a macro bend-loss sensor according to an embodiment of the present invention.
Figure 50B:
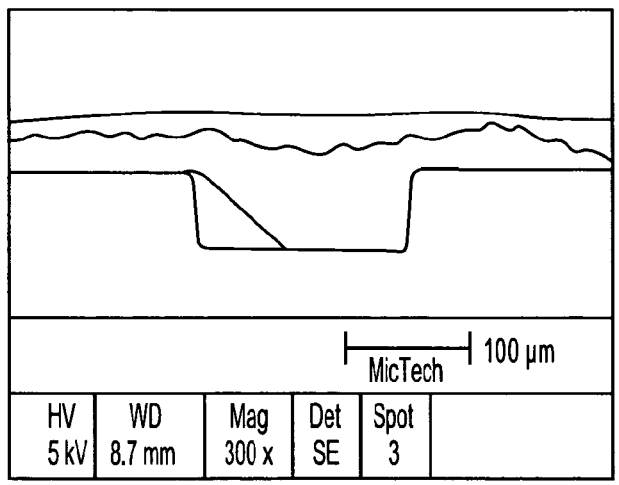
FIG. 50(b) illustrates an elastomeric coupler trench for a macro bend-loss sensor according to an embodiment of the present invention.
Figure 50C:
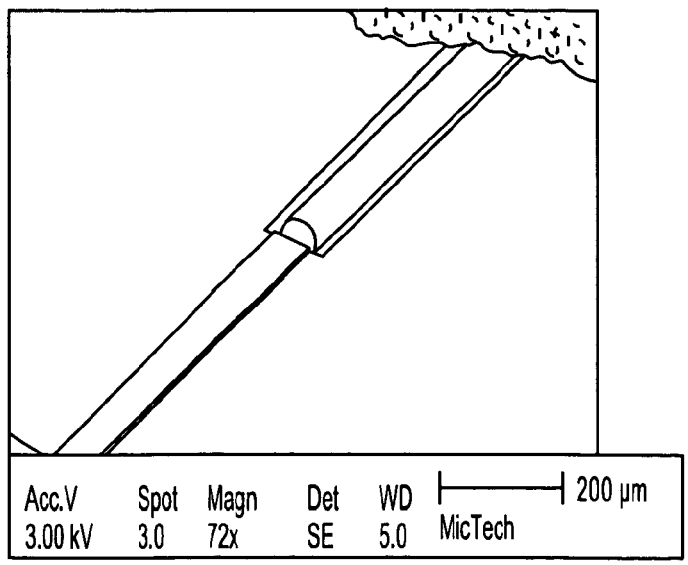
FIG. 50(c) illustrates a fiber inside the coupler for a macro bend-loss sensor according to an embodiment of the present invention.

In order to release the elastomer from the mold, the mold was first silanized by exposing the film to the vapor of (Tridecafluoro-1,1,2,2-Tetrahydrooctyl) trichlorosilane (Gelest, Inc.) in a vacuum chamber for 30 minutes. Both elastomers come with a two-part kit: a prepolymer and a curing agent. Both elastomers also utilize the same preparation steps: mix base and curing agent thoroughly with a ratio of 10:1 and then degas the air bubbles generated during mixing. For the core layer, the OE 43 was spun at 5500 rpm creating a 5 μm thick film. The film was then cured at 60° C. for 4 hours on a hotplate and then Sylgard 184 (~500 μm thick) was cast on top of OE43 and cured at 60° C. overnight in an oven. Then, in one embodiment, the elastomer was carefully separated from the mold to form the finished rib waveguide structure shown in FIG. 50, here FIG. 50(*a*) shows a cross section of a PDMS waveguide according to an embodiment of the present invention, FIG. 50(*b*) shows an elastomeric coupler trench according to an embodiment of the present invention, and FIG. 50(*c*) shows the fiber inside the coupler according to an embodiment of the present invention.

Returning to FIGS. 45-47 in which a latex glove fabrication process according to embodiments of the present invention is shown, FIG. 45 shows glove formers being inspected and cleaned before the molds are dipped into coagulant tanks according to an embodiment of the present invention. FIG. 46 shows an embodiment of the present invention in that once cleaned, the glove formers are dipped into a coagulant bath to help the latex mixture adhere to the formers and help ensure the latex is distributed evenly. The coagulant tank stage determines the thickness of the latex exam glove. The thicker the disposable gloves are to be, the longer the formers may travel in the coagulant tank. The formers are dipped into the latex mixture and may eventually travel through a series of ovens to dry the gloves. The latex mixture may have different formulations depending on the brand of clinical examination gloves being made. This liquid concoction is comprised of latex sap and chemicals that determine the elasticity of the medical glove.

FIG. 47 shows an embodiment in which after drying the latex mixture, the gloves are put through a leaching line to remove residual chemicals and proteins from the surface of the gloves. A good leaching line should be long, so latex proteins can be more effectively washed out. The water should also be hot and fresh to dissolve proteins better. This step helps to minimize the occurrence of latex sensitivity.

Waveguide Manufacturing Techniques

For some embodiments, the waveguide may be manufactured on the glove using several different rapid typing methods (e.g. molding and hot embossing process). The molded waveguide structure may allow different optical techniques to be used in the glove configuration for different biomedical applications. Potential applications aside from force, pressure, hardness, and temperature sensing include environmental and bio sensing, magnetic resonance imaging (MRI) field detection, noninvasive blood test, electrocardiogram (EKG), electric impedance measurement, etc.

Figure 51A:
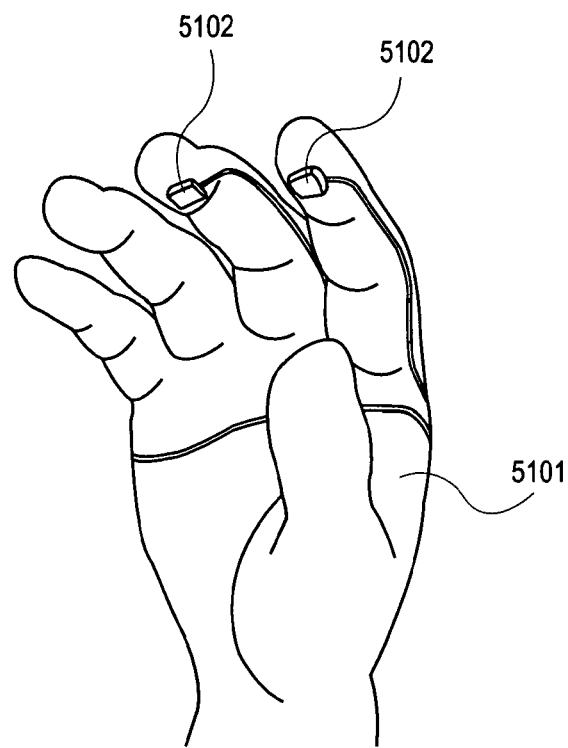
FIG. 51(a) depicts a glove having a micro-fabricated waveguide embedded on its surface according to an embodiment of the present invention.
Figure 51B:
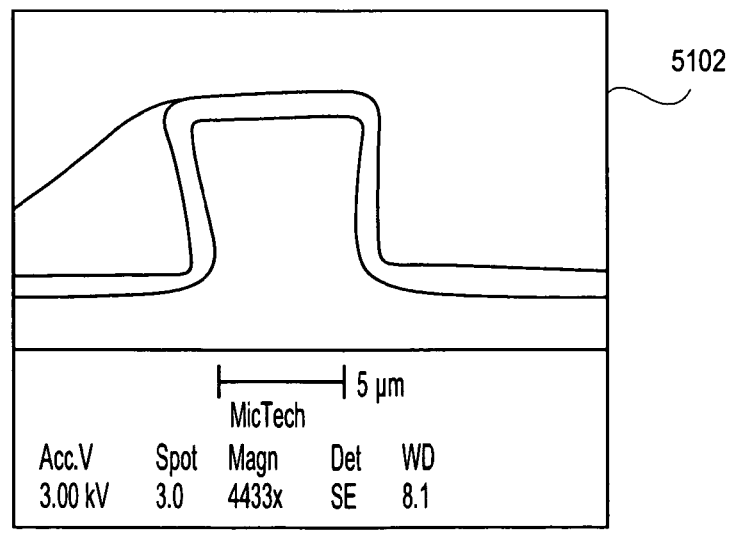
FIG. 51(b) illustrates the waveguide depicted in FIG. 51(a) in more detail according to an embodiment of the present invention.

FIG. 51(*a*) depicts a glove 5101 having a micro-fabricated waveguide 5102 embedded on its surface according to an embodiment of the present invention. FIG. 51(*b*) illustrates the waveguide 5102 in more detail according to an embodiment of the present invention. The glove materials may be latex, polyurethane, silicone rubber, nitrile rubber, polyvinyl chloride (PVC) rubber, vinyl rubber, neoprene rubber, or other suitable material. Suitable materials may be transparent in visible and IR bands (e.g. latex n~1.58 @ 415 nm, silicone n~1.397 @ 1.55 um, polyurethane n~1.6 @ 600 nm). Therefore, the waveguide and glove may be manufactured at the same time, where both are cast from a single mold that has both the waveguide and the glove pattern. Alternatively, other polymers such as silicone, Poly(methyl methacrylate) (PMMA) or polyurethane based materials may be used to fabricate the waveguides first before putting them on top of the rubber glove. This may be the case in embodiments in which the substrate material is not optically transparent in the wavelengths that the sensors are operated. Another reason would be where the sensor utilizes additional components other than the waveguide(s). This may be the case for micro-bend loss sensors and/or grating-based sensors where an applicator is made in addition to the waveguide.

Some waveguide-based optical sensors are manufactured at the time of the clinical glove is made using stamping, molding, hot embossing, laser engraving, UV lithography, X ray lithography and/or printing.

Waveguide Manufacturing Techniques for Waveguide Sensors Employing Applicators

In embodiments in which a mechanical applicator and waveguide may be made from PDMS, a flexible elastomer using soft lithography techniques may be implemented. PDMS is a widely available, clean room compatible and a physically and chemically stable silicone rubber with a wide range of applications. Sylgard 184 silicone elastomer from Dow-Corning Corporation is among the most commonly used PDMS elastomers. The primary advantages of PDMS are that it bonds easily and has very good optical properties such as high transparency, low loss, and a refractive index (n=1.43), which closely matches the indices of commercially available optical fibers. Some physical and chemical attributes of PDMS are, as compared to other polymers, a unique flexibility (shear modulus G between 100 kPa and 3 MPa), low durometer hardness (Shore A 40), very low loss tangent (tan δ<<0.001), high gas permeability, low temperature variation, and PDMS is virtually inert to most chemicals and essentially non-toxic in nature.

One use for this material is to provide an elastomeric stamp or mold for soft lithography. However, due to its unique optical and physical properties and low surface energy (~21.6 dyn/cm), PDMS allows replicas to be separated from their molds easily.

According to embodiments of the present invention, for the mechanical deformer and the rest of the packaging, molds may be constructed that include features for holding a fiber or waveguide and a mechanical applicator. The molds may be made out of SU-8 photoresist (MicroChem Corporation XP SU-8 2000 series, Newton, Mass.) on a silicon wafer where large aspect ratio micro-structures can be faithfully reproduced. The patterns may be formed on SU-8 by exposing the SU-8 with the desired patterns using photolithography. Once the molds are created, the substrate containing the optical waveguide may be placed inside an aluminum container with the waveguide or fiber holder mold, where it may be filled with PDMS to form a waveguide or holder for the fiber. The same molding process may be applied to construct the mechanical deformer. Because one may want to create a stiffer area on the diaphragm or teeth area of the deformer], a second layer of polymer material may be added onto the diaphragm using the same molding process. Later an oxygen plasma treatment may be done on all the substrates before bonding them together to form the final structure.

For other embodiments, the applicator or mechanical deformer may be manufactured using high resolution 3-D printer as the master mold. FIGS. 3-4 and 7-8 illustrate an example embodiment of fabrication of a mechanical deformer. FIG. 3 is a side view and FIG. 4 is a disassembled of the flexible sensor 104 which includes a flexible force applicator 302, a flexible force applicator 304 having a groove 306 disposed therein, an optical fiber 308 disposed in the groove 306, and an elastomeric polymer 310 disposed on the optical fiber 308 and between the two applicators 302 and 304. The illustrated applicator 302 includes several corrugated teeth 312, 314, 316, and 318. The illustrated applicator 304 includes several corrugated teeth 320, 322, and 324.

The two applicators 302 and 304 of the flexible force sensor 104 illustrated in FIG. 3 include two thin polymer plates that sandwich the optical fiber 308. The two plates are flexible and custom designed to induce bending in the optical fiber 308 via the series of corrugated teeth 312, 314, 316, 318 320, 322, and 324 inside the plates. The two applicators are initially held together using lips 402 on the edges of the applicator 302. The edges of the applicator 304 fit inside the lips 402 until the applicator 302 and 304 are permanently held in place using the elastomeric polymer 310

To test the concept a system implemented in accordance with the clinical force sensing glove system 100, a fiber-optic sensor was first modeled in ANSYS engineering simulation software to determine necessary tooth spacing and height for adequate fiber bending. FIG. 7 illustrates a model 700 according to an embodiment of the present invention. The model 700 includes a mesh of a finite element sensor for analysis of displacement under linear loading. Two outside polymer applicators 702 and 704 were given the material properties of ABS plastic and the inside elastic material 708 was modeled as polydimethylsiloxane (PDMS). An optical fiber 706 was modeled as poly(methyl methacrylate) (PMMA). The sensor was 7 mm long, 7 mm wide, and 1.2 mm thick and the optical fiber 706 had a diameter of 250 μm. The teeth were spaced 1.8 mm apart and were 0.25 mm tall. 100 N was applied to the top surface and the displacement of the teeth was measured as a function of load. This displacement data was used to calculate the angle and radius about which the optical fiber 706 was bent, which could then be used to estimate an expected attenuation curve.

The sensor was then modeled in SolidWorks computer-aided design (CAD) software with the optimized tooth spacing and heights from the finite element analysis. Seven alternating teeth were included in the sensor, four on the top applicator 702 and three on the bottom applicator 704. The exterior surfaces were contoured to minimize sharp edges that might be felt by the clinician. The bottom applicator also included a groove for the optical fiber 706 to be placed into during fabrication for stability and protection. The top applicator 702 has a lip on each side to help secure it, aligned correctly on the bottom applicator 704 during fabrication. The teeth are separated by 1.8 mm, are 0.25 mm high, and have a radius of curvature of 0.40 mm. Each applicator 702 and 704 was kept above 0.1 mm thick for structural integrity. A cavity was included between the applicators for the layer 708 of elastomeric polymer (PDMS) that would provide linear displacement when loaded.

The sensor was then converted into molds for the top and bottom applicators 702 and 704. FIG. 8 illustrates top mold 802 and bottom mold 804 according to an embodiment of the present invention. Each mold 802 and 804 includes cavities 806 or 808 for three sensors to be cast simultaneously. The molds 802 and 804 include through holes 810 for bolts to hold the two molds 802 and 804 together. The molds 802 and 804 were printed on a rapid prototype machine by RedEye Rapid Prototyping, located in Eden Prairie, Minn., and sanded for smoothness. After spraying with mold release, a 2-part liquid polyurethane plastic was spread into the cavities 806 and 808 from both plates in the molding block. The two plates were pressed together and secured with bolts. The liquid plastic was allowed to cure for 1 hour before de-molding.

Referring back to FIG. 4, after the applicators/plates have been formed the optical fiber 308, in one embodiment having a length of approximately 0.5 m length, was cleaved and centered on the bottom applicator 304, lying in the groove 306. Liquid PDMS was degassed for 30 minutes and poured over the optical fiber 308 into the cavity in the bottom applicator 304 and the top applicator 302 was centered and laid over the PDMS. Of course, although PDMS was chosen in this case, other elastomers may be suitable. The composition of the elastomeric layer affects the sensitivity and range of the sensor 104. A stiffer elastomer increases the range while a softer elastomer increases the sensitivity. The assembled sensor 104 was taped to a flat surface to keep all components together and cured overnight. After full cure, the tape was removed and the sensor 104 was ready for embedding in the glove 102.

Smooth-Cast 300 from Smooth-On, Inc., located in Easton, Pa., was used for the applicators. Smooth-Cast 300 is a two-part polyurethane that cures virtually bubble free at atmospheric pressure in 1 hour. It has a Shore D hardness of 70. The PDMS elastomer layer used was Sylgard 184 from Dow Corning, located in Midland, Mich. Smooth-Cast 300 has excellent durability over time, which is suitable for consistent force measurements in the sensor 104 over long clinical sessions.

Packaging For Waveguide Sensors Employing Applicators

For some embodiments, after the fiber sensors or waveguide sensors are completed, the sensors may be mounted onto a mannequin hand. There may be different hand sizes for different users. First, the hand may be immersed into a liquid latex solution or other suitable polymer glove material to form a layer of support structure. Then, the sensors may be disposed on top of the layer of support structure. Finally, the entire hand may be immersed into the liquid latex again to seal the sensors into a latex structure.

For waveguide sensors that don't require force applicator, two fabrication processes may be used. In one embodiment, direct fabrication of the waveguide on the glove may be used. An example of the fabrication is shown in FIG. 44. In this embodiment, a latex-based glove with a sensor is constructed at the same time. First the rectangular waveguide or rib waveguide mold is fabricated. There are several techniques that can be used to fabricate the mold. An excimer laser may be used to directly engrave the rectangular (or close to rectangular shape) groove into a mannequin hand using a three-dimensional controlling stage system. The resolution of the excimer laser should be sufficient for fabricating the waveguide dimensions. Another direct mechanism for disposing the waveguide mold onto the glove former according to an embodiment of the present invention is to electrode-deposit a layer of UV sensitive polymer on the mannequin hand and then expose the waveguide pattern on the UV sensitive polymer. A third mechanism for disposing the waveguide mold into the glove former according to an embodiment of the present invention is to deposit UV sensitive silicone rubber on a rubber glove after the glove has been made but still on the glove former and lithographically expose the waveguide pattern on the glove. Several types of patternable silicone rubber such as PDMS are currently available for commercial use. Once the waveguide trench is made on the glove former, a typical glove making process can be used. A typical latex glove fabrication process is shown in FIGS. 45-47.

In an alternative embodiment, a silicon rubber waveguide may be fabricated first and then adhered to a glove. The fabrication process may involve casting a two-layered PDMS structure from a three layered SU8 mold as shown in FIG. 48. FIG. 48(a) illustrates a three-layer SU-8 mold and FIG. 48(b) illustrates a cross-section of the SU-8 mold having a two-layer elastomeric casting.

In some embodiments, the SU8 mold includes a rectangular waveguide trench and a fiber coupler mount, as illustrated in FIG. 49. In the illustrated embodiment, FIG. 49(a) shows an SU8 waveguide trench cross section according to an embodiment of the present invention and FIG. 49(b) shows an SU8 coupler bump and a tapering 125 μm wide waveguide trench according to an embodiment of the present invention. In one embodiment, the waveguide may eventually taper down from 125 μm to a final 10 μm width.

For the SU8 mold substrate, a p-type single sided polished silicon wafer was used. The substrate was cleaned by immersing a diluted hydrofluoric acid (HF) (10:1) solution to remove any naturally grown oxide layer. The wafer was then rinsed thoroughly in deionized (DI) water, blown dry using nitrogen gas, and then dehydrated in an oven at 110° C. for at least 30 minutes. In order to create a good adhesion between the SU8 and the silicon wafer, a thin layer (2 μm) of SU8-2002 (MicroChem, MA.) was spin coated onto the silicon substrate, following instructions provided by the MicroChem. Corp.

To fabricate a waveguide trench, a 10 μm SU8-2010 resist was spun on top of the SU8-2002 layer. In order to reduce the intrinsic stress that occurred during prebaking, the temperature was ramped from 22° C. to 65° C. at a rate of 3° C./min and held at that temperature for a minute before continuing ramping to the recommended temperature of 95° C. The sample was then held at that temperature for 2 minutes before gradually ramping down to room temperature at a rate of 2° C./min.

The waveguide trench pattern may be transferred from a quartz mask to the film by exposing the film on a contact aligner with a mercury broadband light source. Based on repeated trials, it was found that the film reproduces features best when exposed at 130 mJ/cm$^2$.

For the post exposure bake, the film was placed on a hotplate for 30 minutes at 60° C. This temperature was much lower than the post bake temperature of 95° C. recommended by the manufacturer. This greatly reduced the internal stress, which may be discussed in more detail in the result and discussion section. After cooling the film to room temperature, the film was then developed in SU8 developer (PGMEA, an ethyl lactate and diacetone alcohol, MicroChem, Corp. MA.) for about 2 minutes with mild agitation.

For the coupler parts, SU8 50 (MicroChem. Corp., MA.) may be to create two large rectangular shaped plateaus. The process is basically similar to the procedure described earlier for SU8-2010. For SU8 50, a 58.5 μm (actual average resulting height ~56.2 μm) thick film is spun on top of the SU8-2010 layer. The film may be prebaked on a hotplate. The temperature may be ramped from 22° C. to 65° C. at 3° C./min and held for 7 minutes before ramping up to 95° C. The temperature may be held for 23 minutes and then ramped down to 22° C. at a rate of 2° C./min. The film may then be exposed with a coupler pattern from the quartz mask at 370 mJ/cm$^2$, and then post exposure baked at 60° C. for 30 minutes.

The whole wafer may then be immersed in SU8 developer for 6 minutes and 30 seconds. At this point, a 3-layer SU8 waveguide mold is completed, as illustrated in FIG. 49. To accommodate higher tolerance of coupling, the width of the waveguide trench may be purposely made to the size of optical fiber diameter of 125 μm, as illustrated in FIG. 49(b). The 125 μm waveguide may then be tapered down to the final 10 μm waveguide width, as illustrated in FIG. 49(a). The resulting waveguide trench may appear slightly curved.

For elastomer casting, different two-part silicone elastomers from two vendors were used: OE 43 (n=1.417 @ λ=1.55 μm from Gelest Inc.) for the core and Sylgard 184 (n=1.398 @ λ=1.55 μm from Dow Corning) for the cladding. The refractive indices of transverse electric (TE) and transverse magnetic (TM) polarizations for both elastomers were found to be the same. Based on the measurement, the optical property of the material may appear to be isotropic.

In order to release the elastomer from the mold, the mold was first silanized by exposing the film to the vapor of (Tridecafluoro-1,1,2,2-Tetrahydrooctyl) trichlorosilane (Gelest, Inc.) in a vacuum chamber for 30 minutes. Both elastomers come with a two-part kit: a prepolymer and a curing agent. Both elastomers also utilize the same preparation steps: mix base and curing agent thoroughly with a ratio of 10:1 and then degas the air bubbles generated during mixing. For the core layer, the OE 43 was spun at 5500 rpm creating a 5 μm thick film. The film was then cured at 60° C. for 4 hours on a hotplate and then Sylgard 184 (~500 μm thick) was cast on top of OE43 and cured at 60° C. overnight in an oven. Then, in one embodiment, the elastomer was carefully separated from the mold to form the finished rib waveguide structure shown in FIG. 50, here FIG. 50(*a*) shows a cross section of a PDMS waveguide, FIG. 50(*b*) shows an elastomeric coupler trench, and FIG. 50(*c*) shows the fiber inside the coupler.

Returning to FIGS. 45-47 in which a latex glove fabrication process according to embodiments of the present invention is shown, FIG. 45 shows glove formers being inspected and cleaned before the molds are dipped into coagulant tanks. FIG. 46 shows that once cleaned, the glove formers are dipped into a coagulant bath to help the latex mixture adhere to the formers and help ensure the latex is distributed evenly. The coagulant tank stage determines the thickness of the latex exam glove. The thicker the disposable gloves are to be, the longer the formers may travel in the coagulant tank. The formers are dipped into the latex mixture and may eventually travel through a series of ovens to dry the gloves. The latex mixture may have different formulations depending on the brand of clinical examination gloves being made. This liquid concoction is comprised of latex sap and chemicals that determine the elasticity of the medical glove.

FIG. 47 shows that after drying the latex mixture, the gloves are put through a leaching line to remove residual chemicals and proteins from the surface of the gloves. A good leaching line should be long, so latex proteins can be more effectively washed out. The water should also be hot and fresh to dissolve proteins better. This step helps to minimize the occurrence of latex sensitivity.

As described above, embodiments of the present invention may be implemented using hardware, software, or a combination thereof. In implementations using software, the software may be stored on a machine-accessible medium. A machine-accessible medium includes any mechanism that may be adapted to store and/or transmit information in a form accessible by a machine (e.g., a computer, network device, personal digital assistant, manufacturing tool, any device with a set of one or more processors, etc. For example, a machine-accessible medium includes recordable and non-recordable media (e.g., read only memory (ROM), random access memory (RAM), magnetic disk storage media, optical storage media, flash memory devices, etc In the above description, numerous specific details, such as, for example, particular processes, materials, devices, and so forth, are presented to provide a thorough understanding of embodiments of the invention. One skilled in the relevant art may recognize, however, that the embodiments of the present invention may be practiced without one or more of the specific details, or with other methods, components, etc. In other instances, structures or operations are not shown or described in detail to avoid obscuring the understanding of this description.

Reference throughout this specification to "one embodiment" or "an embodiment" means that a particular feature, structure, process, block, or characteristic described in connection with an embodiment is included in at least one embodiment of the present invention. Thus, the appearance of the phrases "in one embodiment" or "in an embodiment" in various places throughout this specification does not necessarily mean that the phrases all refer to the same embodiment. The particular features, structures, or characteristics may be combined in any suitable manner in one or more embodiments.

The terms used in the following claims should not be construed to limit embodiments of the invention to the specific embodiments disclosed in the specification and the claims. Rather, the scope of embodiments of the invention is to be determined entirely by the following claims, which are to be construed in accordance with established doctrines of claim interpretation.

What is claimed is:

1. A sensing apparatus, comprising:
a glove; and
a sensor disposed in the glove, the sensor comprising:
 a first flexible applicator;
 a second flexible applicator having a groove disposed therein;
 an optical fiber having a first end, a second end, and a mirror formed on a tip of the second end, wherein at least part of the second end is disposed in the groove of the second flexible applicator; and
 an elastomeric polymer disposed on the optical fiber and between the first flexible applicator and the second flexible applicator;
an optical circulator having an input port, an output port, and a port optically coupled to the first end of the optical fiber, wherein the optical circulator receives an input optical signal at the input port and directs the input optical signal into the optical fiber and wherein the optical circulator receives a reflected optical signal from the optical fiber and directs the reflected optical signal to the output port;
wherein the optical fiber is further adapted and configured to experience micro-bend loss in response to a force applied through the first flexible applicator such that intensities of the input optical signal and the reflected optical signal in the optical fiber are attenuated in response to the applied force, wherein the attenuation is proportional to the applied force.

2. The apparatus of claim 1, further comprising:
a light source operationally coupled to the input port of the optical circulator, the light source being adapted and configured to emit the optical signal; and
a light detector operationally coupled to the output port of the optical circulator, the light detector being adapted and configured to receive the reflected optical signal from the output port.

3. The apparatus of claim 2, further comprising a control channel including the light source, a second optical fiber, and a second light detector, the second optical fiber having a first end coupled to the light source and a second end coupled to the second light detector, wherein the control channel is adapted and configured to provide a reference intensity of the optical signal to measure against the attenuated intensity of the optical signal in the optical fiber.

4. The apparatus of claim 2, further comprising:
a data acquisition module operationally coupled to the light detector, the data acquisition module being adapted and configured to receive the optical signal from the light detector and determine the applied force based on the received optical signal; and
a display module operationally coupled to the data acquisition module, the display module being adapted and configured to graphically display a representation of the force applied to the optical fiber.

5. The apparatus of claim 1, wherein the glove is selected from at least one of a surgical glove and a clinical glove, wherein the sensor is disposed in the glove using an adhesive, and wherein the sensor is disposed in at least one of a finger portion of the glove and a palm portion of the glove.

6. The apparatus of claim 1, wherein the first and second flexible applicators are selected from at least one of a polymer, a plastic, a silicone rubber, and polydimethylsiloxane (PDMS), and wherein the elastomeric polymer comprises polydimethylsiloxane (PDMS).

7. The apparatus of claim 1, wherein the first and second flexible applicators each includes a set of alternating teeth, the sets of alternating teeth being adapted and configured to bend the optical fiber.

8. The apparatus of claim 1, wherein the optical sensors can be used as a hardness sensor to measure tissue hardness on patients.

9. The apparatus of claim 1 wherein the optical fiber is a multi-mode fiber.

10. The apparatus of claim 1 wherein the mirror has a thickness equal to at least one wavelength of the input light.

11. The apparatus of claim 2 wherein the light source is an incoherent light source.

12. The apparatus of claim 1 wherein the optical fiber is a parabolic index fiber.

13. The apparatus of claim 1 wherein the optical fiber is a step index fiber.

* * * * *